(12) United States Patent
Kazakov et al.

(10) Patent No.: US 11,014,957 B2
(45) Date of Patent: May 25, 2021

(54) METHODS OF LIBRARY CONSTRUCTION FOR POLYNUCLEOTIDE SEQUENCING

(71) Applicant: RealSeq Biosciences, Inc., Santa Cruz, CA (US)

(72) Inventors: Sergei A. Kazakov, San Jose, CA (US); Sergio Barberan-Soler, Santa Cruz, CA (US); Anne Dallas, Santa Cruz, CA (US); Brian H. Johnston, Scotts Valley, CA (US)

(73) Assignee: REALSEQ BIOSCIENCES, INC., Santa Cruz, CA (US)

( * ) Notice: Subject to any disclaimer, the term of this patent is extended or adjusted under 35 U.S.C. 154(b) by 0 days.

(21) Appl. No.: 16/063,535

(22) PCT Filed: Dec. 20, 2016

(86) PCT No.: PCT/US2016/067771
§ 371 (c)(1),
(2) Date: Jun. 18, 2018

(87) PCT Pub. No.: WO2017/112666
PCT Pub. Date: Jun. 29, 2017

(65) Prior Publication Data
US 2018/0371006 A1 Dec. 27, 2018

Related U.S. Application Data

(60) Provisional application No. 62/270,421, filed on Dec. 21, 2015.

(51) Int. Cl.
| | | |
|---|---|---|
| C12Q 1/68 | (2018.01) | |
| C07H 21/02 | (2006.01) | |
| C07H 21/04 | (2006.01) | |
| C12P 19/34 | (2006.01) | |
| C07H 21/00 | (2006.01) | |
| C12Q 1/6855 | (2018.01) | |
| C12Q 1/6874 | (2018.01) | |

(52) U.S. Cl.
CPC ............. *C07H 21/02* (2013.01); *C07H 21/00* (2013.01); *C07H 21/04* (2013.01); *C12P 19/34* (2013.01); *C12Q 1/68* (2013.01); *C12Q 1/6855* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 5,516,664 A | 5/1996 | Hyman | |
| 5,714,320 A | 2/1998 | Kool | |
| 5,854,033 A | 12/1998 | Lizardi | |
| 6,077,668 A | 6/2000 | Kool | |
| 6,667,176 B1 * | 12/2003 | Funk | C12N 15/1034 435/363 |
| 7,824,863 B2 | 11/2010 | Cole et al. | |
| 7,927,798 B2 | 4/2011 | Zheng et al. | |
| 9,212,378 B2 | 12/2015 | Choi et al. | |
| 9,816,130 B2 | 11/2017 | Kazakov | |
| 2002/0127569 A1 | 9/2002 | Weisburg et al. | |
| 2003/0138358 A1 | 7/2003 | Eipel et al. | |
| 2004/0171047 A1 | 9/2004 | Dahl et al. | |
| 2005/0272185 A1 | 12/2005 | Jacobsen et al. | |
| 2005/0277139 A1 | 12/2005 | Bentwich et al. | |
| 2006/0003337 A1 | 1/2006 | Brandis et al. | |
| 2006/0019258 A1 | 1/2006 | Yeakley | |
| 2006/0063181 A1 | 3/2006 | Green et al. | |
| 2006/0078894 A1 | 4/2006 | Winkler et al. | |
| 2006/0166245 A1 | 7/2006 | Potter et al. | |
| 2006/0188893 A1 | 8/2006 | Kumar et al. | |
| 2007/0292878 A1 | 12/2007 | Raymond | |
| 2008/0160511 A1 | 7/2008 | Dawson et al. | |
| 2008/0241831 A1 | 10/2008 | Fan et al. | |
| 2009/0023151 A1 | 1/2009 | Dawson et al. | |
| 2009/0170719 A1 | 7/2009 | Kazakov et al. | |
| 2011/0117648 A1 | 5/2011 | Chiou et al. | |
| 2011/0172105 A1 | 7/2011 | Gage et al. | |
| 2011/0244523 A1 | 10/2011 | Tuschl et al. | |
| 2012/0010091 A1 * | 1/2012 | Linnarson | C12N 15/1096 506/7 |
| 2012/0164651 A1 | 6/2012 | Kazakov et al. | |
| 2012/0208189 A1 | 8/2012 | Xu et al. | |
| 2012/0329054 A1 | 12/2012 | Dawson et al. | |
| 2013/0059736 A1 | 3/2013 | Galas et al. | |
| 2014/0031239 A1 * | 1/2014 | Kotsbak | C12Q 1/6874 506/2 |
| 2014/0287468 A1 | 9/2014 | Richard | |

(Continued)

FOREIGN PATENT DOCUMENTS

| | | |
|---|---|---|
| EP | 1627925 A1 | 2/2006 |
| EP | 1978104 A1 | 10/2008 |

(Continued)

OTHER PUBLICATIONS

Valouev et al (Genome Research 18:1051-63) (Year: 2010).*
Sawa et al (Nature 373:487-93) (Year: 1995).*
Aird et al., Analyzing and minimizing PCR amplification bias in Illumina sequencing libraries, Genome Biol., 2011, 12: R18.
Aravin, et al. Identification and characterization of small RNAs involved in RNA silencing. FEBS Lett. Oct. 31, 2005;579(26):5830-40. Epub Aug. 18, 2005.
Arroyo, J.D. et al. Argonaute2 complexes carry a population of circulating microRNAs independent of vesicles in human plasma, 2011. Proc. Natl. Acad. Sci. USA vol. 108, pp. 5003-5008.

(Continued)

*Primary Examiner* — Christopher M Gross
(74) *Attorney, Agent, or Firm* — Wilson Sonsini Goodrich & Rosati

(57) ABSTRACT

Disclosed herein are methods and compositions for the detection of small RNAs in a sample. The methods and compositions disclosed herein may be used for preparing sequencing libraries of the small RNAs, fragments of RNAs and DNAs.

10 Claims, 31 Drawing Sheets

Specification includes a Sequence Listing.

(56) References Cited

U.S. PATENT DOCUMENTS

| | | |
|---|---|---|
| 2015/0051099 A1 | 2/2015 | Kazakov et al. |
| 2015/0184223 A1 | 7/2015 | Keller et al. |
| 2015/0211046 A1 | 7/2015 | Kazakov et al. |
| 2018/0066311 A1 | 3/2018 | Kazakov |

FOREIGN PATENT DOCUMENTS

| | | |
|---|---|---|
| EP | 2663639 A2 | 11/2013 |
| EP | 2419537 B1 | 1/2014 |
| EP | 2794926 A1 | 10/2014 |
| EP | 2961852 A1 | 1/2016 |
| WO | WO-03002761 A1 | 1/2003 |
| WO | WO-2005098029 A2 | 10/2005 |
| WO | WO-2006007569 A2 | 1/2006 |
| WO | WO-2006102309 A2 | 9/2006 |
| WO | WO-2006108422 A2 | 10/2006 |
| WO | WO-2010120803 A2 | 10/2010 |
| WO | WO-2013096839 A1 | 6/2013 |
| WO | WO-2014134320 A1 | 9/2014 |
| WO | WO-2020094040 A1 | 5/2020 |

OTHER PUBLICATIONS

Asaga, S. et al. Direct Serum Assay for MicroRNA-21 Concentrations in Early and Advanced Breast Cancer, 2011. Clinical Chemistry, vol. 57, No. 1, pp. 84-91.

"Bae, Jung-Hoon et al. Template-blocking PCR: An advanced PCR technique for genome walking. Analytical Biochemistry 398:112-116 (2010)".

Basyuk et al., "Human let-7 stem-loop precursors harbor features of RNase III cleavage products" Nucleic Acids Research (2003) 31(22):6593-6597.

Beaucage, S.L. Strategies in Preparation of DNA oligonucleotide arrays for diagnostic applications. Aug. 2001, Curr. Med. Chem. vol. 8, No. 10, pp. 12-13-1244.

Bentwich et al., Identification of hundreds of conserved and non-conserved human microRNAs, Nat. Genet., 2005, 37: 766-70.

Bryant, R.J. et al. Changes in circulating microRNA levels associated with prostate cancer, 2012 British Journal of Cancer, vol. 106, pp. 768-774.

Burroughs et al., pre-miRNA profiles obtained through application of locked nucleic acids and deep sequencing reveals complex 5'/3' arm variation including concomitant cleavage and polyuridylation pattern, Nucleic Acids Res., 2012, 40:1424-37.

Bushati, N., Cohen, S.M. 2007. Annu. Rev. Cell Dev. Biol. 23: 175-205.

Chammongpol, et al., miRtect-IT: a novel method for small RNA detection, Biotechniques, Jan. 2008; 44(1):129-31.

Chapin et al. "Ultrasensitive Multiplexed MicroRNA Quantification on Encoded Gel Microparticles Using Rolling Circle Amplification" Anal Chem. 83(18): 7179-7185.

Chen, C. et al. Real-time quantification of microRNAs by stem-loop RT-PCR, 2005. Nucleic Acids Res. 33: e179.

Chen et al., Real-time quantification of microRNAs by stem-loop RT-PCR, Nucleic Acids Res., Nov. 27, 2005;33(20):e179.

Cheng et al., "Highly Sensitive Determination of microRNA Using Target-Primed and Branched Rolling-Circle Amplification" Angew. Chem. Int. Ed. (2009) 48:3268-3272.

Co-pending U.S. Appl. No. 16/007,769, filed Jun. 13, 2018.

Demidov et al., Rolling-circle amplification in DNA diagnostics: the power of simplicity, Expert Rev. Mol. Diagn., 2002, 2(6):89-95.

EP 10765038.4 Office action dated Mar. 13, 2013.

EP 10765038.4 Search Report dated Jul. 23, 2012.

Etheridge, A. et al. Extracellular microRNA: a new source of biomarkers, Dec. 1, 2011. Mutat. Res. vol. 717, No. 1-2, pp. 85-90.

"European Patent No. 2794926 Extended Search Report dated Sep. 29, 2015".

Fang et al., Attomole microarray detection of microRNAs by nanoparticle-amplified SPR imaging measurements of surface polyadenylation reactions, J. Am. Chem. Soc., 2006, 128: 14044-6.

Frieden et al., "Tightening the Belt on Polymerases: Evaluating the Physical Constrainst on Enzyme Substrate Size" Angew. Chem. Int. Ed. (1999) 38(24):3654-3657.

Fuchs, Ryan T. et al. Bias in Ligation-Based Small RNA Sequencing Library Construction Is Determined by Adaptor and RNA Structure. PLoS One, 10(5):e0126049: 1-24 (May 5, 2015).

Gallo, A. et al. The Majority of MicroRNAs Detectable in Serum and Saliva Is Concentrated in Exosomes, Mar. 2012.*PLoS One*, vol. 7, No. 3, e30679.

Gu, L-Q. et al. Detection of miRNAs with a nanopore single-molecule counter, Jul. 2012.*Expert Rev.Mol. Diagn.* vol. 12, No. 6, pp. 573-584.

Hafner, et al., RNA-ligase-dependent biases in miRNA representation in deep-sequenced small RNA cDNA libraries, RNA, 2011, 17: 1697-712.

Harcourt, et al. Amplified microRNA detection by templated chemistry. Nucleic Acids Res. May 2012;40(9):e65. doi: 10.1093/nar/gkr1313. Epub Jan. 25, 2012.

How many species of bacteria are there, wisegeek.com, accessed Jan. 21, 2014.

International Application No. PCT/US16/67771 International Search Report and Written Opinion dated Apr. 28, 2017.

"International Application No. PCT/US/2014/019055 International Preliminary Report on Patentability dated Sep. 11, 2015".

International Application No. PCT/US2014/019055 International search report and written opinion dated May 21, 2014.

International Application No. PCT/US2016/067771 international Preliminary Report on Patentability dated 26, 2018.

Jayaprakash et al., Identification and remediation of biases in the activity of RNA ligases in small-RNA deep sequencing, Nucleic Acid Res., 2011, 39: e141.

Jiang, et al. Real-time expression profiling of microRNA precursors in human cancer cell lines. Nucleic Acids Res. Sep. 28, 2005;33(17):5394-403. Print 2005.

Jonstrup, et al. A microRNA detection system based on padlock probes and rolling circle amplification. RNA. Sep. 2006;12(9):1747-52. Epub Aug. 3, 2006.

Jost, R. et al. 2007. Biotechniques 43: 206-11.

Kawano, Mitsuoki et al. Reduction of non-insert sequence reads by dimer eliminator LNA oligonucleotide for small RNA deep sequencing. Biotechnigues, Informa Healthcase, U.S. vol. 49, No. 4, pp. 751-755, Oct. 1, 2010.

Kim, D.J. et al. Plasma Components Affect Accuracy of Circulating Cancer-Related MicroRNA Quantitation, Jan. 2012. J. Mol. Diagn. vol. 14, No. 1, pp. 71-80.

Kim, Y.K. et al. Short Structured RNAs with Low GC Content Are Selectively Lost during Extraction from a Small Number of Cells, Jun. 29, 2012. Molecular Cell, vol. 46, pp. 893-895.

Kong et al., "PCR hot-start using duplex primers" Biotechnology Letters (2004) 26:277-280.

Kroh, E.M. et al. Analysis of circulating microRNA biomarkers in plasma and serum using quantitative reverse transcription-PCR (qRT-PCR)Apr. 2010. Methods vol. 50, No. 4,pp. 298-301.

Kumar, et al. miR-ID: a novel, circularization-based platform for detection of microRNAs. RNA. Feb. 2011;17(2):365-80. doi: 10.1261/rna.2490111. Epub Dec. 17, 2010.

Kumar, P. et al. miR-Id: A novel, circularization-based platform for detection of microRNAs, 2011. RNA vol. 17, pp. 365-380.

Kurschat et al., Optimizing splinted ligation of highly structured small RNAs, RNA, 2005, 11: 1909-14.

Langmead et al. Fast gapped-read alignment with Bowtie 2. Nature Methods 9:357-359 (2012).

Linsen et al., Limitations and possibilities of small RNA digital gene expression profiling, Nat. Methods, 2009, 6: 474-6.

Lizardi, et al. Mutation detection and single-molecule counting using isothermal rolling-circle amplification. Nat Genet. Jul. 1998;19(3):225-32.

Lu, et al. Construction of Small RNA cDNA libraries for deep sequencing, Methods, vol. 43, No. 2, pp. 110-117, Oct. 2007.

Lu, et al. PCR-based expression analysis and identification of microRNAs. J RNAi Gene Silencing. Jul. 28, 2005;1(1):44-9.

Mammal. wikipedia.com, accessed Sep. 22, 2011.

(56) References Cited

OTHER PUBLICATIONS

Maroney, et al. A rapid, quantitative assay for direct detection of microRNAs and other small RNAs using splinted ligation. RNA. Jun. 2007;13(6):930-6. Epub Apr. 24, 2007.
Martin, M. et al. Cutadapt Removes Adapter Sequences From High-Throughput Sequencing Reads. EMBnet.Journal Bioinformatics in Action 17(1):10-12 (2011).
Mattie, et al., Optimized high-throughput microRNA expression profiling provides novel biomarker assessment of clinical prostate and breast cancer biopsies, Mol Cancer, Jun. 19, 2006;5:24.
McCormick et al., Experimental design, preprocessing, normalization and differential expression analysis of small RNA sequencing experiments, Silence, 2011, 2: 2.
McDonald, J.S. et al. Analysis of Circulating MicroRNA: Preanalytical and Analytical Challenges, 2011. Clinica Chemistry, vol. 57, pp. 833-840.
Mitsuhashi, M. et al. Quantification of mRNA in Whole Blood by Assessing Recovery of RNA and Efficiency of cDNA Synthesis. 2006. Clinical Chemistry vol. 52, No. 4, pp. 634-642.
Moltzahn, F. et al. Microfluidic-Based Multiplex qRT-PCR Identifies Diagnostic and Prognostic microRNA Signatures in the Sera of Prostate Cancer Patients, Jan. 15, 2011. Cancer Res. vol. 71, No. 2, pp. 550-560.
Munafo et al., Optimization of enzymatic reaction conditions for generating representative pools of cDNA from small RNA, RNA, 2010, 16: 2537-52.
Murinae. Wikipedia.com, accessed Mar. 18, 2013.
Nallulr et al. Signal amplification by rolling circle amplification on DNA microarrays. Nucleic Acids Res. (2001) vol. 29, No. 23, e118, pp. 1-9.
Navarro et al., "Reverse transcription polymerase chain reaction protocols for cloning small circular RNAs" Journal of Virological Methods (1998) 73:1-9.
Office action dated Oct. 20, 2016 for U.S. Appl. No. 14/367,200.
Overhoff et al., Quantitative detection of siRNA and single-stranded oligonucleotides: relationship between uptake and biological activity of siRNA, Nucleic Acids Res., Dec. 2, 2004;32(21):e170.
PCT/US2010/030922 International Preliminary Report on Patentability dated Jan. 25, 2011.
PCT/US2010/030922 Search Report and Written Opnion dated Jan. 26, 2011.
PCT/US2012/071374 International Preliminary Report on Patentability dated Jun. 24, 2014.
PCT/US2012/071374 International Search Report dated Apr. 8, 2013.
PCT/US2012/071374 Written Opinion dated Apr. 5, 2013.
Plant. Wikipedia.com, accessed Aug. 28, 2015.
Raabe et al., The rocks and shallows of deep RNA sequencing: Examples in the Vibrio cholerae RNome, RNA, 2011, 17: 1357-66.
Raymond, et al., Simple, quantitative primer-extension PCR assay for direct monitoring of microRNAs and short-interfering RNAs, RNA, Nov. 2005;11(11):1737-44.
Regan, P.M., Margolin, A.B. Development of a nucleic acid capture probe with reverse tranacrlptasepolymaraae chain reaction to detect poliovirus in groundwater.Feb. 1997. J. Virol. Methods. vol. 64, No. 1, pp. 65-72.
Reid, G. et al. Circulating microRNAs: Association with disease and potential use as biomarkers 2011. Crit. Rev. Oncol. Hematol. vol. 80, pp. 193-208.
Roeder, Thomas Solid-phase cDNA library construction, a versatile approach. Nucleic Acids Research, 26(14):3451-3452 (1998).
Saba, et al., Target labelling for the detection and profiling of microRNAs expressed in CNS tissue using microarrays, BMC Biotechnol., Dec. 12, 2006;6:47.
Sharbati-Tehrani, et al. miR-Q: a novel quantitative RT-PCR approach for the expression profiling of small RNA molecules such as miRNAs in a complex sample. BMC Mol Biol. Apr. 10, 2008;9:34. doi: 10.1186/1471-2199-9-34.
Silverman et al., Practical and general synthesis of 5'-adenylated RNA (5'-AppRNA), RNA, 2004, 10: 731-46.

Sioud, et al., Profiling microRNA expression using sensitive cDNA probes and filter arrays, Biotechniques, Oct. 2004;37(4):574-6, 578-80.
Sridhara, S. et al. RNA-RNA ligation: Methods, Prospects and Applications, GERF Bulletin of Biosciences, vol. 2, No. 2, pp. 32-35, Dec. 2011.
Sun et al., A bias-reducing strategy in profiling small RNAs using Solexa, RNA, 2011, 17: 2256-62.
Szymkowiak, et al., Rapid method for the characterization of 3' and 5' UTRs of influenza viruses, J Virol Methods, Jan. 2003;107(1):15-20.
Tanaka, A. et al. All-in-One Tube Method for Quantitative Gene Expression Analysis in Oligo-dT30 Immobilized PCR Tube Coated with MPC Polymer. 2009. Anal. Sci. vol. 25, pp. 109-114.
Thomas et al. Determination of the ex vivo rates of human immunodeficiency virus type 1 reverse transcription by using novel strand-specific amplification analysis. J. Virology (2007) vol. 81, No. 9, pp. 4798-4807.
Tian et al., Sequencing bias: comparison of different protocols of microRNA library construction, BMC Biotechnol, 2010, 10: 64.
U.S. Appl. No. 13/264,122 Final Office Action dated May 8, 2014.
U.S. Appl. No. 13/264,122 Non-final Office Action dated Oct. 24, 2013.
U.S. Appl. No. 14/367,200 Final Office Action dated Apr. 27, 2017.
U.S. Appl. No. 14/367,200 Notice of Allowance dated Jul. 12, 2017.
U.S. Appl. No. 14/367,200 Office Action dated Oct. 20, 2016.
U.S. Appl. No. 14/367,200 Restriction Requirement dated May 27, 2016.
U.S. Appl. No. 14/771,195 Non-Final Office Action dated May 25, 2017.
Vigneaultet al., Efficient microRNA capture and bar-coding via enzymatic oligonucleotide adenylation, Nat. Methods, 2008, 5: 777-9.
Virus. Wikipedia.com, Accessed Nov. 24, 2012.
Wages, et al. Affinity Purification of RNA: Sequence-Specific Capture by Nonionic Morpholino Probes, BioTequniques 23(6):1116-1121 (1997).
Wang et al. Oligoribonucleotide circularization by 'template-mediated' ligation with T4 RNA ligase: synthesis of circular hammerhead ribozymes. Nucleic Acids Res. (1998) vol. 26, No. 10, pp. 2502-2504.
Yolken, R.H. et al. Solid phase capture method for the specific amplification of microbial nucleic acids-avoidance of false-positive and false-negative reactions. Apr. 1991. Mol. Cell. Probes. vol. 5, No. 2, pp. 151-156.
Zen, K., Zhang, C.Y. Circulating microRNAs: a novel class of biomarkers to diagnose and monitor human cancers.Mar. 2012. Med. Res. Rev. vol. 32, No. 2, pp. 326-348.
Zhang, B., Farwell, M.A. microRNAs: a new emerging class of players for disease diagnostics and gene therapy.2008. J. Cell. Mol. Med. vol. 12, pp. 3-21.
Zhang et al., "Amplification of target-specific, ligation-dependent circular probe" Gene (1998) 211:277-285.
Barberan-Soler et al., Decreasing miRNA sequencing bias using a single adapter and circularization approach. Genome Biology. 19(1):105 (2018).
European Application No. 14757711.8 Extended Search Report dated Aug. 18, 2016.
European Patent Application No. 16879969 Extended European Search Report dated May 21, 2019.
Ingolia et al., The ribosome profiling strategy for monitoring translation in vivo by deep sequencing of ribosome-protected mRNA fragments. Nature Protocols. 7(8):1534-1550 (2012).
Ingolia, Genome-wide translational profiling by ribosome footprinting. Methods in Enzymology. 470:119-142 (2010).
Kwon Y.S., Small RNA library preparation for next-generation sequencing by single ligation, extension and circularization technology. Biotechnology Letters. 33(8):1633-1641 (2011).
Sterling et al., An efficient and sensitive method for preparing cDNA libraries from scarce biological samples. Nucleic Acids Research. 43(1):e1 (2015).
U.S. Appl. No. 16/007,769 Office Action dated Sep. 30, 2019.

(56) References Cited

OTHER PUBLICATIONS

PCT/US2018/37411 International Search Report and Written Opinion dated Nov. 8, 2018.
U.S. Appl. No. 15/725,999 Final Office Action dated Jul. 10, 2020.
PCT/US2018/037411 International Preliminary Report on Patentability dated Dec. 17, 2019.
U.S. Appl. No. 16/007,769 Final Office Action dated Feb. 12, 2020.
U.S. Appl. No. 15/725,999 Non-Final Office Action dated Jan. 16, 2020.

* cited by examiner

FIG. 6B

Inversed Combo Adapter – product of RT from circular CAD

▨ - Terminal blocking modification preventing extension

Combo Adapter dimer – product of CAD ligation

SEQUENCE LISTING

<160> NUMBER OF SEQ ID NOS: 17

<210> SEQ ID NO 1
<211> LENGTH: 22
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 1
uagcagcacg uaaauauugg cg            22

<210> SEQ ID NO 2
<211> LENGTH: 21
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 2
aggcaagaug cuggcauagc u                                      21

<210> SEQ ID NO 3
<211> LENGTH: 22
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 3
ucccugagac ccuaacuugu ga                                     22

<210> SEQ ID NO 4
<211> LENGTH: 22
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 4
uaacacuguc ugguaaagau gg                                     22

<210> SEQ ID NO 5
<211> LENGTH: 23
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 5
guccaguuuu cccaggaauc ccu                                    23

<210> SEQ ID NO 6
<211> LENGTH: 23
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 6
caacggaauc ccaaaagcag cug                                    23

<210> SEQ ID NO 7
<211> LENGTH: 22
<212> TYPE: RNA
<213> ORGANISM: Homo sapiens
<220> FEATURE:
<223> OTHER INFORMATION: 5'-Phosphate
<220> FEATURE:
<223> OTHER INFORMATION: 3'-OH

<400> SEQUENCE: 7
cuacaaaggg aagcacuuuc uc                                     22

<210> SEQ ID NO 8
<211> LENGTH: 22
<212> TYPE: RNA
<213> ORGANISM: Homo sapiens
<220> FEATURE:

```
<223> OTHER INFORMATION: 5'-Phosphate
<220> FEATURE:
<223> OTHER INFORMATION: 3'-OH

<400> SEQUENCE: 8
ucagcaaaca uuuauugugu gc                                              22

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-App
<220> FEATURE:
<221> NAME/KEY: modified_base
<222> LOCATION: (22)..(23)
<223> OTHER INFORMATION: Abasic 1',2'-dideoxyribose residues, idSp
<220> FEATURE:
<223> OTHER INFORMATION: 3'-Phosphate

<400> SEQUENCE: 9
tggaattctc gggtgccaag gnnguucaga guucuacagu ccgacgaucu                50

<210> SEQ ID NO 10
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Biotin-TEG
<220> FEATURE:
<223> OTHER INFORMATION: 3'-OH

<400> SEQUENCE: 10 aaaaa                                                                  5

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Biotin-TEG
<220> FEATURE:
<223> OTHER INFORMATION: 3'-OH

<400> SEQUENCE: 11
aaaaaaaaaa                                                            10

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-AmMC6
<220> FEATURE:
<223> OTHER INFORMATION: 3'-AmMO
```

```
<400> SEQUENCE: 12
gagaattcca tttttttttt                                              20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-OH

<400> SEQUENCE: 13
ccttggcacc cgagaattcc a                                            21

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-OH

<400> SEQUENCE: 14
aatgatacgg cgaccaccga gatctacacg ttcagagttc tacagtccg              49

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-OH

<400> SEQUENCE: 15
caagcagaag acggcatacg agatgtcgtc gtgactggag ttccttggca cccgagaatt  60
cca                                                                63

<210> SEQ ID NO 16
<211> LENGTH: 23
<212> TYPE: RNA
<213> ORGANISM: Homo sapiens
<220> FEATURE:
<223> OTHER INFORMATION: 5'-OH
<220> FEATURE:
<223> OTHER INFORMATION: 3'-OH

<400> SEQUENCE: 16
caacggaauc ccaaaagcag cug                                          23

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Phosphate
<220> FEATURE:
```

```
<221> NAME/KEY: modified_base
<222> LOCATION: (22)..(23)
<223> OTHER INFORMATION: Abasic 1',2'-dideoxyribose residues, idSp
<220> FEATURE:
<223> OTHER INFORMATION: 3'-Phosphate

<400> SEQUENCE: 17
tggaattctc gggtgccaag gnnguucaga guucuacagu ccgacgaucu          50
```

METHODS OF LIBRARY CONSTRUCTION FOR POLYNUCLEOTIDE SEQUENCING

RELATED APPLICATIONS

This application is a U.S. National Stage entry of International Application No. PCT/US2016/067771, filed Dec. 20, 2016, which claims the benefit of U.S. Provisional Patent Application No. 62/270,421, filed Dec. 21, 2015, which are incorporated herein by reference in their entirety.

GOVERNMENT SUPPORT

This invention was made with government support under Small Business Innovation Research grant 1R43HG007788-01A1 awarded by the National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 16, 2016, is named 40220_711_601_SL.txt and is 4,685 bytes in size.

FIELD OF THE INVENTION

The present invention is in the field of molecular and cell biology. More specifically, it concerns methods and compositions that find use in the identification, detection, quantification, expression profiling of small polynucleotides and small fragments of large polynucleotides (RNA and DNA), both naturally occurring and man-made. The present invention finds use in a variety of genomic research and diagnostic applications, including medical, agricultural, food and biodefense fields. Polynucleotides of interest may represent biomarkers of infection (e.g., viral and bacterial), or diseases such as cancer, genetic disorders, and metabolic disorders.

SUMMARY OF THE INVENTION

Disclosed herein are combo adapters in the form of a plurality of nucleic acid residues, comprising: a 5'-proximal segment and a 3'-proximal segment, wherein each proximal segment comprises at least one sequencing adapter, detection sequences, or a combination thereof; 5'-end and 3'-end groups that allow first and second consecutive ligation reactions either directly or after conversion of one or both of these end groups to ligatable 5'-end and 3'-end group(s), the ligation reactions comprising: first, intermolecular ligation of said combo adapter to a sample polynucleotide to produce an adapter-polynucleotide ligation product; and a second intramolecular reaction resulting in circularization of the adapter-polynucleotide ligation product to produce a circularized adapter-polynucleotide ligation product; and a template-deficient segment that restricts primer extension by a polymerase over said template-deficient segment. The template-deficient segment may allow only one round of primer extension on said circularized adapter-polynucleotide ligation product, thereby preventing rolling-circle amplification (RCA). The combo adapter may comprise at least one RNA residue, DNA residue, modified nucleic acid residue, or non-nucleotide residue, or a combination thereof. The modified residue may be located in the template-deficient segment. The combo adapter may comprise at least one sequence selected from: a sequencing adapter, a primer binding site, a detection sequence, a probe hybridization sequence, a capture oligonucleotide binding site, a polymerase binding site, an endonuclease restriction site, a sequencing bar-code, an indexing sequence, a Zip-code, one or more random nucleotides, a unique molecular identifier (UMI), and a sequencing flow-cell binding site, and combinations thereof. The at least one sequencing adapter may enable sequencing of the adapter-polynucleotide ligation product or complement thereof by sequencing methods selected from: standard Sanger sequencing; next-generation sequencing; and single-molecule sequencing. The combo adapter may be a 5'-combo adapter comprising end groups selected from: a) a 5'-OH and a 3'-OH; and b) a 5'-phosphate (5'-p) and a 3'-phosphate (3'-p), before ligation of said 5'-combo adapter to the 5'-end of the sample polynucleotide. The combo adapter may be a 3'-combo adapter comprising a 5'-p or 5'-adenylated (App) group and a 3'-p, before ligation of said 3'-combo adapter to the 3'-end of the sample polynucleotide. The 5'- and/or 3'-end groups of the combo adapter may contain a blocking group preventing circularization or concatamerization of combo adapter while allowing circularization of the said adapter-polynucleotide ligation products. The 5'-end and/or 3'-end of the combo adapter may contain a reversible blocking group preventing circularization or concatamerization of combo adapter while allowing its ligation with a sample polynucleotide, wherein said reversible blocking group requires chemical, photochemical or enzymatic conversion to active end group prior to the circularization of the adapter-polynucleotide ligation product. The reversible blocking group may be a 3'-end-blocking group selected from: 3'-p, 2',3'-cyclic phosphate (2',3'>p), 3'-O-(α-methoxyethyl)ether, and 3'-O-isovaleryl ester. The reversible blocking group may be a 5'-end-blocking group selected from: 5'-OH, 5'-ppp, 5'-p, and 5'-App. The combo adapter may comprise at least one cleavage site positioned within its 5'-proximal and/or 3'-proximal segments; or between its 5'-proximal and 3'-proximal segments; or at the junction of its 5'-end and 3'-ends when it is circularized. The at least one cleavage site may be a substrate for a nuclease selected from: Uracil-DNA glycosylase, Endonuclease V, a restriction endonuclease, a ribozyme, a deoxyribozyme, an artificial chemical nuclease, RNase H, RNase H II, Duplex-specific Nuclease, and Cas9 nuclease.

Further disclosed herein are methods for preparing a sequencing library for a plurality of sample polynucleotides in a sample, comprising: ligating a combo adapter to the plurality of sample polynucleotides to produce a plurality of adapter-polynucleotide ligation products, wherein said combo adapter comprises a 5'-proximal segment and a 3'-proximal segment, and wherein at least one of the 5' proximal segment or 3' proximal segment comprises a sequencing adapter; circularizing said plurality of adapter-polynucleotide ligation products by ligating their 5' ends to their 3' ends to produce a plurality of circularized adapter-polynucleotide ligation products; hybridizing a first primer comprising a sequence at least partially complementary to the 5'-proximal segment of said combo adapter, to said circularized adapter-polynucleotide ligation products; extending said first primer with a polymerase to produce a plurality of monomeric nucleic acids, wherein each of the monomeric nucleic acids is complementary to: at least one sample polynucleotide of the plurality of sample polynucleotides flanked by at least a portion of the sequencing adapter; and amplifying said plurality of monomeric nucleic acids using said first primer and a second primer, wherein the sequence of the second primer is at least partially complementary to the 3'-proximal segment of said combo adapter, to produce amplicon(s) comprising the sequencing library. The sample polynucleotide may comprise: a 5'-end group selected from: 5'-phosphate (5'-p); 5'-OH, 5'-triphosphate (5'-ppp) or other 5'-end group that can be converted to 5'-p, 5'-OH or 5'-App before ligation to the combo adapter; a 3'-end group selected from: a 3'-OH, 3'-p, 2'-p or 2',3'-cyclic phosphate (2',3'>p) that may be converted to 3'-OH or 3'-p or before ligation to the combo adapter; and a 2'-group at its 3'-terminal residue selected from: 2'-H, 2'-OH, 2'-phosphate (2'-p) or 2'-O-methyl (2'-OMe) at the 3'-end. The method may comprise converting the 5'- and 3'-end groups of said sample polynucleotide to: a) 5'-OH, 2'-OH/3'-OH; or b) to 5'-OH and 2',3'>p. The method may comprise converting the 5'-OH end to 5'-p end while maintaining 3' end group selected from 2',3'>p, 3'-p, or 2'-p. The method may comprise converting the 3'-OH end of sample polynucleotide is converted to 3'-p end by ligation with 5'-adenylated pNp (5'-AppNp) while maintaining the 5'-p end. The method may comprise ligating the combo adapter to the 3' end of the sample polynucleotide, wherein the combo adapter comprises an adenylated 5' end (5'-App) and a 3'-p, and wherein the 3'p is ligated to a 3'-OH end of a sample polynucleotide having a 5'-p or 5'-OH. The method may comprise ligating the combo adapter to the 3' end of the sample polynucleotide, wherein the combo adapter comprising 5'-p and 3'-p ends is ligated to a 3'-OH end of a sample polynucleotide comprising a 5'-OH end. The method may comprise ligating the combo adapter to the 5' end of the sample polynucleotide, wherein the combo adapter comprising 5'-p and 3'-p ends is ligated to a 5'-OH end of a sample polynucleotide having a 3'-OH end or a 2',3'>p end. The method may comprise ligating the combo adapter to the 5' end of the sample polynucleotide, wherein the combo adapter comprises 5'-OH and 3'-OH ends, and is ligated to a 5'-p end of a sample polynucleotide comprising a phosphorylated 3'-end selected from 2',3'>p, 3'-p, or 2'-p. Ligating and/or circularizing may comprise contacting the combo adapter and/or the plurality of adapter-polynucleotide ligation products with a ligase selected from: a) 3'-OH ligase ligating 5'-p to 3'-OH or 5'-App to 3'-OH; b) 5'-OH ligase ligating 5'-p to 3-phosphorylated end selected from: 3'-p, 2',3'>p or 2'-p; and combinations thereof. Ligating and/or circularizing may comprise use of a ligase selected from: a 3'-OH ligase used for ligating and circularizing; a 5'-OH ligase used for ligating and circularizing; a 3'-OH ligase used for ligating and 5'-OH ligase used for circularizing; and a 5'-OH ligase used for ligating and 3'-OH ligase used for circularizing. Ligating and/or circularizing may be performed under conditions selected from: in the absence of ATP; in the presence of ATP; and in the presence of co-factors selected from: $Mg^{2+}$, $Mn^{2+}$, ATP, GTP, and combinations thereof. The method may comprise converting the 5'-end and/or 3'-end groups of the adapter-polynucleotide ligation product before said circularizing, wherein converting comprises a conversion selected from: a) 5'-OH to 5'-p; b) 3'-p to 3'-OH; c) 2'-p to 2'-OH; and d) 2',3'>p to 2'-OH/3'-OH. The 5'-end and/or 3'-end groups of the adapter-polynucleotide ligation product may directly allow its circularization. The 5'-end and/or 3'-end groups of the combo adapter may contain a blocking group preventing its circularization or concatamerization while allowing circularization of the said adapter-polynucleotide ligation products by 5'-OH ligase or 3'-OH ligase. The blocking group may be selected from: a) 5'-p and 5'-App of 3'-combo adapter for 5'-OH ligase; or b) 3'-p of 5'-combo adapter for 3'-OH ligase. The combo adapter may contain a 5'-end and/or 3'-end reversible blocking group preventing circularization or concatamerization of combo adapter while allowing its ligation with a sample polynucleotide, wherein said reversible blocking group requires a conversion to active end group prior to the circularization of the adapter-polynucleotide ligation product. The method may comprise converting the 3' end blocking group to 3'-OH, wherein said 3'-end reversible blocking group of 3'-combo adapter is selected from 3'-p, 2'-p and 2',3'>p. The method may comprise a) converting 5'-p to 5'-OH; b) converting 5'-ppp to 5'-p; or c) converting 5'-OH to 5'-p, wherein said 5'-end reversible blocking group of 5'-combo adapter is selected from: 5'-p, 5'-ppp and 5'-OH. The method may comprise converting the 5' end or 3' end, and comprising contacting the plurality of adapter-polynucleotide ligation products with an enzyme selected from: a polynucleotide kinase in the presence or in absence of ATP; a modified polynucleotide kinase derivative lacking 3'-end phosphatase activity in the presence of ATP; or in the absence of ATP and optional presence of ADP; an alkaline phosphatase; an RNA 5' monophosphatase; RNA 5' polyphosphatase; and a pyrophosphatase. The converting and/or circularizing may be performed in an order selected from: simultaneously in a single reaction mixture; sequentially in a single reaction mixture; sequentially in separate reaction mixtures; simultaneously in a single reaction mixture followed by an additional, separate circularization reaction; and simultaneously in a single reaction mixture, further comprising repeating circularizing in an additional, separate reaction mixture. The method may comprise depleting, separating, degrading, and/or blocking a remaining unligated combo adapter after said ligating to the sample polynucleotide and/or after said circularizing. The depleting, separating, degrading, or blocking a remaining unligated combo adapter may be performed in an order selected from: simultaneously in a single reaction mixture; sequentially in a single reaction mixture; and sequentially in separate reaction mixtures. The blocking group may comprise ligating the unligated combo adapter to a blocking oligonucleotide via either a splint-dependent or a splint-independent ligation reaction to prevent circularization and concatamerization of the combo adapter, wherein said blocking oligonucleotide optionally comprises at least one end blocking group to prevent its extension and ligation. The blocking may comprise hybridizing of the unligated combo adapter to a blocking oligonucleotide to prevent circularization and concatamerization of the combo adapter. The depleting may comprise hybridizing circular or concatameric forms of the unligated combo adapter with a capture oligonucleotide partially complementary to the junction between the 5' and 3' ends of the combo adapter and capture of the resulting hybridized circular or concatameric forms of the combo adapter on a solid support. The degrading may comprise hybridizing circular or concatameric forms of the unligated combo adapter with an oligonucleotide partially complementary to the junction between the 5' and 3' ends of the combo adapter and specific cleavage of its circular and concatameric forms by a cleaving agent guided by said oligonucleotide. The cleaving agent may be selected from: an RNase H, an RNase H II, a restriction endonuclease, duplex specific endonuclease, Cas9 nuclease, a ribozyme, deoxyribozyme or an artificial chemical nuclease. The blocking of the unligated combo adapter may comprise hybridizing circular or concatameric forms of said remaining unligated combo adapter with a blocking oligonucleotide partially complementary to the junction between the 5' and 3' ends of the combo adapter, wherein said blocking oligonucleotide prevents first primer extension and/or amplifying. The degrading may comprise degrading the unligated combo adapter before circularizing of the adapter-polynucleotide ligation product by an exonuclease. The circularizing may comprise splint-independent ligation of the 5' and 3' ends of said adapter-polynucleotide ligation product. The circularizing may comprise a splint-assisted ligation using a splint oligonucleotide complementary to both a 5'-end sequence of the sample polynucleotide and a 3'-end sequence of the adapter, wherein the 3' end sequence of the adapter allows selective amplification and sequencing only of target sample polynucleotide or complement thereof. The method may comprise degrading a non-circularized polynucleotide, non-circularized adapter or adapter-polynucleotide ligation product after circularizing. The first primer and second primer may be conventional primers comprising adapter-specific sequences. The first primer and second primer may be combo primers comprising adapter-specific sequences and an additional upstream (5'-end overhang) sequence, wherein the additional upstream sequence is selected from: a primer binding sequence; a restriction site, a sequencing bar-code or index, a Zip-code, one or more random nucleotides, a unique molecular identifier (UMI), flow-cell binding sites and combinations thereof. The extending and amplifying may be performed initially using the conventional primers, and then amplifying additionally using the combo primers. The extending and/or amplifying may be performed using a polymerase selected from: RNA-dependent DNA polymerase (reverse transcriptase), DNA-dependent DNA polymerase, DNA- and RNA-dependent DNA polymerase, DNA-dependent RNA polymerase, RNA-dependent RNA polymerase, DNA- and RNA-dependent RNA polymerase and combinations thereof. The method may comprise purifying the adapter-polynucleotide ligation product before said circularizing and, optionally, purifying an amplicon of the sequencing library. The method may allow for only a single round of primer extension on said circularized adapter-polynucleotide ligation product, thereby preventing rolling-circle amplification (RCA).

Disclosed herein are methods for detecting a sample polynucleotide in a sample comprising: ligating a combo adapter to the sample polynucleotide to produce an adapter-polynucleotide ligation product, wherein said combo adapter comprises a 5'-proximal segment and a 3'-proximal segment, and wherein at least one of the 5' proximal segment or 3' proximal segment comprises a sequencing adapter; circularizing said adapter-polynucleotide ligation product by ligating its 5' end to its 3' end to produce a circularized adapter-polynucleotide ligation product; hybridizing a first primer comprising a sequence at least partially complementary to the 5'-proximal segment of said combo adapter, to said circularized adapter-polynucleotide ligation product; extending said first primer with a polymerase to produce a monomeric nucleic acid that is complementary to the sample polynucleotide flanked by at least a portion of the sequencing adapter; amplifying said monomeric nucleic acid using said first primer and a second primer, wherein the sequence of the second primer is at least partially complementary to the 3'-proximal segment of said combo adapter; and sequencing the amplified monomeric nucleic acid or portion thereof, thereby detecting the sample polynucleotide.

Further disclosed herein are methods for detecting a sample polynucleotide in a sample comprising: ligating a combo adapter to the sample polynucleotide to produce an adapter-polynucleotide ligation product, wherein said combo adapter comprises a 5'-proximal segment and a 3'-proximal segment, and wherein at least one of the 5' proximal segment or 3' proximal segment comprises a sequencing adapter; circularizing said adapter-polynucleotide ligation product by ligating its 5' end to its 3' end to produce a circularized adapter-polynucleotide ligation product; hybridizing a first primer comprising a sequence at least partially complementary to the 5'-proximal segment of said combo adapter, to said circularized adapter-polynucleotide ligation product; extending said first primer with a polymerase to produce a monomeric nucleic acid that is complementary to the sample polynucleotide flanked by the sequencing adapter; amplifying said monomeric nucleic acid using said first primer and a second primer, wherein the sequence of the second primer is at least partially complementary to the 3'-proximal segment of said combo adapter; and detecting the amplified monomeric nucleic acid or portion thereof, thereby detecting the sample polynucleotide. The detecting may be performed by a method selected from: sequencing, microarrays, bead arrays, real-time qPCR, and digital PCR.

Provided herein are kits for preparing RNA sequencing libraries, wherein the kits comprise any one of the combo adapters disclosed herein. The RNA sequencing library may be a miRNA sequencing library. The RNA sequencing library may be a small RNA sequencing library. Also provided herein are kits for preparing DNA sequencing libraries, wherein the kits comprise the any one of the combo adapters disclosed herein.

BRIEF DESCRIPTION OF THE DRAWINGS

FIG. 1. Schemes to exemplify the ligation of variants of combo adapter (CAD) and polynucleotides.

FIG. 2. Schemes to exemplify circularization of the adapter-polynucleotide ligation product, also referred to as polynucleotide-CAD ligation product (PCAD).

FIG. 3. Schemes to exemplify the splint-assisted circularization of polynucleotide-CAD ligation products (PCAD). The splint oligonucleotide contains two segments, one of which can hybridize to a terminal segment of the target polynucleotide and the other to a terminal segment of CAD, bringing the polynucleotide and CAD ends together and allowing their sequence-specific ligation. Only the target polynucleotide will be circularized in these reactions and therefore included in the sequencing libraries, while non-target polynucleotides and free CAD will be excluded and not sequenced.

FIG. 4. Schemes to exemplify amplification of the circularized polynucleotide-CAD ligation products (circularized PCAD) to generate monomer amplicons. The circularized PCAD serves as a template for one round of primer extension by a polymerase (e.g., an RNA- and/or DNA-dependent DNA polymerase) so as to produce a monomeric complementary nucleic acid (cNA) rather than the multimeric products generated by rolling circle amplification (RCA). The 5'-proximal segment or a region between the 5'-proximal and 3'-proximal segments of CAD comprise at least one moiety that inhibits primer extension by a polymerase, thereby preventing rolling-circle amplification of the circularized PCAD. The sequence of the cNA is complementary to PCAD and contains sequences of both polynucleotide and CAD, where the polynucleotide inserted between the 5'- and 3'-proximal segments of the CAD.

FIG. 5. Schemes to illustrate use of a blocking oligonucleotide (BO) to prevent circularization and/or multimerization of free, unligated CAD. The terminal modifications shown at either one or both ends of the BO prevent its extension by polymerase and its ligation with the PCAD.

FIG. 6. Schemes to illustrate the depletion of circular or multimeric CAD sequences that are not ligated to the polynucleotide to prevent their amplification. Upon circularization of the polynucleotide-CAD ligation products (PCAD), any unligated CAD species may also be circularized or form multimeric concatamers and then serve as templates for synthesis of so-called "adapter dimers". Oligonucleotides complementary to the junction between the 5'- and 3'-end segments of CAD may specifically discriminate between the "empty" CAD sequences, which contain no polynucleotide inserts, and PCAD sequences in which the polynucleotide segment is inserted between the 5'- and 3'-segments of the CAD. The polynucleotide inserts reduce the affinity of such oligonucleotides for the PCAD. These oligonucleotides may be used to (further) reduce levels of any "empty" CAD sequences that were not completely blocked or depleted in the previous steps. FIG. 6B: General design of specific cleavage of circular and multimeric CAD by a cleaving agent guided or assisted by an oligonucleotide complementary to the junction between the 5'- and 3'-proximal segments of the CAD.

FIG. 8. Data to illustrate ligation of miRNAs with CAD (Example 1).

FIG. 9. Data to illustrate blocking free CAD allows selective circularization of miRNA-CAD ligation products (Example 2).

FIG. 10. Data to illustrate RT-PCR amplification of circular miRNA-CAD products (Example 3).

FIG. 11. Distribution of sequencing reads from sequencing libraries prepared using various methods from an equimolar pool of miRNAs (Example 4). The miRXplore™ Universal Reference pool (Miltenyi Biotec), which contains equimolar amounts of 962 synthetic miRNAs, was sequenced. Fold-changes between the sequencing reads mapped to individual miRNAs and their expected abundance were calculated assuming equimolar representation of miRNAs in the synthetic pool and plotted as $log_2$ values. The sequencing frequencies for miRNAs within a 2-fold deviation from the expected values (area between vertical lines) were considered as unbiased and plotted for the library preparation methods indicated.

FIG. 12. Distribution of sequencing reads from sequencing libraries for the miRXplore pool of miRNAs prepared using RealSeq® protocols using various circularization techniques (see Example 5).

DETAILED DESCRIPTION OF THE INVENTION

Figure 7:
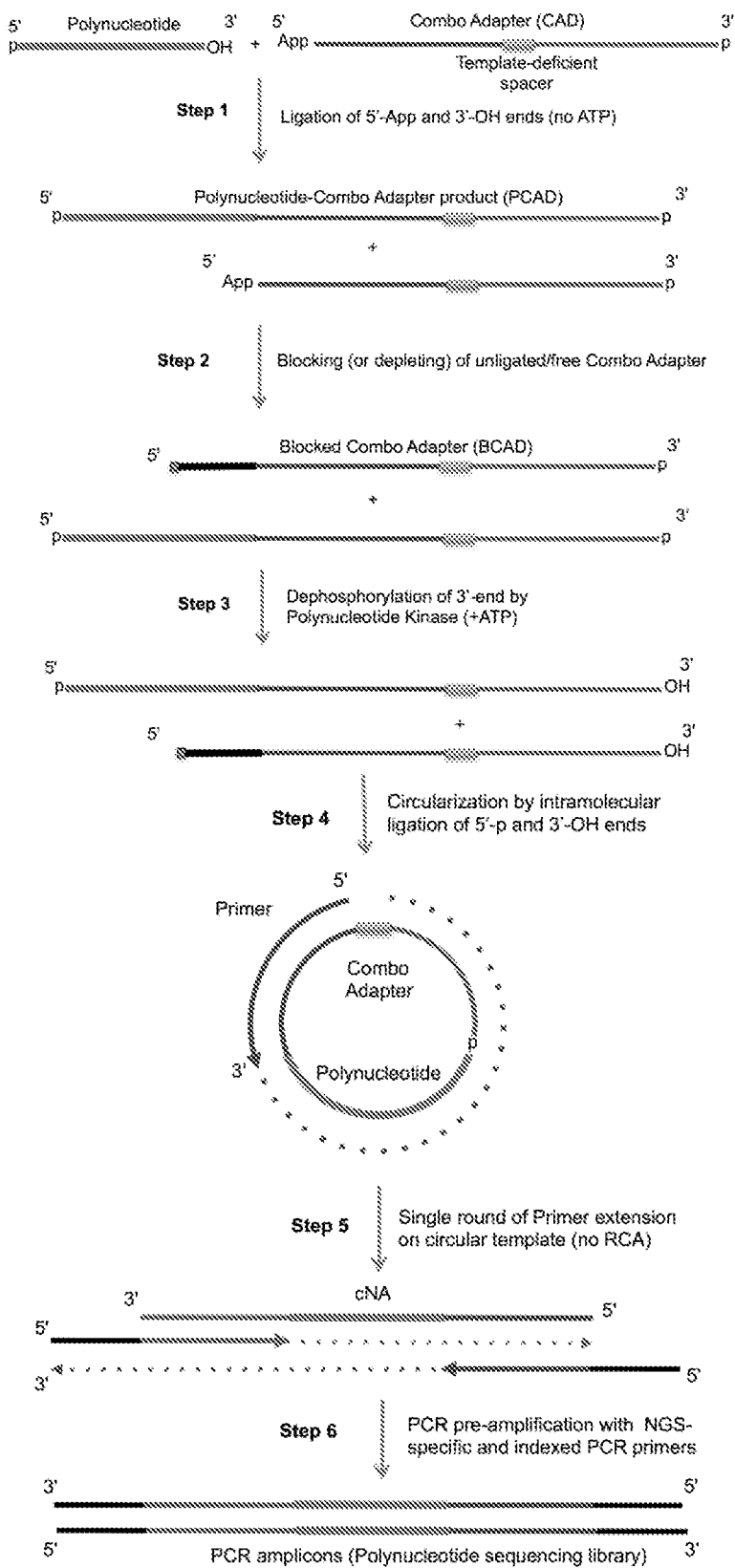
FIG. 7. Schemes to exemplify the preparation of polynucleotide sequencing libraries. Step 1: Ligation of a polynucleotide (RNA or ssDNA) having 5'-p and 3'-OH termini with a single combo adapter (CAD) at the 3'-end of the polynucleotide to form adapter-polynucleotide ligation products (PCAD) (see Example 1, wherein the polynucleotide is a miRNA). The CAD contains sequences of 3'- and 5'-adapters (in the 5'-proximal and 3'-proximal segments of the CAD, respectively) that are compatible with a current sequencing technology of choice (e.g., Illumina/Solexa sequencing). A template-deficient modification (e.g., a non-nucleotide spacer or linker) is inserted between the 5'- and 3'-adapter sequences. The CAD contains 5'-proximal DNA and 3'-proximal RNA segments and has 5'-adenylated (5'-App) and 3'-phosphate (3'-p) ends. The CAD's 3'-p end group is used as a reversible blocking group that prevents the adapter from circularizing or forming multimers. The ligation reaction is performed by a ligase that can ligate 5'-App and 3'-OH ends (3'-OH ligase) in the absence of ATP to prevent simultaneous circularization of polynucleotides, which would prevent their ligation with the CAD and, therefore, exclude the circularized polynucleotides from the sequencing library. Step 2: Blocking of free, non-ligated CAD (present in excess in Step 1) by ligation with blocking oligonucleotide(s) (see FIG. 5A-B and Example 2). A blocking oligonucleotide (BO, black) whose 5' end contains a non-ligatable group is ligated to CAD (but not PCAD), forming blocked CAD (BCAD), which will not be circularized in Step 4. Step 3: Activation or unblocking of the 3'-end of PCAD by dephosphorylation using Polynucleotide Kinase (PNK), which converts the non-ligatable 3'-p into ligatable 3'-OH end. Steps 2 and 3 may also be run simultaneously. Step 4: Circularization of the PCAD species by ligating their 5'-phosphate and 3'-OH RNA ends. The circularization reaction (Step 4) can be carried out using more than one ligase simultaneously in the same reaction mixture. Steps 3 and 4 may also be run simultaneously. The optional, additional circularization step can be performed under different reaction conditions using the same or different ligase(s), targeting PCAD that cannot be efficiently circularized in the single circularization step (see Example 2). The BCAD is not circularized due to its non-ligatable, blocked 5'-end and, therefore, is excluded from the polynucleotide sequencing library. Step 5: Primer extension on the circular PCAD template by a polymerase stops at the template-deficient modification(s) in the CAD after one round thus preventing rolling-circle amplification (RCA). This product of primer extension (cNA) comprises sequences complementary to PCAD and contains sequences of a single polynucleotide inserted between the sequencing adapters exactly in the same order as they appear in conventional methods of sequencing library preparation using ligation of two separate adapters to each polynucleotide ends. This first primer extension may be performed with either specialized primer (e.g. RT primer) or a reverse PCR primer, which may be used in the next step. Step 6: PCR pre-amplification of the cNA product with extended, barcoded combo PCR primers (see FIG. 4), yielding amplicons comprising the polynucleotide sequencing library that are ready for sequencing (see Example 3). Bead-based and/or gel-electrophoretic purification of these PCR amplicons allows selection of polynucleotide insert sizes in the range of interest.

Provided herein are methods and compositions for constructing libraries of polynucleotides. Further provided herein are methods and compositions for sequencing polynucleotides. These methods allow for the identification, detection, and quantification of small RNAs or fragments of larger RNAs, as well as the expression profiling of such RNAs in biological samples. In general these methods include ligating the small RNAs with a polynucleotide combo adapter (CAD) to generate adapter-polynucleotide ligation products (also referred to as polynucleotide-combo adapter products or PCAD), circularizing the PCAD, reverse transcribing the circular PCAD to generate a monomeric complementary nucleic acid, and amplifying the complementary nucleic acid. This process can be performed on multiple polynucleotides in a sample to produce a library that can be used either for detection or sequencing (sequencing library). The general steps of this process are illustrated in FIG. 7.

Accurate measurement of levels of individual microRNA (miRNAs) in biological samples is essential for development of miRNA biomarkers for cancer and other diseases as well as for understanding the biological roles of miRNAs. Next-generation sequencing (NGS) can be used for both detection and quantification of miRNAs. However, current NGS methods underestimate (by up to $10^4$-fold) the abundance of the majority of miRNAs. This bias results from drawbacks in the standard methods used to prepare small RNA sequencing libraries. These methods involve the sequential ligation of two sequencing adapters (3'-adapter to the RNA 3'-end and then 5'-adapter to the RNA 5'-end), followed by reverse transcription (RT) and PCR. The inefficient intermolecular ligation of the second adapter to the 5'-end of miRNAs by T4 RNA ligase 1 has been found to be responsible for most of the bias. In addition, a presence of large amounts of 5'-adapter-3'-adapter ligation products ("adapter-dimers"), which have no miRNA inserts, can dominate the sequencing reads (if not removed from or blocked during preparation of miRNA sequencing libraries) also may result in the under-detection of miRNAs by NGS. The sequencing bias problem for large RNAs that are fragmented to smaller pieces before sequencing (RNA-Seq) is similar to that for the naturally occurring smaller miRNAs. A recent study revealed the extremely low efficiency of standard methods of RNA-seq library preparation, which results in the loss of rare transcripts and alternatively spliced mRNAs that highlights the need for more efficient and less biased methods.

The methods and compositions as disclosed herein overcome the drawbacks of these methods by using a combo adapter (CAD) with both 5'-proximal and 3'-proximal segments wherein each segment comprises at least one sequencing adapter. This overcomes the need for two intermolecular ligation steps, thereby making the one-step intramolecular ligation of polynucleotide with a CAD to generate PCAD more efficient. Methods disclosed herein also overcome the underrepresentation of miRNAs that occurs during next generation sequencing by depleting, removing or blocking the unligated CAD to prevent adapter-dimers with no miRNA inserts from dominating the sequencing reads. The compositions and methods presented herein provide for minimal sequencing bias and significantly improve the quality of miRNA sequencing libraries. The compositions and methods disclosed herein achieve sensitive detection and accurate quantification of individual RNAs and fragments thereof.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range.

Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Certain Terminologies

Unless defined otherwise, all technical and scientific terms used herein have the same meaning as is commonly understood by one of skill in the art to which the claimed subject matter belongs. It is to be understood that the foregoing general description and the following examples are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 µL" means "about 5 µL" and also "5 µL." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value. A p-value of less than 0.05 is considered statistically significant.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of at least one symptom, diminishment of extent of disease, stabilized (e.g., not worsening) state of disease, delay or slowing of disease progression, amelioration or palliation of the disease state, and remission (whether partial or total), whether detectable or undetectable. Alternatively, treatment is "effective" if the progression of a disease is reduced or halted. Those in need of treatment include those already diagnosed with a disease or condition, as well as those likely to develop a disease or condition due to genetic susceptibility or other factors which contribute to the disease or condition, such as a non-limiting example, weight, diet and health of a subject are factors which may contribute to a subject likely to develop diabetes mellitus. Those in need of treatment also include subjects in need of medical or surgical attention, care, or management.

The terms "5'-proximal segment" and "3'-proximal segment" refer to independent parts of the combo adapters disclosed herein, wherein the 5'-proximal segment comprises the 5'-end of the combo adapter and the 3'-proximal segment comprises the 3'-end of the combo adapter, respectively, and wherein the 5'-proximal and 3'-proximal segments are linked to each other either by at least one nucleotide, internucleotide bond or non-nucleotide linker. The 5' proximal segment or the 3' proximal segment may be about one to about a hundred nucleotides long. In some embodiments, the 5' proximal segment or the 3' proximal segment are about 5 to about 70 nucleotides long. In some embodiments, the 5' proximal segment or the 3' proximal segment are about 15 to about 40 nucleotides long. In some embodiments, the 5' proximal segment or the 3' proximal segment are about 20 to about 27 nucleotides long. In some embodiments, the 5' proximal segment and the 3' proximal segment are of about the same length. In some embodiments, the 5' proximal segment and the 3' proximal segment are of the same length. In some embodiments, the 5' proximal segment and the 3' proximal segment are different lengths. In some embodiments, the 5' proximal segment or the 3' proximal segment consist of one nucleotide to 100 nucleotides. In some embodiments, the 5' proximal segment or the 3' proximal segment consist of 5 to 70 nucleotides. In some embodiments, the 5' proximal segment or the 3' proximal segment consist of 15 to 40 nucleotides. In some embodiments, the 5' proximal segment or the 3' proximal segment consist of 20 to 27 nucleotides.

The term "sequencing adapter" refers to nucleotide sequences which have to be added to one or both ends of a sample polynucleotide or its fragment in order for the sample polynucleotide or its fragment to be sequenced. Sequencing can occur either directly (without amplification) or after amplification using extended (combo) primers wherein either the sequencing adapter or extended primers comprise a primer binding site, a capture oligonucleotide binding site, a polymerase binding site, a sequencing barcode, an indexing sequence, at least one random nucleotide, a unique molecular identifier (UMI), sequencing flow-cell binding sites, and combinations thereof.

The term "combo primer" refers to a primer comprising at its 3' end a sequence [that is] specific (complementary or corresponding) to the 5'- or 3'-proximal segment of the CAD and has a 5'-end extension accommodating one or more additional sequences (e.g., sequencing index, bar-code, randomized sequence, unique molecular identifier (UMI), sequencing primer binding site or flow-cell binding site, or a combination thereof). The term "combo primer" may also be referred to herein as a "combo PCR primer," "combo reverse primer," "combo forward primer," and an "extended (combo) primer."

The term "detection sequences" refers to nucleotide sequences that allow a sample polynucleotide or its fragment to be detected either directly or after amplification, using detection techniques known in the art.

The terms "5'-end" and "3'-end" of a nucleic acid are standard terms of molecular biology known in the art, wherein these terms refer to the 5' and 3' carbons on the sugar terminal residues.

The term "template-deficient segment" refers to a segment of the combo adapter comprising at least one nucleotide, modified nucleotide, non-nucleotide residue or combination thereof, wherein the template-deficient segment is capable of restricting primer extension by a polymerase using combo adapter sequence as a template. Placing the template-deficient segment between combo adapter 5'-proximal and 3'-proximal segments or within 5'-proximal segment can stop the primer extension and, therefore, can prevent more than one round of primer extension (RCA) on the circular template comprising sequences of the adapter-polynucleotide ligation product or the combo adapter alone. The template-deficient segment may comprise at least one template-deficient nucleotide or template-deficient non-nucleotide residue. The template-deficient nucleotide or non-nucleotide residue may be at or near the 5' end of the template-deficient segment. The template-deficient nucleotide or non-nucleotide residue may be at or near the 3' end of the template-deficient segment. The template-deficient nucleotide may be a modified nucleotide, a derivatized nucleotide, a nucleotide analog, a DNA residue or a RNA residue. Said non-nucleotide residue is not chemically classified as nucleic acid residue, but can be synthetically inserted (serve as a linker) between nucleic acid residues. The template-deficient segment cannot serve as a template for nucleic acid synthesis. The template-deficient segment may prevent the synthesis of a nucleic acid strand complementary to a nucleic acid strand containing at least one template-deficient nucleotide or a template-deficient non-nucleotide residue at or beyond the site of the template-deficient nucleotide or a template-deficient non-nucleotide residue. The template-deficient nucleotide or non-nucleotide residue, which cannot be copied by a polymerase, may comprise at least one feature selected from: a) absence of a nucleic acid base (e.g., an abasic site or a non-nucleotide linker); b) a modified nucleic acid base lacking complementarity to the nucleotides accepted by a polymerase; c) a nucleotide or modified nucleotide that cannot be recognized by a polymerase (e.g., a ribonucleotide is not recognized by a DNA-dependent DNA polymerase, or a deoxyribonucleotide by an RNA-dependent DNA polymerase); and d) a modified nucleotide residue inhibiting activity of a polymerase by forming a chemical bond with said polymerase.

The term non-nucleotide residue refers to a residue that is not chemically classified as nucleic acid residue. The non-nucleotide residue may be synthetically inserted (serve as a linker or a spacer) between nucleic acid residues or be attached to nucleic acid ends (terminal groups). Examples of non-nucleotide residues include (but are not limited to): disulfide (S—S), 3' Thiol Modifier C3 S—S, a propanediol (C3 Spacer), a hexanediol (six carbon glycol spacer), a triethylene glycol (Spacer 9) and hexa-ethyleneglycol (Spacer 18).

The term "small RNA" generally refers to RNA or RNA fragments about 200 nucleotides or less. In some embodiments, the small RNA does not possess more than about 200 nucleotides. In some embodiments, the small RNA does not possess more than 200 nucleotides. In some embodiments, the small RNA does not comprise more than about 200 nucleotides. In some embodiments, the small RNA does not comprise more than 200 nucleotides. In some embodiments, the small RNA is not more than 200 nucleotides in length. In some embodiments, the small RNA is not more than about 200 nucleotides in length. In some embodiments, the small RNA does not consist of more than 200 nucleotides. In some embodiments, the small RNA does not consist of more than about 200 nucleotides. In some embodiments, the small RNA consists essentially of 200 nucleotides or less. In some embodiments, the small RNA consists essentially of about 200 nucleotides or less. In certain embodiments, the small RNA contain no more than 210 nucleotides, no more than 220 nucleotides, no more than 230 nucleotides, no more than 240 nucleotides, no more than 250 nucleotides, no more than 260 nucleotides, no more than 270 nucleotides, no more than 280 nucleotides, no more than 290 nucleotides, or no more than 300 nucleotides. As used herein, nucleotides of the small RNA are generally ribonucleotides. In some embodiments, the ribonucleotides may be chemically modified ribonucleotides.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods of Detecting Polynucleotides

Disclosed herein are methods for detecting a sample polynucleotide in a sample comprising: a) ligating a combo adapter (CAD) to the sample polynucleotide to produce an adapter-polynucleotide ligation product or polynucleotide-adapter ligation product (PCAD), wherein said combo adapter comprises a 5'-proximal segment and a 3'-proximal segment; b) optionally modifying the free, non-ligated combo adapter to prevent its circularization or specifically degrading it; c) circularizing said adapter-polynucleotide ligation product by ligating its 5' end to its 3' end to produce a circularized adapter-polynucleotide ligation product; d) optionally removing, depleting, or modifying circular and multimeric combo adapter species to prevent their amplification; e) hybridizing a first primer, comprising a sequence at least partially complementary to the 5'-proximal segment of said combo adapter, to said circularized adapter-polynucleotide ligation product) extending said first primer with a polymerase to produce a monomeric complementary nucleic acid (cNA) complementary to the sample polynucleotide flanked by at least a portion of the 3'- and 5'-proximal segments of combo adapter; g) amplifying said cNA using said first primer and a second primer, wherein the sequence of the second primer is at least partially complementary to the 3'-proximal segment of said combo adapter; h) detecting the monomeric nucleic acid or portion thereof, thereby detecting the sample polynucleotide. In some embodiments, the cNA consists of the sample polynucleotide flanked by at least a portion of the 3' and 5' proximal segments of the combo adapter. In some embodiments, the sample polynucleotide is directly flanked by at least a portion of the 3'- and 5'-proximal segments of combo adapter. In other words, the sample polynucleotide and 3'- and 5'-proximal segments may form a single contiguous sequence. In some embodiments, the sample polynucleotide is directly flanked by at least a portion of the 3'- and 5-sequencing adapter, thereby forming a single contiguous sequence.

The sample polynucleotide may be RNA. The sample polynucleotide may be DNA. The sample polynucleotide may be selected from: single-stranded RNA (RNA), double-stranded RNA (dsRNA), denatured dsRNA, single-stranded DNA (ssDNA), double-stranded DNA (DNA or dsDNA) or denatured double stranded DNA. The sample polynucleotide may comprise: a) a 5'-end group selected from: 5'-p; 5'-OH, 5'-ppp or other 5'-end group that may be converted to 5'-p, or 5'-OH or 5'-App; b) a 3'-end group selected from: a 3'-OH, or 3'-p, 2',3'-cyclic phosphate (2',3'>p) or 2'-phosphate (2'-p) that can be converted to 3'-OH, 3'-p, 2'-OH or 2'-p groups; and c) a 2'-group at its 3'-terminal residue selected from: 2'-H, 2'-OH, 2'-p or 2'-O-methyl (2'-OMe). Conversion of the 5'-end and/or 3'-end may be needed to allow the ligation of the sample polynucleotide to the combo adapter (FIGS. 1B, 1C and 1D) and/or to avoid circularization of the polynucleotides, which prevents the adapter ligation. Conversion of the 5'-end and/or 3'-end may be needed to allow circularization of the adapter-polynucleotide ligation product (FIG. 2B) and/or to avoid circularization of the combo adapter.

Figure 1A:
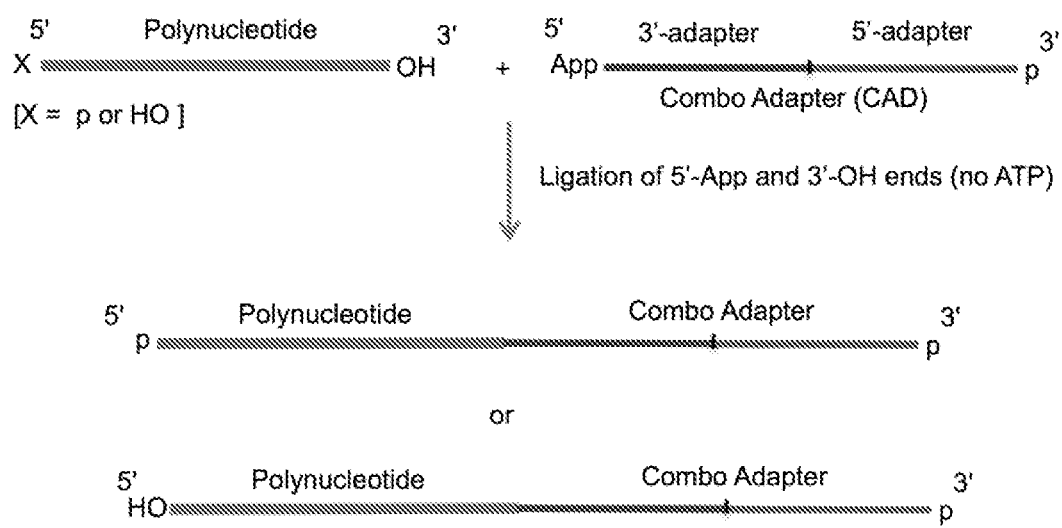
FIG. 1A: A polynucleotide having a 5'-p or 5'-OH and 3'-OH ends is ligated to the 5' end of a 3'-CAD having an adenylated 5' end (5'-App) and a 3'-terminal phosphate (3'-p). The ligation reaction is performed by an RNA and/or DNA ligase that ligates 5'-p/5'-App and 3'-OH ends (3'-OH ligase).
Figure 1B:
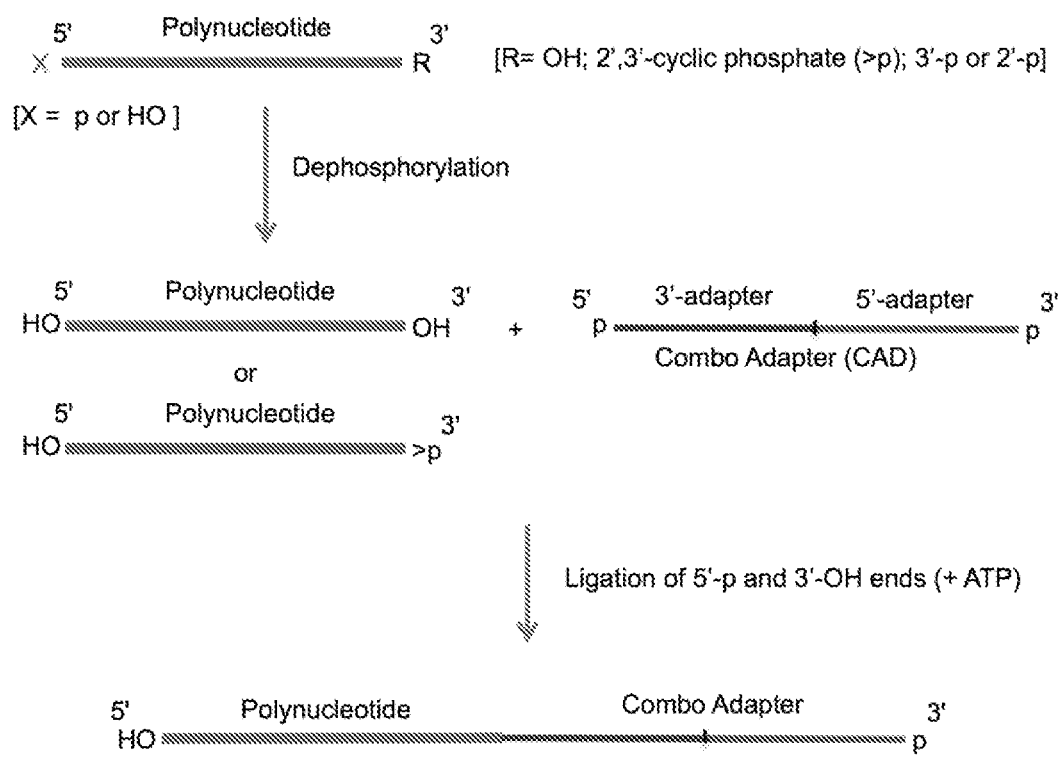
FIG. 1B: A polynucleotide having a 5'-p or 5'-OH and a phosphorylated 3'-end (e.g., 2',3'>p, or 3'-p, or 2'-p) or a 3'OH end is dephosphorylated, e.g. by Polynucleotide Kinase (PNK) in the absence of ATP, which converts the phosphorylated 3'-ends to 3'-OH and 5'-p to 5'-OH, or by an alkaline phosphatase, which removes all phosphates except 2',3'>p. A polynucleotide having 5'-OH and 3'-OH ends is then ligated to a 5' end of 3'-CAD having a 5'-p and a 3'-p ends. The ligation reaction is carried out by a 3'-OH ligase in the presence of ATP.
Figure 1C:
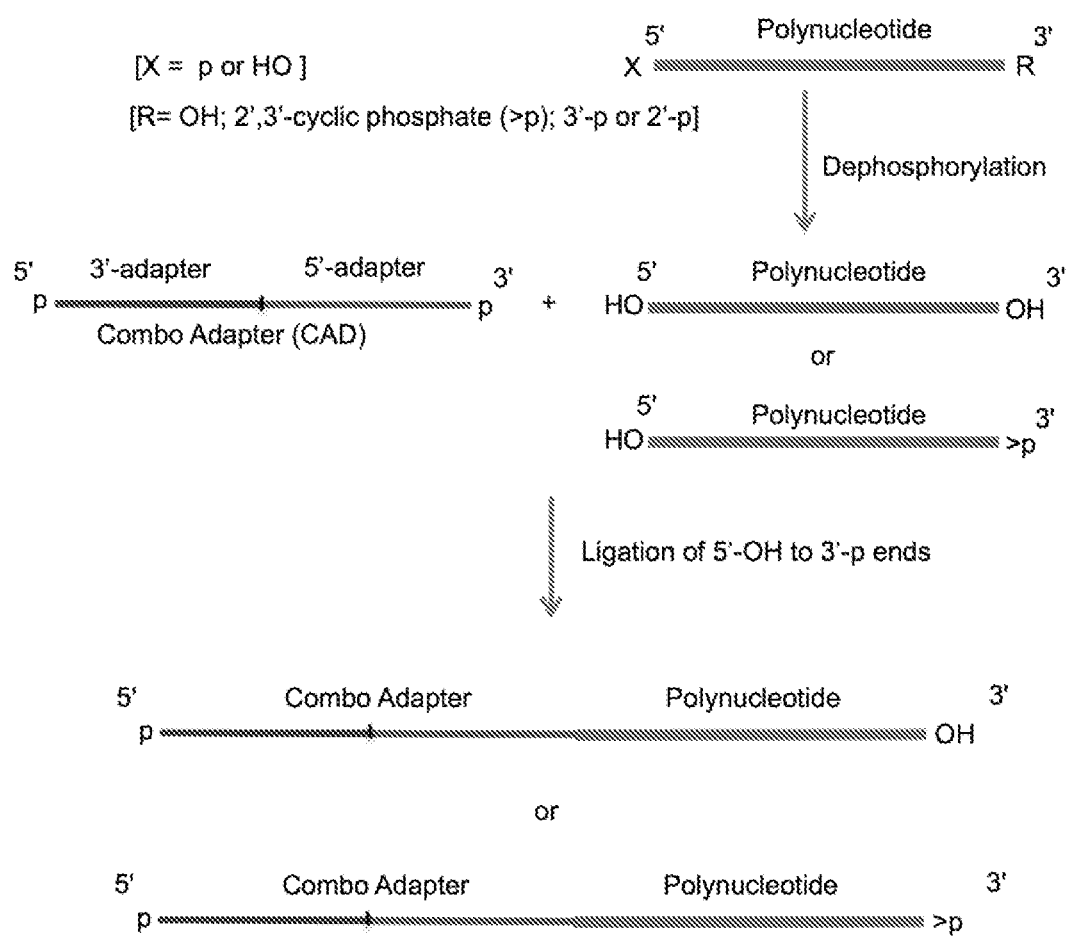
FIG. 1C: Same as FIG. 1B except that polynucleotide is ligated to 3' end of 5'-CAD by an RNA and/or DNA ligase that ligates 3'-p and 5'-OH ends (5'-OH ligase).
Figure 1D:
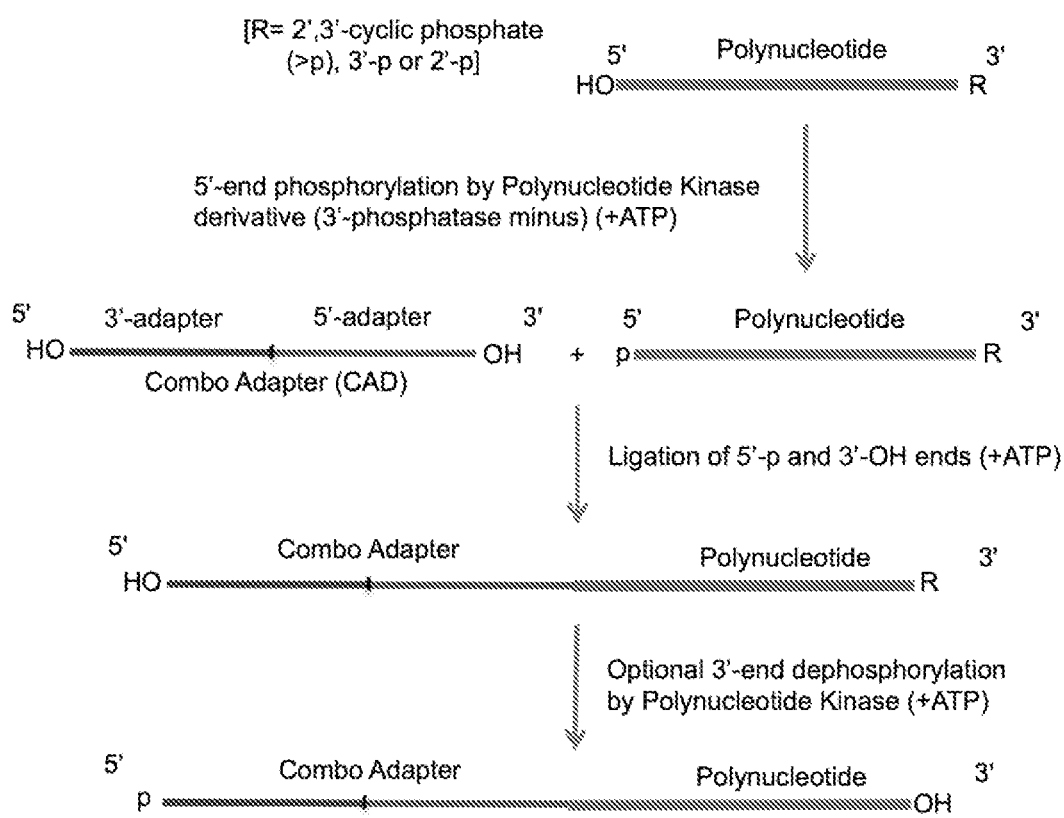
FIG. 1D: A polynucleotide having 5'-OH and phosphorylated 3'-end (e.g., 2',3'>p, or 3'-p, or 2'-p) is treated by a modified PNK derivative that lacks 3'-end phosphatase activity in the presence of ATP to convert its 5'-end to 5'-phosphate (but maintaining its phosphorylated 3' end) and then ligated to a 3' end of 5'-CAD having 5'-OH and 3'-OH ends by a 3'-OH ligase in the presence of ATP. Optional PNK treatment of the ligation product in the presence of ATP then converts the product ends into 5'-phosphate and 3'-OH.
Figure 1E:
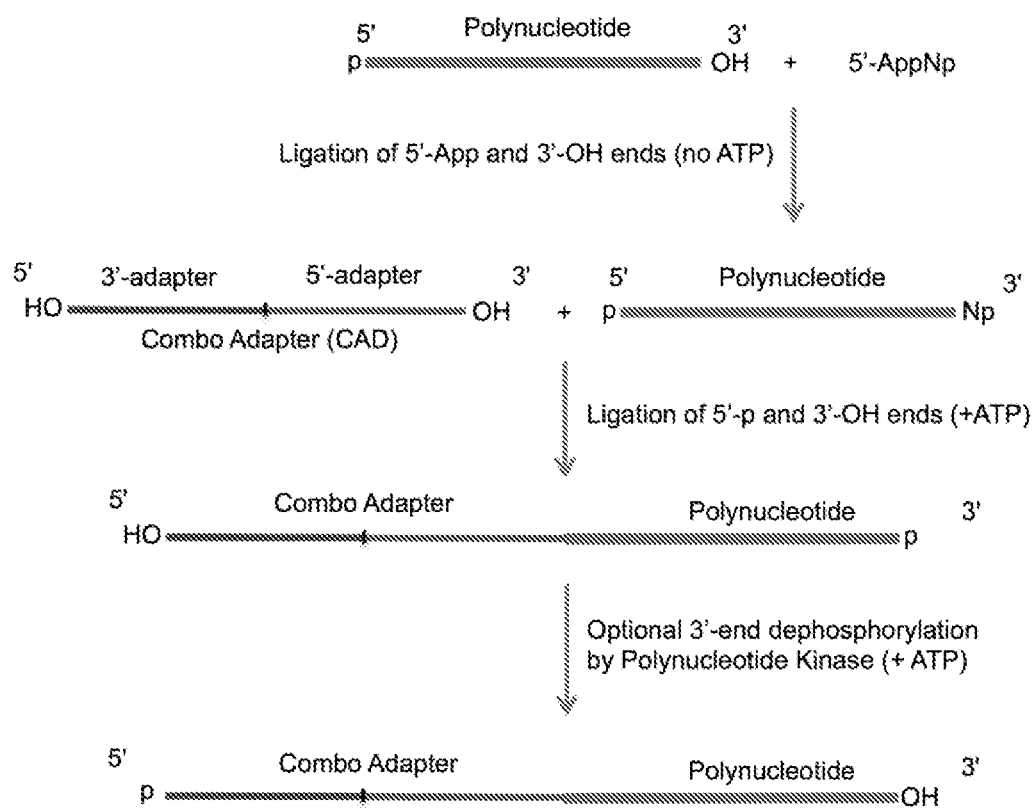
FIG. 1E: A polynucleotide having 5'-p and 3'-OH ends is first ligated to 5'-adenylated pNp (5'-AppNp), wherein N is ribonucleoside (e.g., Cytidine, pCp), by a 3'-OH ligase in the absence of ATP to add a 3'-p at the 3' end of the polynucleotide, followed by ligation of the polynucleotide to a 5'-CAD having 5'-OH and 3'-OH ends by a 3'-OH ligase in the presence of ATP, optionally followed in turn by PNK treatment as described in FIG. 1D.
Figure 2A:
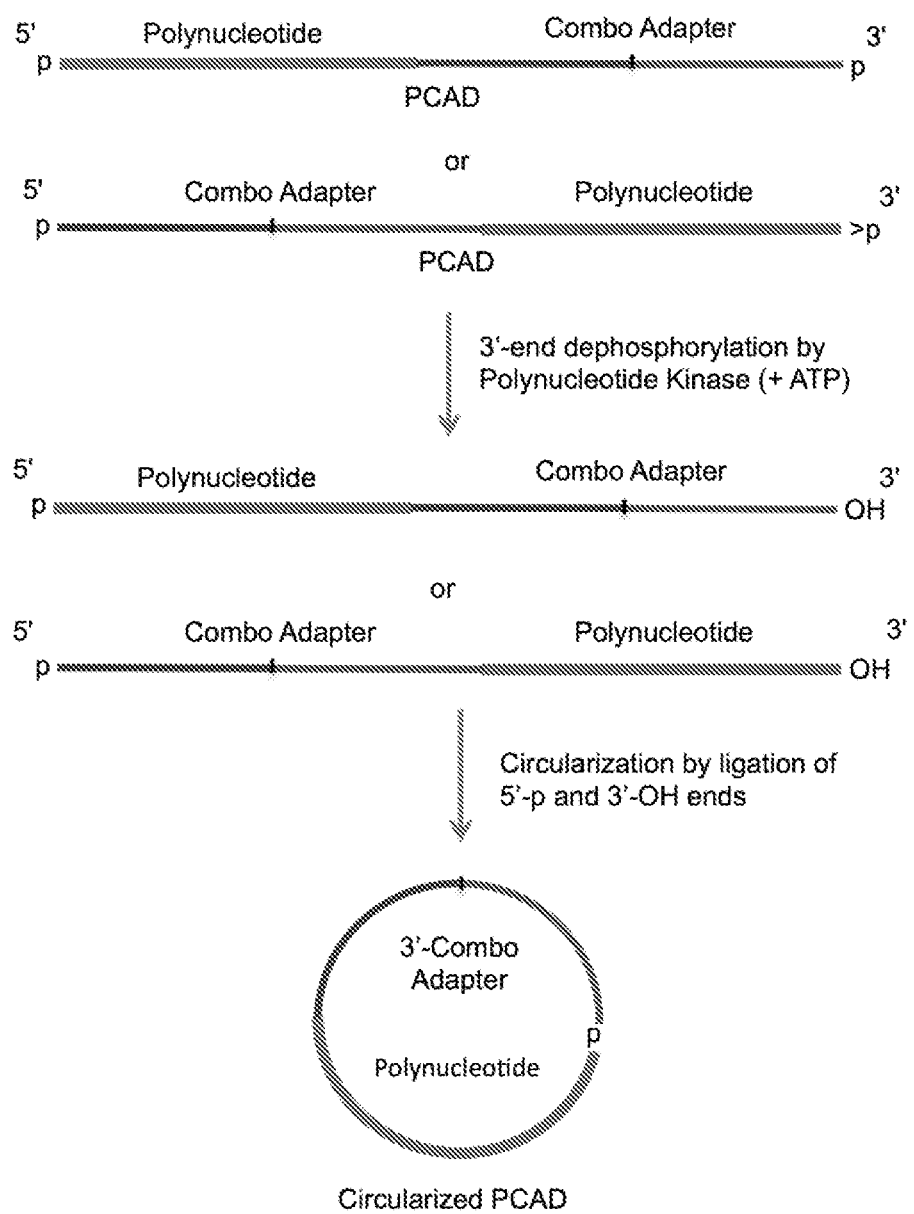
FIG. 2A: A PCAD having 5'-p and phosphorylated 3'-ends (e.g., 3'-p from FIG. 1A or 2',3'>p from FIG. 1C) is treated by a PNK in the presence of ATP to convert the phosphorylated 3' end to 3'-OH (but maintaining its 5'-p end) and then circularized by a 3'-OH ligase.
Figure 2B:
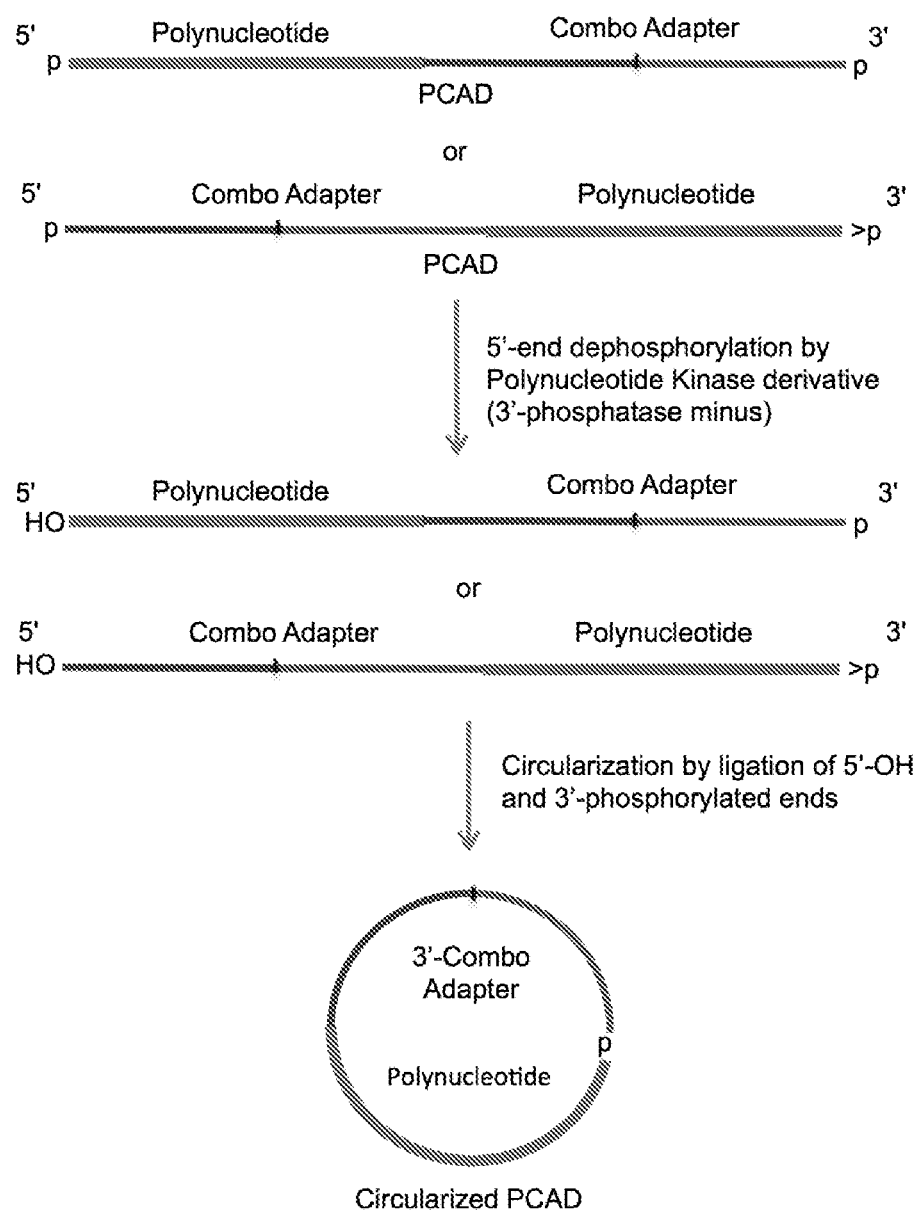
FIG. 2B: The same PCAD as in FIG. 2A is treated by a modified PNK derivative that lacks 3'-end phosphatase activity in the absence of ATP (and optional presence of ADP) to convert their 5'-p end to 5'-OH (but maintaining its phosphorylated 3'-p end) and then circularized by a 5'-OH ligase.

Ligating the combo adapter (CAD) to the sample polynucleotide may comprise ligating the combo adapter to the 3' end of the sample polynucleotide. Ligating the combo adapter to the sample polynucleotide may comprise ligating the combo adapter to the 5' end of the sample polynucleotide. Said ligating may be carried out by an RNA and/or DNA ligase that ligates 5'-p/5'-App and 3'-OH ends ("3'-OH ligase"). The 3'-OH ligase may be selected from: T4 RNA ligase, T4 RNA ligase 1 (Rnl1), T4 RNA ligase 2 (Rnl2), Mth RNA Ligase, CircLigase™ ssDNA ligase, CircLigase™ II ssDNA ligase, CircLigase™ RNA Ligase, and Thermostable 5' AppDNA/RNA ligase. Alternatively, said ligating may be carried out by an RNA and/or DNA ligase that ligates 3'-phosphorylated and 5'-OH ends (5'-OH ligase). The 3'-phosporylated group may be selected from: a 3'-3'-p, 2'-p or 2',3'-cyclic phosphate (2',3'>p or >p). The 5'-OH ligase may be selected from: RNA-splicing ligase (RtcB), *A. thaliana* tRNA ligase (AtRNL), tRNA ligase enzyme (Trl1), and tRNA ligase (Rlg1). A combo adapter comprising 5'-App and 3'-p end groups may be ligated to the 3' end of a sample polynucleotide comprising 5'-p or 5'-OH and 3'-OH end groups by a 3'-OH ligase in the absence of ATP (FIG. 1A). A combo adapter comprising 5'-p and 3'-p end groups may be ligated to the 3' end of a sample polynucleotide comprising 5'-OH and 3'-OH end groups by a 3'-OH ligase in the presence of ATP (FIG. 1B). A combo adapter comprising 5'-p and 3'-p end groups may be ligated to the 5' end of a sample polynucleotide comprising 5'-OH and 3'-OH or 2',3'>p end groups by a 5'-OH ligase (FIG. 1C). A combo adapter comprising 5'-OH end group and 3'-OH end group may be ligated to the 5' end of a sample polynucleotide comprising 5'-p and 3'-phosphorylated end groups by a 3'-OH ligase in the presence of ATP (FIGS. 1C and 1E). Said 3'-phosphorylated end groups may include: 3'-p, 2'-p, 2',3'>p or combinations thereof. After the ligation of a combo adapter to a sample polynucleotide, the 5'-end and/or 3'-end groups of the resulting adapter-polynucleotide ligation products may need to be converted to allow the circularization (FIG. 2A-B). In other embodiments, the 5'- and/or 3'-end groups of the said adapter-polynucleotide ligation products may directly allow the circularization (FIG. 2C).

In the ligation reaction with sample polynucleotides, the combo adapter is usually present in excess to maximize the ligation efficiency. Upon said circularizing of the adapter-polynucleotide ligation product, the unligated combo adapter may also be circularized or may form multimeric sequences (concatamers) that can serve as templates for synthesis of so-called "adapter dimers". The amplified adapter dimers comprising the sequencing adapters without polynucleotide insert may saturate the sequencing reads and reduce the number of polynucleotide sequencing reads, especially at low levels of input polynucleotides. In some embodiments, the 5'-end and/or 3'-end groups of the combo adapter may contain a blocking group that prevents or reduces its circularization while allowing circularization of the said adapter-polynucleotide ligation products. The 3'-p end group may prevent the circularizing of the combo adapter by 3'-OH ligase, whereas 5'-p and 5'-App end groups may prevent the circularizing of the combo adapter by 5'-OH ligase. Some embodiments may comprise using a 3'-OH ligase for ligating a combo adapter to a sample polynucleotide and then using a 5'-OH ligase to circularize the adapter-polynucleotide ligation product, or alternatively using a 5'-OH ligase for ligating a combo adapter to a sample polynucleotide and then using a 3'-OH ligase to circularize the adapter-polynucleotide ligation product to prevent or reduce circularization of the combo adapter.

The converting and/or circularizing may be performed in a manner selected from: a) simultaneously in a single reaction mixture; b) sequentially in a single reaction mixture; c) sequentially in separate reaction mixtures; and d) simultaneously in a single reaction mixture followed by an additional, separate circularization reaction. The converting and circularizing may occur simultaneously in a single reaction mixture, further comprising repeating circularizing in an additional, separate reaction mixture. In some embodiments, said converting and circularizing may be performed simultaneously in the same reaction mixture by polynucleotide kinase (PNK) and an RNA ligase selected from T4 RNA ligase, T4 RNA ligase 1 (Rnl1) and T4 RNA ligase 2 (Rnl2), respectively.

Figure 2C:
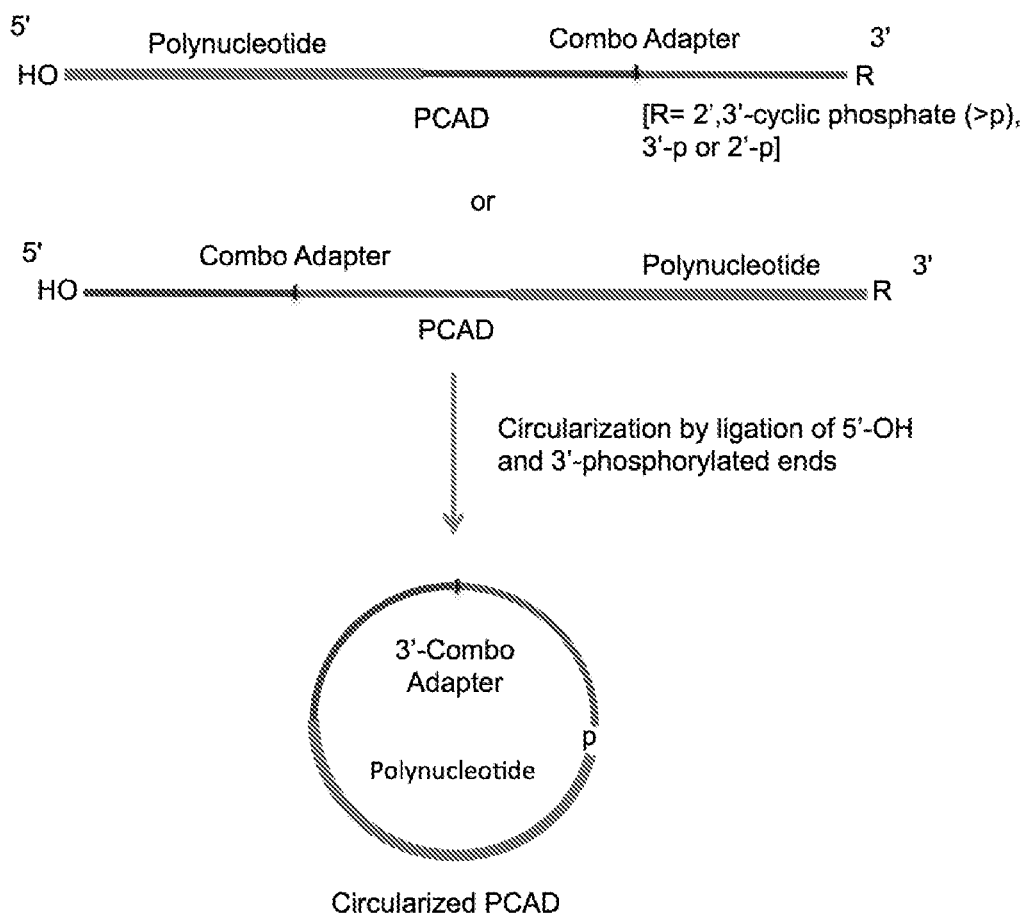
FIG. 2C: A PCAD having 5'-OH and phosphorylated 3'-end (e.g., 3'-p from FIG. 1A-1B or 2',3'>p from FIG. 1D) is directly circularized by a 5'-OH ligase.
Figure 3A:
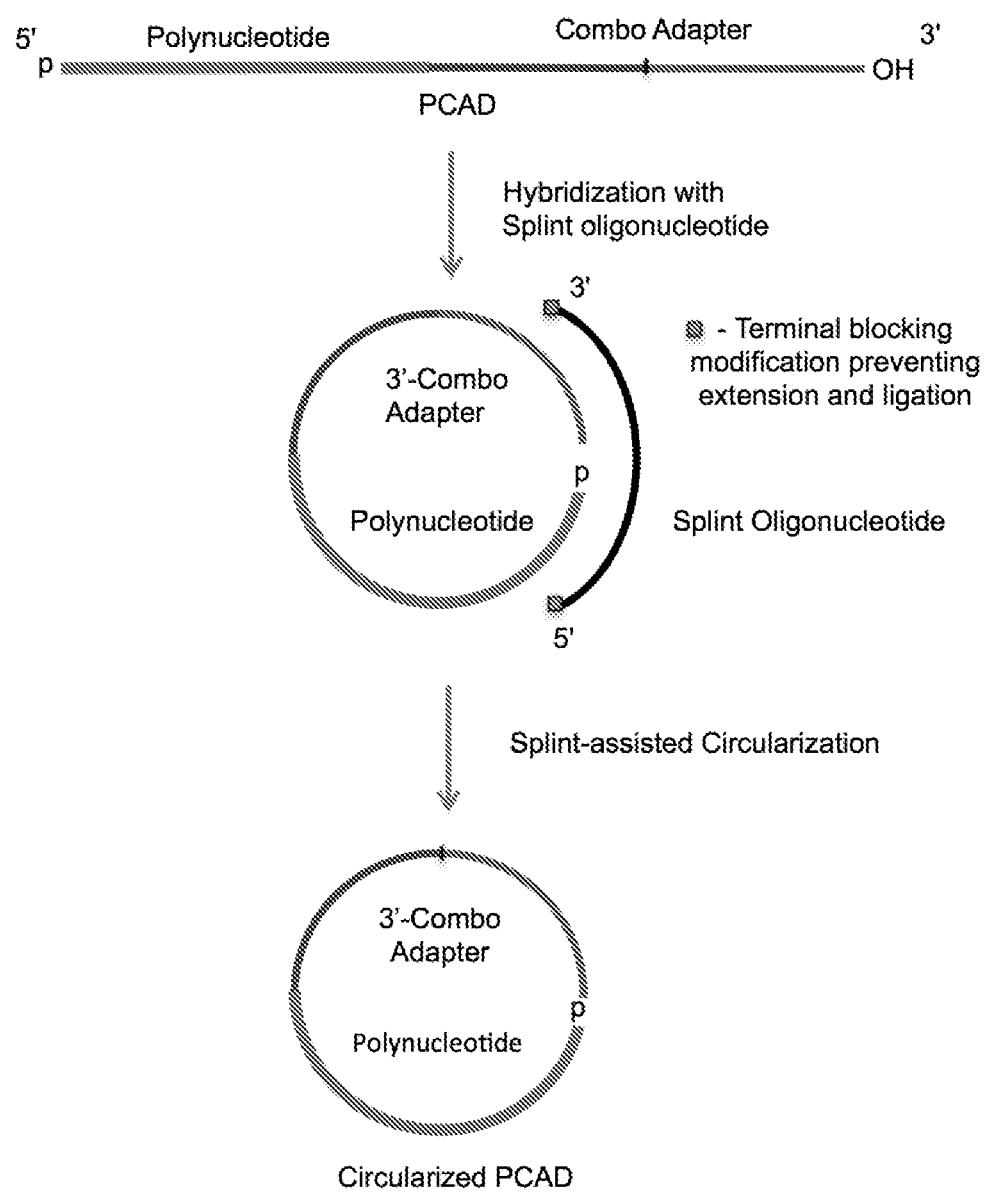
FIG. 3A: Circularization of the ligation product of the target polynucleotide with a 3'-CAD using a splint oligonucleotide having a 3'-end modification that prevents its extension in the subsequent RT reaction.
Figure 3B:
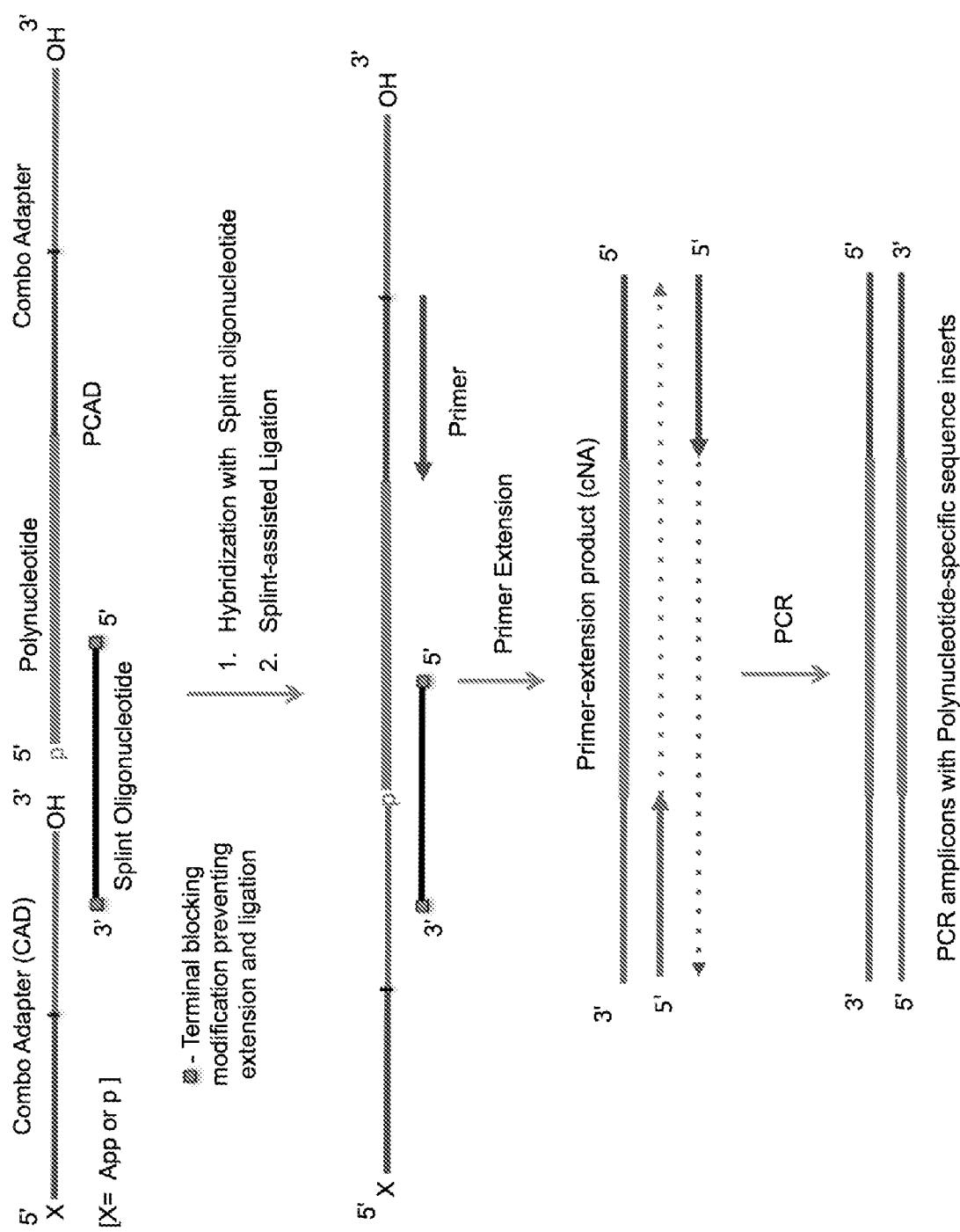
FIG. 3B: A potential alternative reaction to the circularization (intramolecular ligation) step described in FIG. 3A. If unligated CAD present in excess of polynucleotide during ligation steps (see FIG. 2) is not blocked before circularization of the PCAD, an alternative reaction may result in the intermolecular splint-assisted ligation of a second 3'-CAD to the PCAD, generating a linear template with the polynucleotide inserted between the 5'- and 3'-adapter sequences that is suitable for generating the same sequencing library as for the circular PCAD.
Figure 3C:
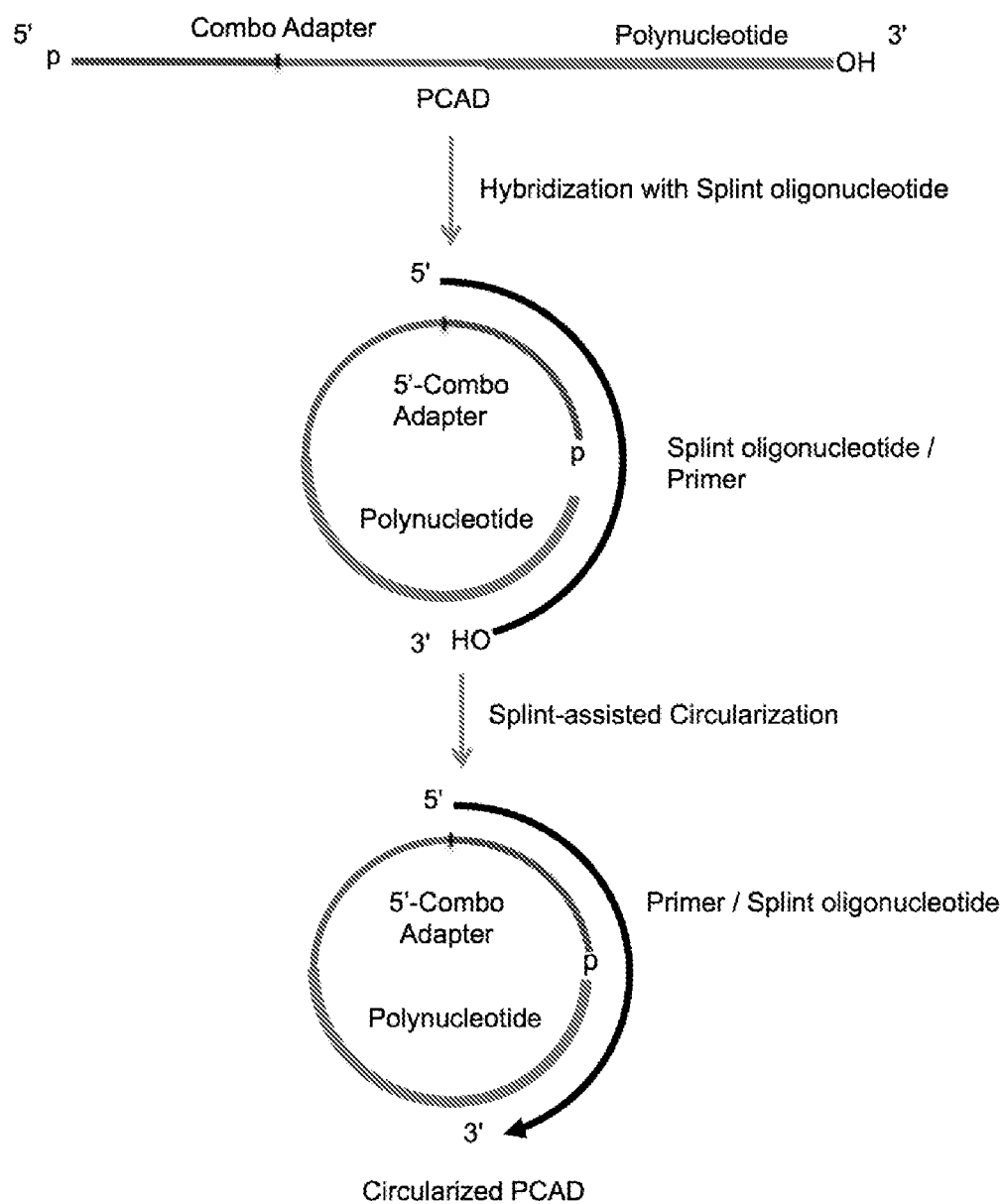
FIG. 3C: Circularization of the ligation product of the polynucleotide with a 5'-CAD using a splint oligonucleotide with unblocked 3'-OH end, which allows its use as a primer for extension in the downstream RT reaction (see FIG. 4). For the sequencing library preparation, the 5'-proximal end segment of this splint oligonucleotide may be fully complementary to 5'-proximal segment of CAD.
Figure 3D:
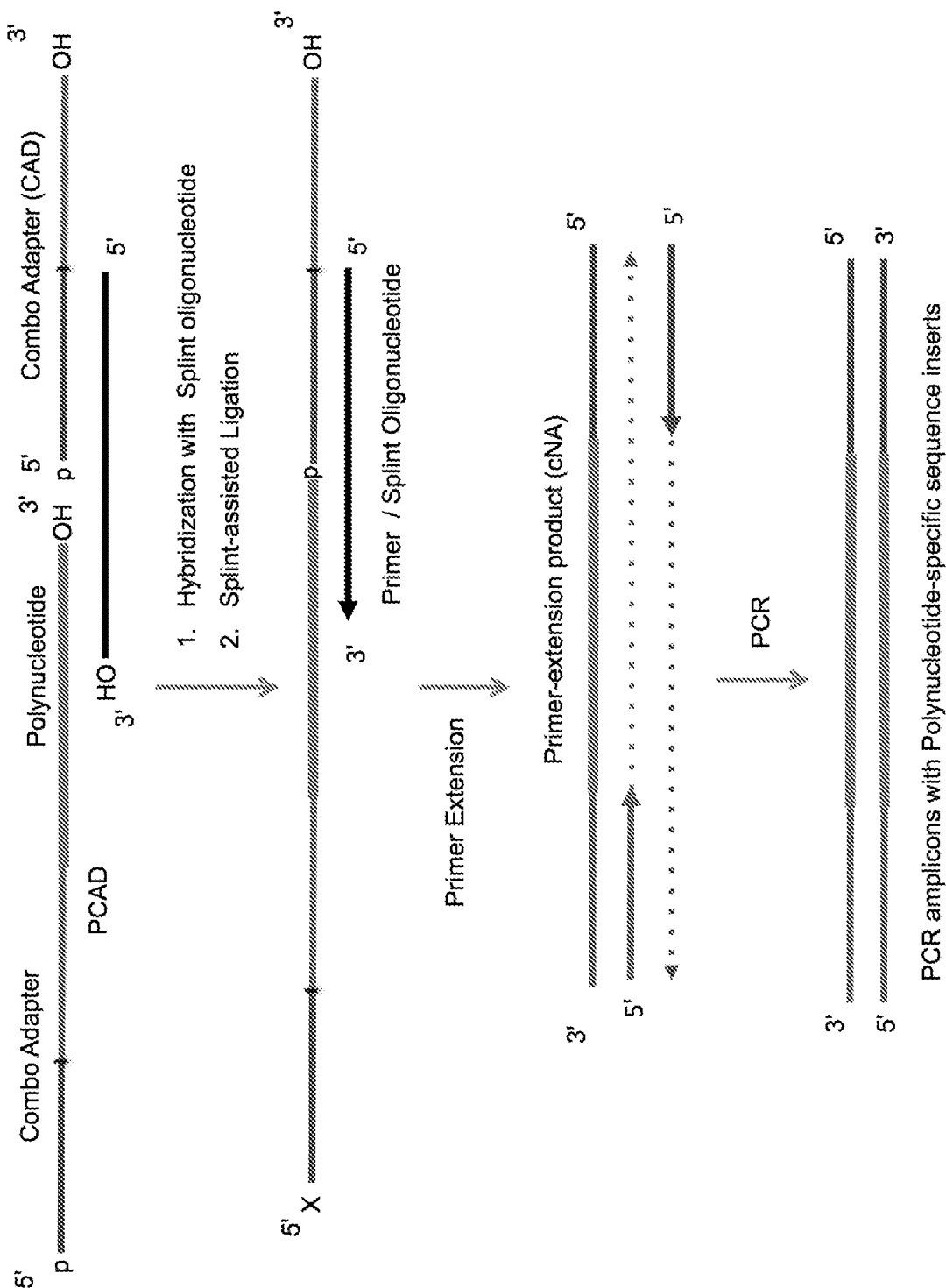
FIG. 3D: A potential alternative reaction for the circularization described in FIG. 3C. This alternative reaction results in the splint-assisted ligation of a second 5'-CAD to the polynucleotide-CAD ligation product generating a linear template, with the polynucleotide inserted between the 5'- and 3'-proximal segments of the CAD, suitable for generating the sequencing library by RT-PCR.

Circularizing may comprise splint-independent ligation of the 5' and 3' ends of the adapter-polynucleotide ligation product (FIG. 2). The circularizing by splint-independent ligation may be performed by a 3'-OH ligase (FIG. 2A) selected from: T4 RNA ligase, T4 RNA ligase 1 (Rnl1), T4 RNA ligase 2 (Rnl2), Mth RNA Ligase, CircLigase™ ssDNA ligase, CircLigase™ II ssDNA ligase, CircLigase™ RNA Ligase, and Thermostable RNA ligase. The circularizing by splint-independent ligation may be performed by a 5'-OH ligase (FIG. 2B-C) selected from: RNA-splicing ligase (RtcB), *A. thaliana* tRNA ligase (AtRNL), tRNA ligase enzyme (Trl1), and tRNA ligase (Rlg1).

The ligating of a combo adapter to a sample polynucleotide and circularizing of the adapter-polynucleotide ligation product may be performed by a splint-assisted (or splint-dependent) ligation using a splint oligonucleotide (FIG. 3). The splint oligonucleotide may have a terminal blocking group at its 3' end and (optionally) at its 5' end to prevent its extension and ligation (FIG. 3A-B). Alternatively, the splint oligonucleotide may have 3'-OH end extendable by a polymerase and also serve as a primer (FIG. 3C-D). The splint oligonucleotide contains two segments, wherein one segment is complementary to at least part of the combo adapter and another segment is complementary to at least part of the target sample polynucleotide, bringing the polynucleotide and combo adapter ends together and allowing their ligation. The splint-assisted ligation may be performed by a 3'-OH ligase selected from: T4 RNA ligase 2, SplintR™/PBCV-1 or T4 DNA ligase. The splint-assisted ligation may allow target or targeted sequencing and reduce (or eliminate) an adapter-dimer formation. Because only the target sample polynucleotide(s) will be ligated and/or circularized by the splint-dependent ligations and therefore included in the sequencing libraries, all other (non-target) sample polynucleotides and free (unligated) combo adapter will be excluded from the library and, therefore, not sequenced.

The ligating and circularizing steps may be performed using more than one ligase simultaneously in the same reaction mixture. The optional, additional ligation and/or circularization step can be performed under different reaction conditions using the same or different ligase(s) if some adapter and/or polynucleotides cannot be efficiently ligated or circularized in the single circularization step.

Ligating and/or circularizing may occur in the absence of ATP. Ligating and/or circularizing may occur in the presence of cofactors selected from: ATP, GTP, $Mg^{2+}$, $Mn^{2+}$ or combinations thereof. Since circularization of the adapter-polynucleotide ligation product via intramolecular ligation is more efficient than intermolecular ligation of the 5'-adapter in standard two-adapter ligation methods, the circularization-based approach may provide reduced ligation bias and higher yield of the sequencing libraries.

Provided herein are methods, wherein the methods allow for only a single round of primer extension, thereby preventing rolling circle amplification. By limiting the method to a single round of primer extension, the methods disclosed herein provide several advantages. One advantage is the generation of standard-length PCR amplicons directly compatible with next generation sequencing. Another advantage is reduced sequencing bias for sample polynucleotides varying in sequence and length since these various polynucleotides can be amplified by RCA with different efficiency.

Figure 4A:
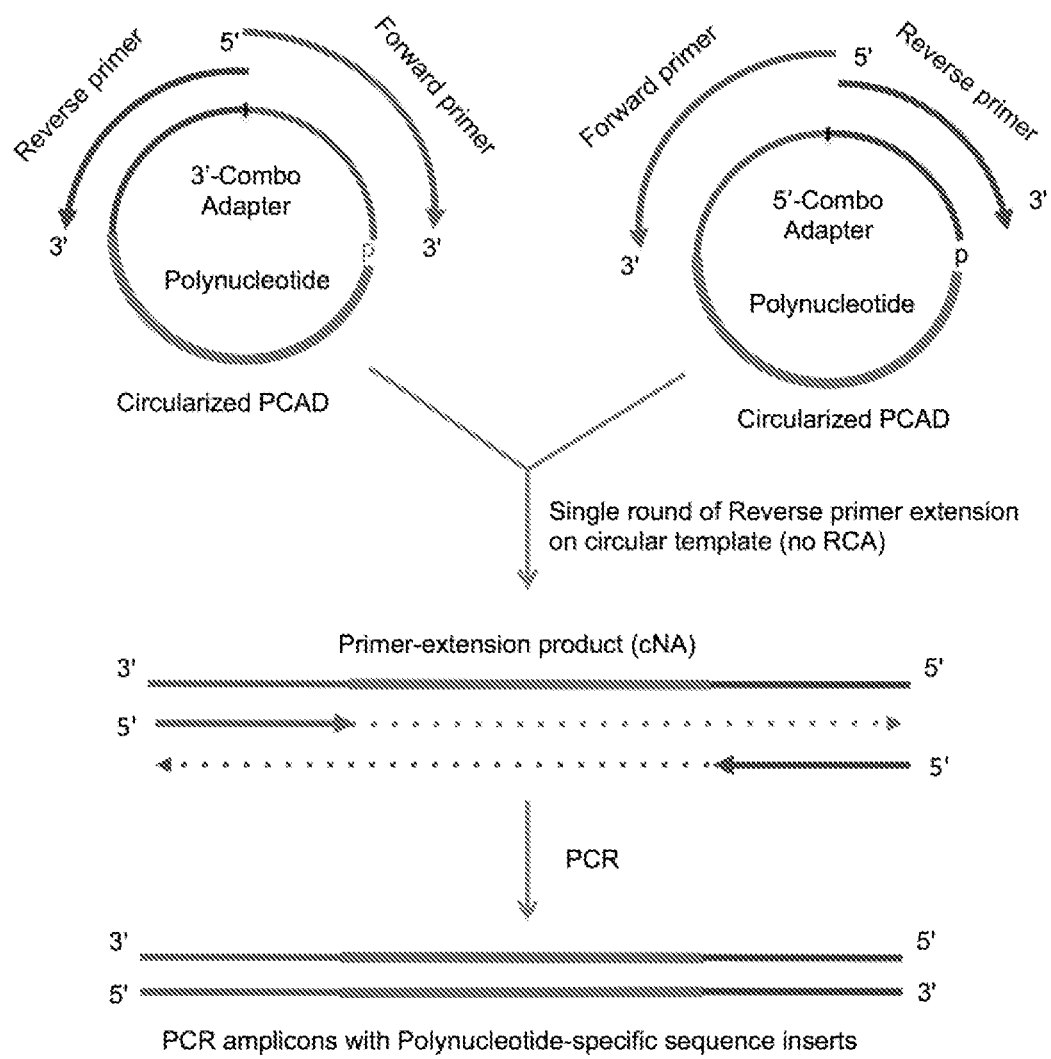
FIG. 4A: Primer extensions on the circularized PCAD with standard primers complementary or corresponding to the 5'- and 3'-proximal segments of the CAD.
Figure 4B:
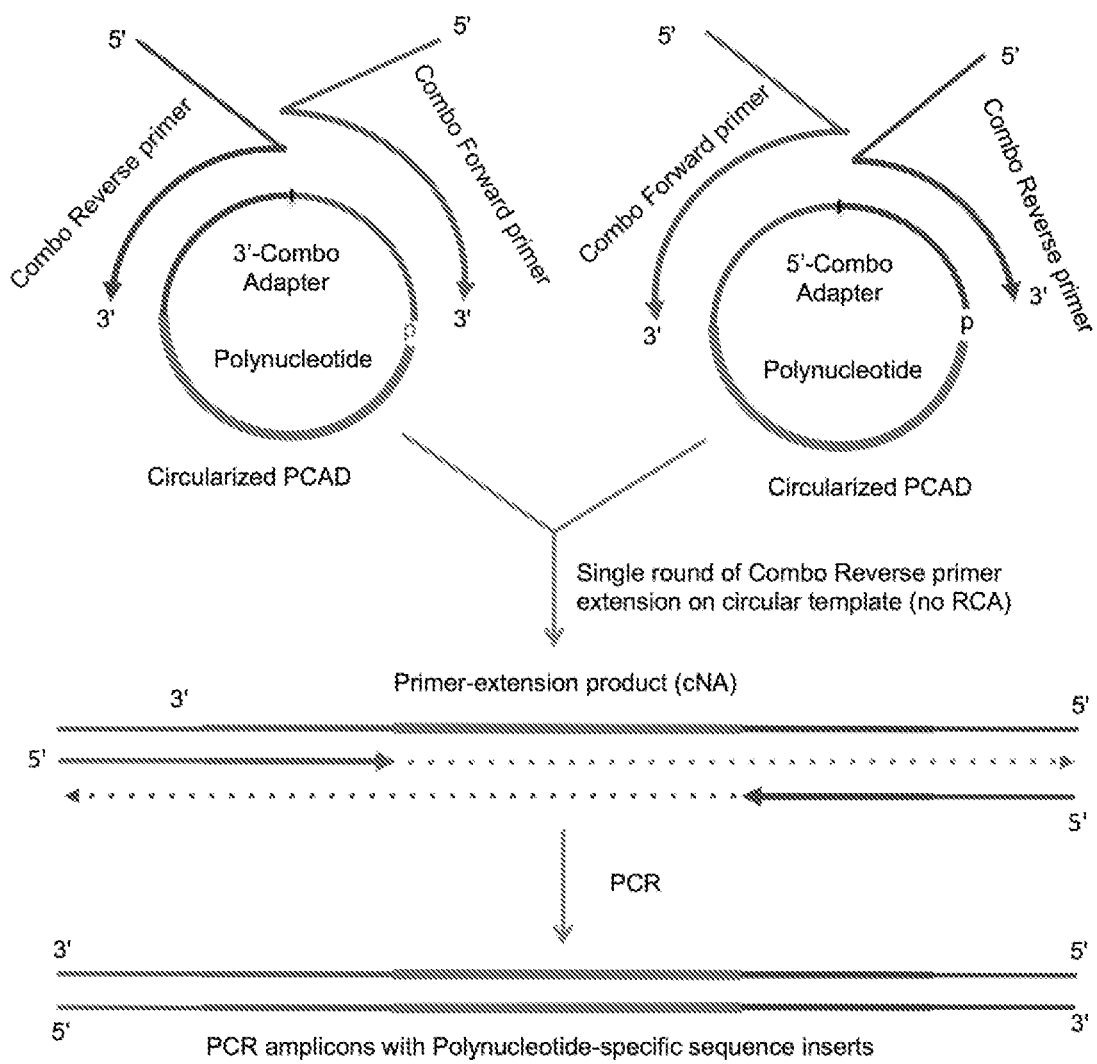
FIG. 4B: Primer extensions with combo primers complementary or corresponding to the 5'- and 3'-proximal segments of the CAD and also containing 5'-overhangs accommodating additional sequences (e.g., sequencing indexes, bar-codes, randomized sequences, unique molecular identifiers (UMI), sequencing primer binding sites or flow-cell binding sites or combinations thereof).
Figure 4C:
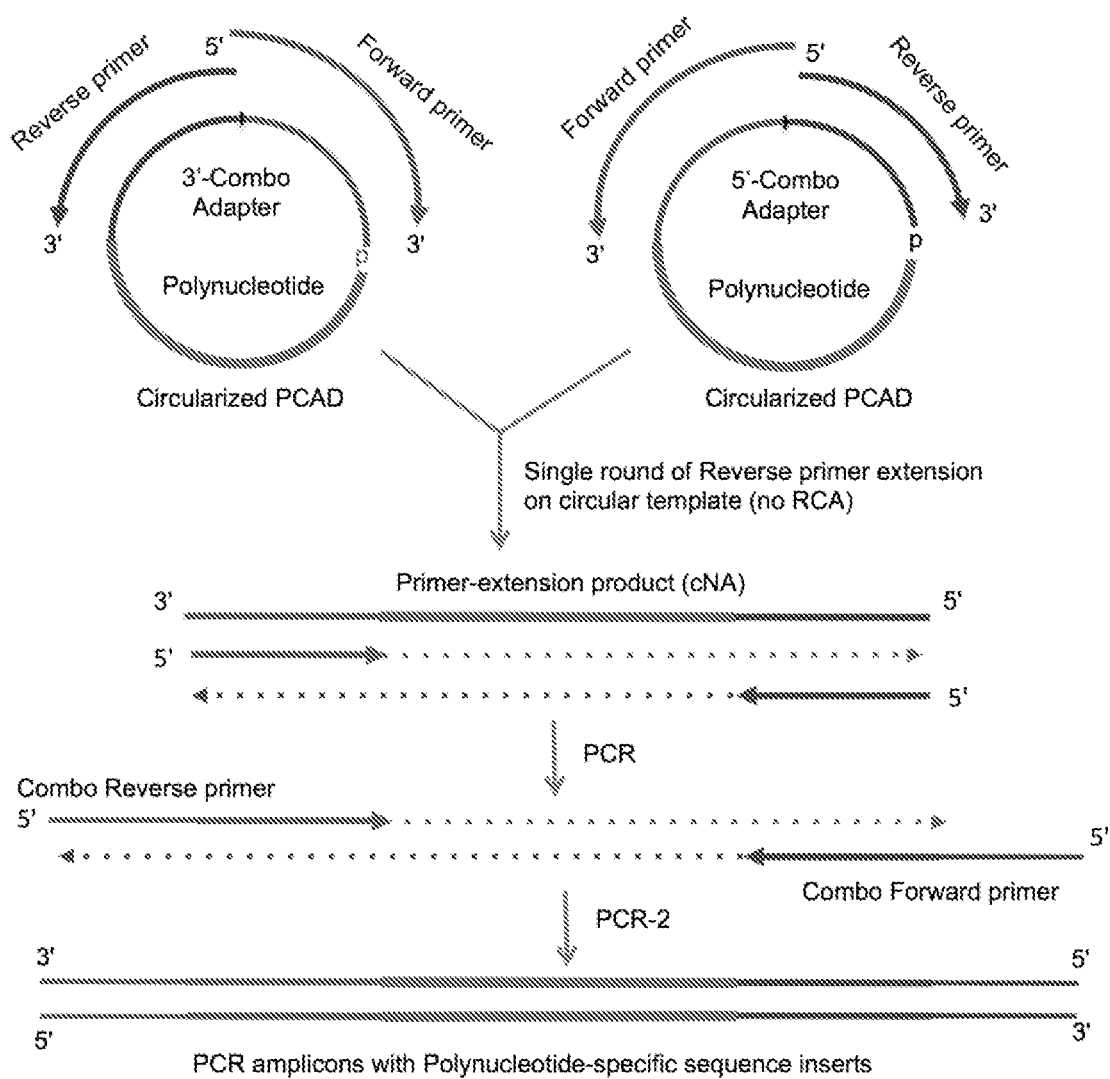
FIG. 4C: A combination of schemes shown in FIG. 4A-4B, where the initial amplification is performed using shorter, conventional primers whereas the second PCR amplification step (PCR-2) is performed using the combo PCR primers.

The circularized adapter-polynucleotide ligation products may serve as a template for one round of primer extension by a polymerase so as to produce a monomeric complementary nucleic acid (cNA) rather than the multimeric products generated by rolling circle amplification (RCA) (FIG. 4). Said polymerase may be a DNA polymerase selected from: RNA-dependent, DNA-dependent, or DNA- and RNA-dependent polymerase. Said polymerase may be an RNA polymerase selected from: RNA-dependent, DNA-dependent, or DNA- and RNA-dependent polymerase. The 5'-proximal segment, or a region between the 5'-proximal and 3'-proximal segments of combo adapter, may comprise a template-deficient segment or at least one modified moiety that stops primer extension by a polymerase, thereby preventing RCA. The sequence of said cNA comprises the complement of the polynucleotide sequence flanked by the complements of at least a portion of the 5'- and 3'-proximal segments of the combo adapter. The primer extensions may be performed using conventional, the first and second primers specific for the 5'- and 3'-proximal segments of combo adapter (FIG. 4A). The first and second primers may each be combo primers comprising adapter-specific sequences and an additional upstream (5'-end overhang) sequence (FIG. 4B), wherein the additional upstream sequence is selected from: a primer binding sequence; a restriction site, a sequencing bar-code or index, a Zip-code, one or more random nucleotides, a unique molecular identifier (UMI), flow-cell binding sites and combinations thereof. In some embodiments, an initial amplification may be performed using the conventional primers, and the second PCR amplification step is performed using the combo primers (FIG. 4C).

Figure 5A:
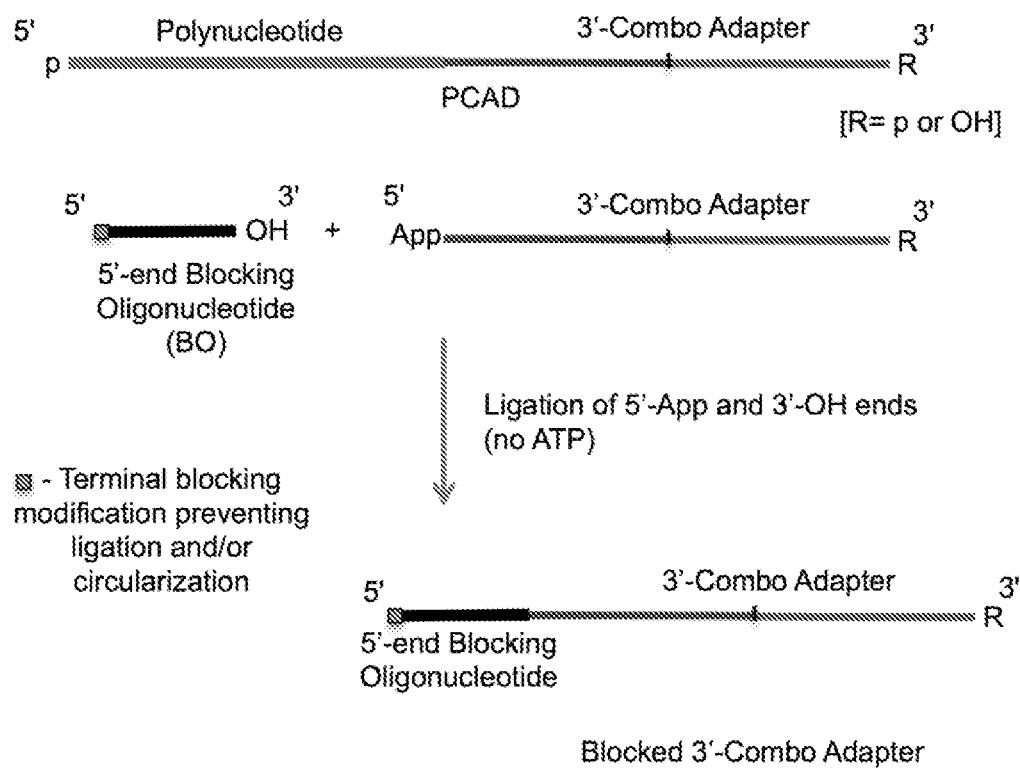
FIG. 5A: Ligation of a single-stranded BO containing a 3'-OH end with pre-adenylated 3'-CAD by a ligase in the absence of ATP.
Figure 5B:
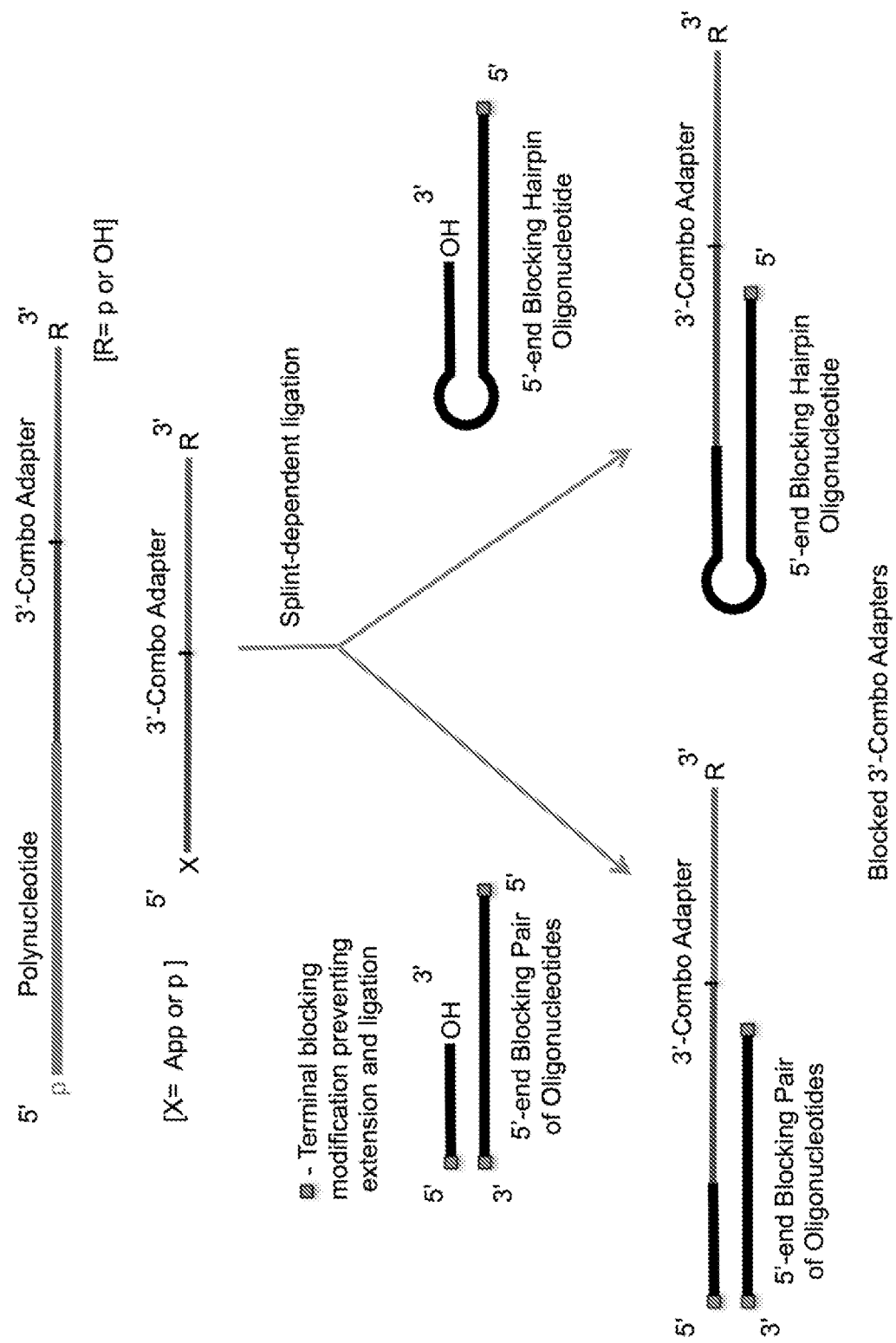
FIG. 5B: Splint-dependent ligation of a 3'-CAD having 5'-App or 5'-p end with the 3'-OH end of a double-stranded or hairpin BO by a ligase. The bottom strand of the double-stranded BO contains two segments, one of which can hybridize to a terminal segment of the target polynucleotide and the other to a terminal segment of the CAD, bringing the polynucleotide and CAD ends together.
Figure 5C:
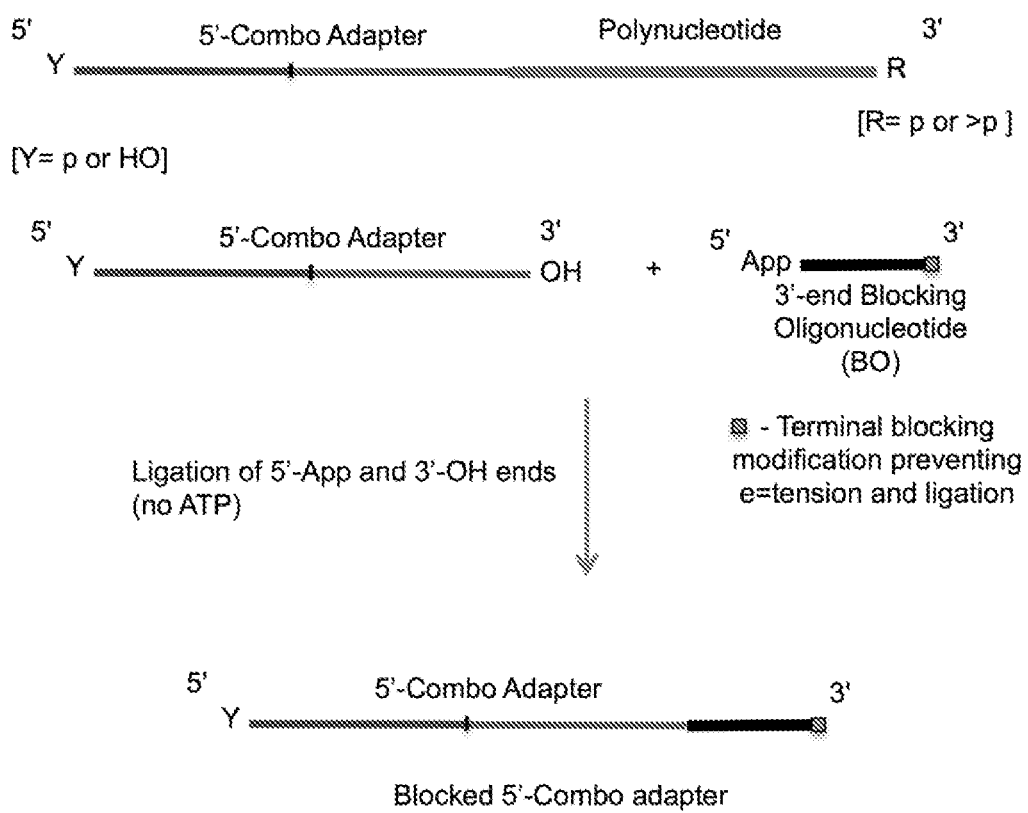
FIG. 5C: Ligation of a 5'-adenylated BO with the 3'-OH end of a 5'-CAD by a ligase in the absence of ATP.
Figure 5D:
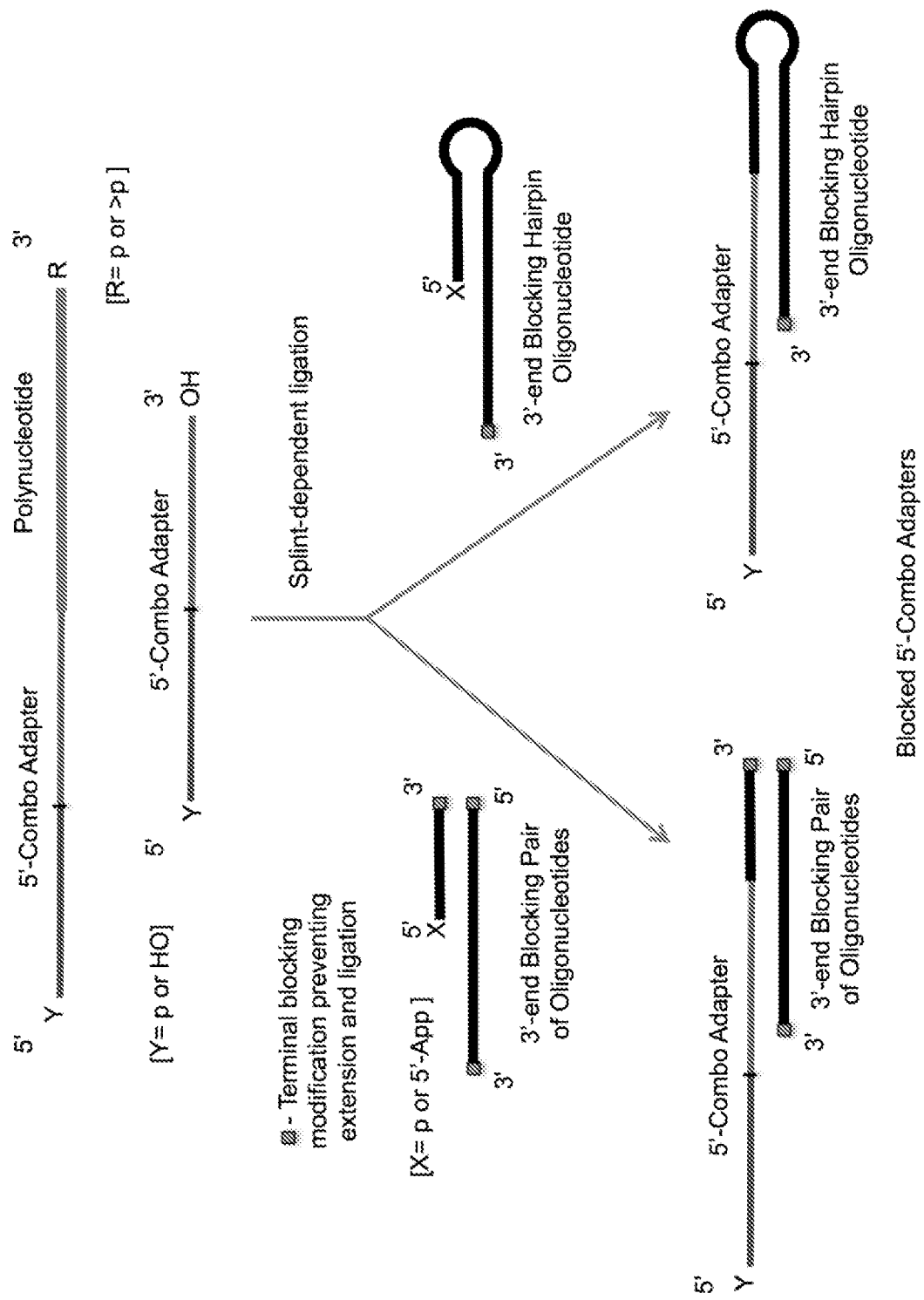
FIG. 5D: Splint-dependent ligation of the 3'-OH end of a 5'-CAD with the 5'-phosphate end of a double-stranded or hairpin BO in the presence of ATP.
Figure 5E:
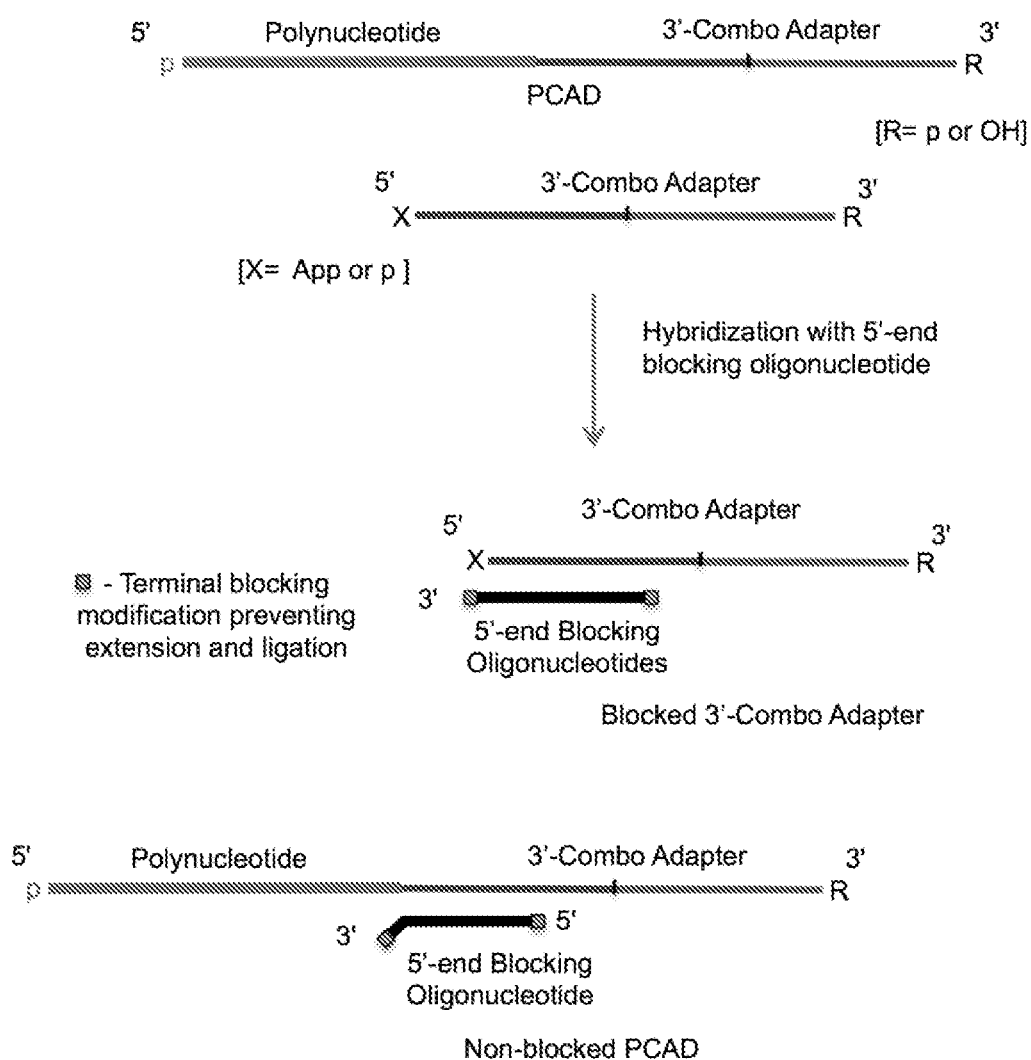
FIG. 5E: Hybridization with a BO that is complementary to at least a part of the 3'-combo adapter, where the BO forms a duplex with the 5' segment of the adapter and has 1 or more non-complementary nucleotides at its 3' end (3'-overhang).
Figure 5F:
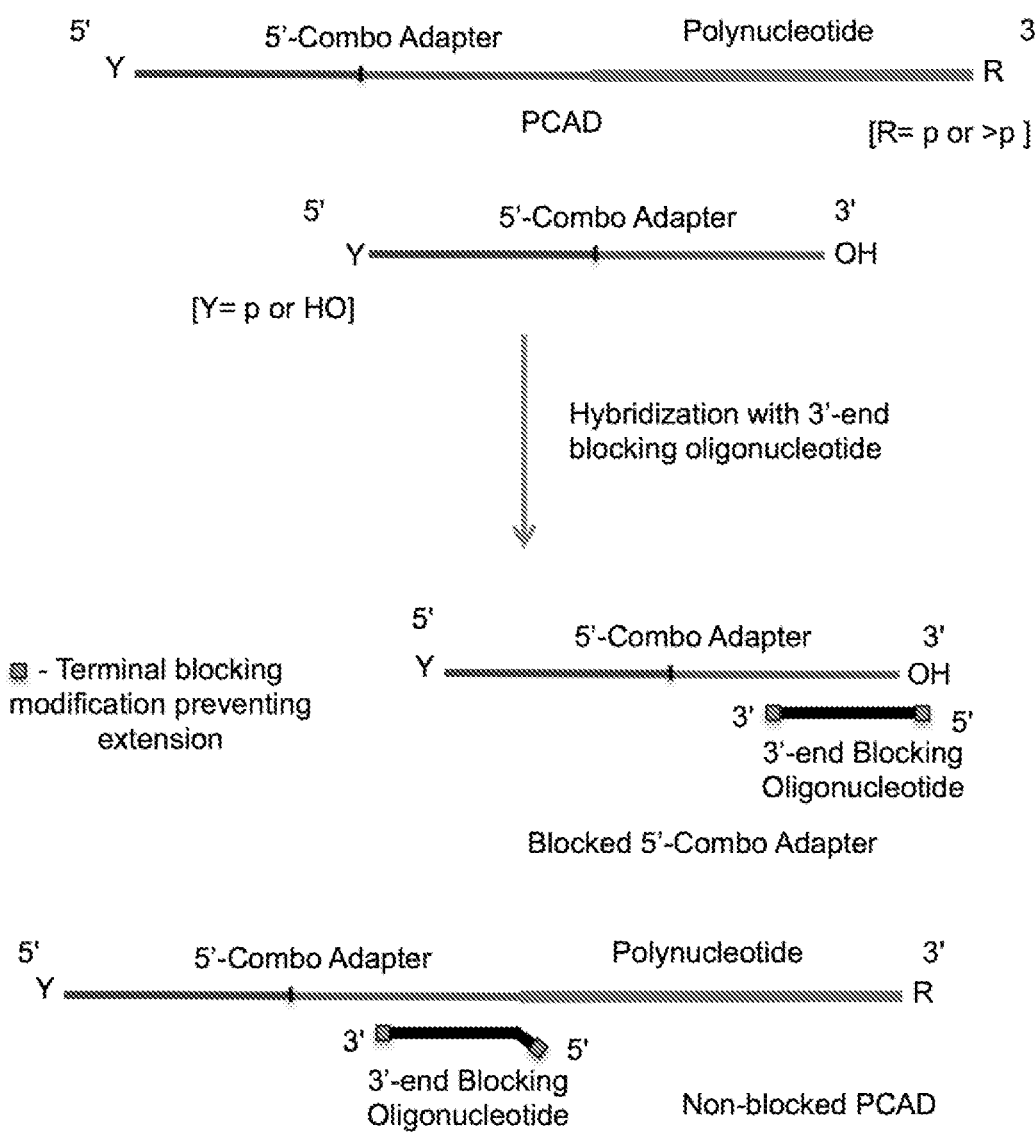
FIG. 5F: Hybridization with a BO that is complementary to at least a part of the 5'-combo adapter, where the BO forms a duplex with the 3'-segment of the adapter and has 1 or more non-complementary nucleotides at its 5' end (5'-overhang).
Figure 6A:
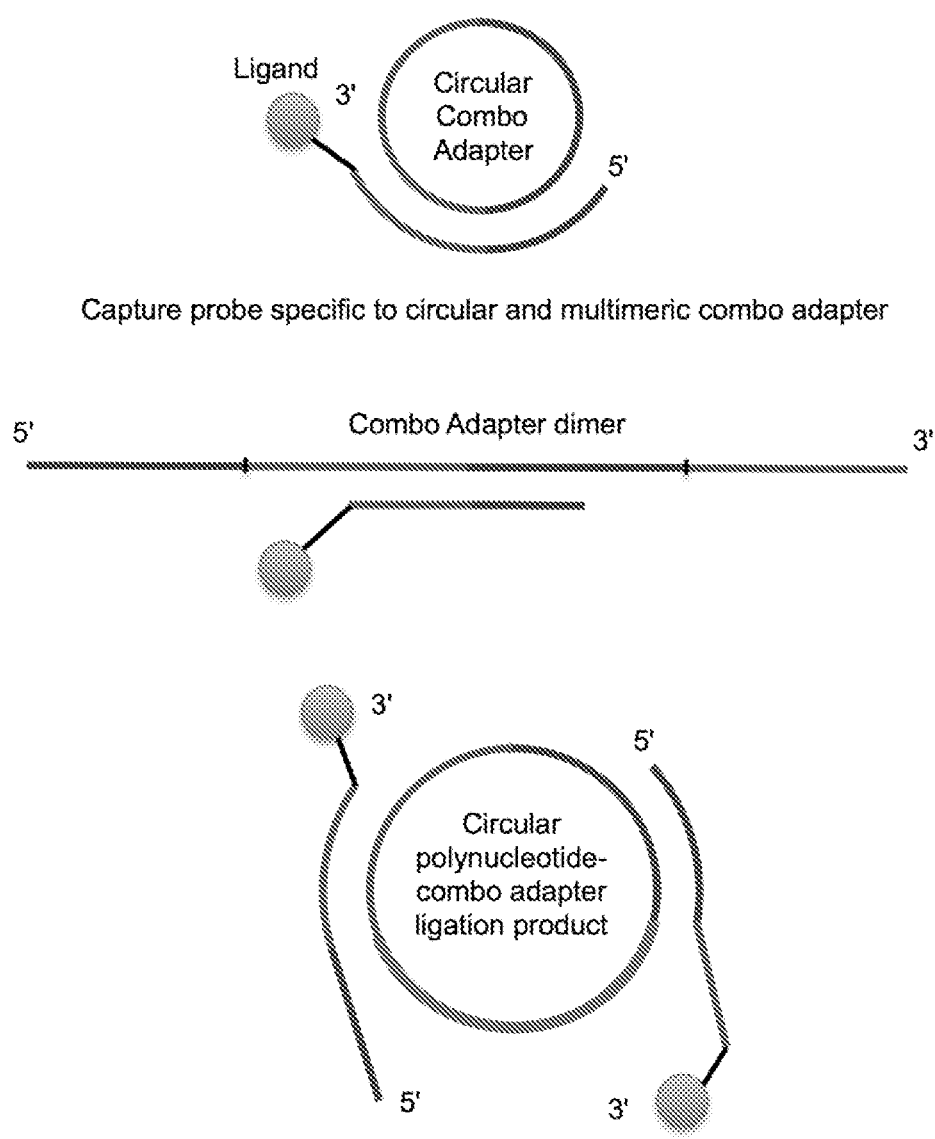
FIG. 6A: General design of oligonucleotide probes for specific capture and removal, prior to the RT step, of circular and multimeric forms of CAD lacking polynucleotide inserts. A ligand (e.g., biotin) attached to either terminal or internal nucleotide residues of the oligonucleotide probes allow affinity capture of the "empty" CAD sequences on columns or beads (e.g., streptavidin-coated magnetic beads).
Figure 6B:
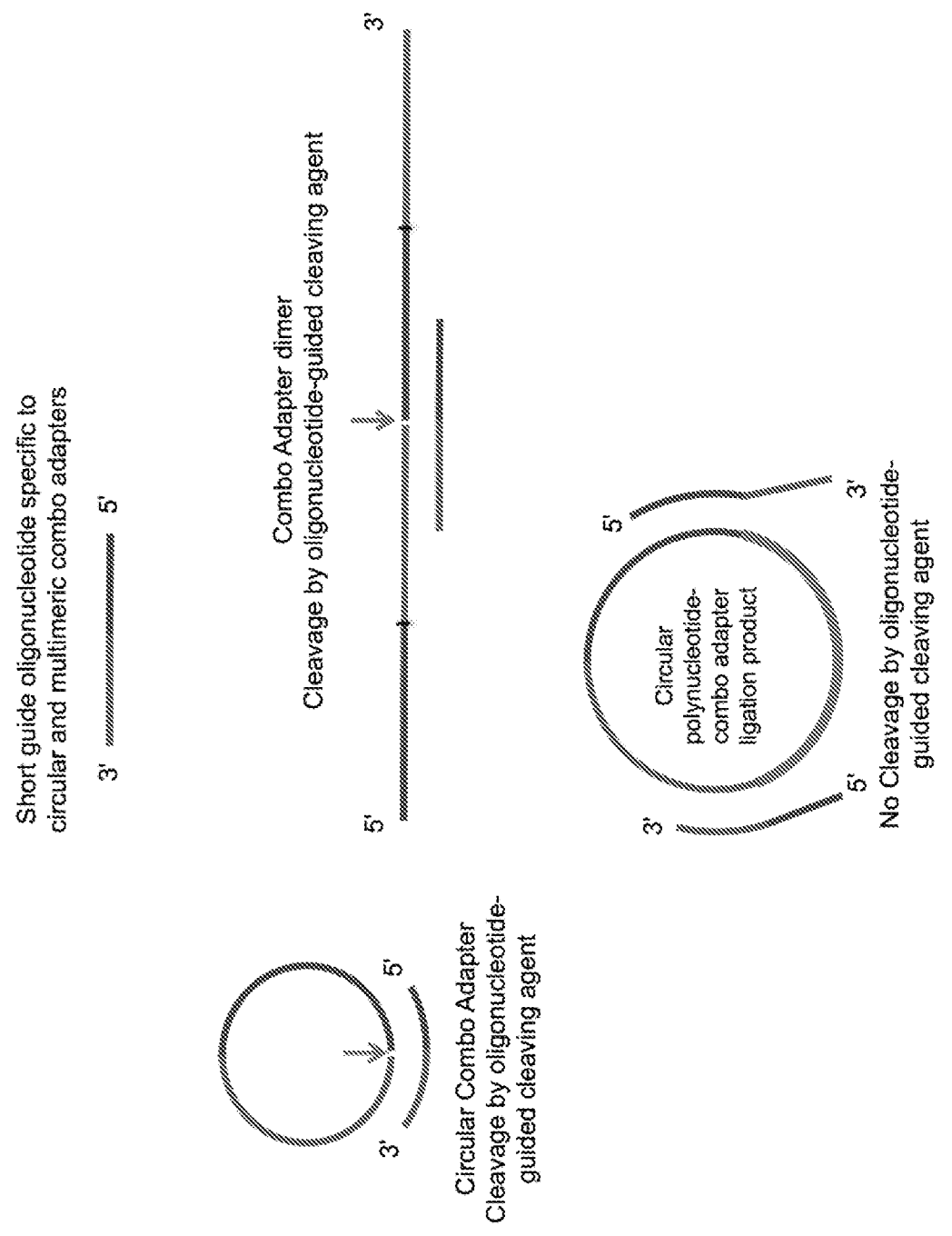
Figure 6C:
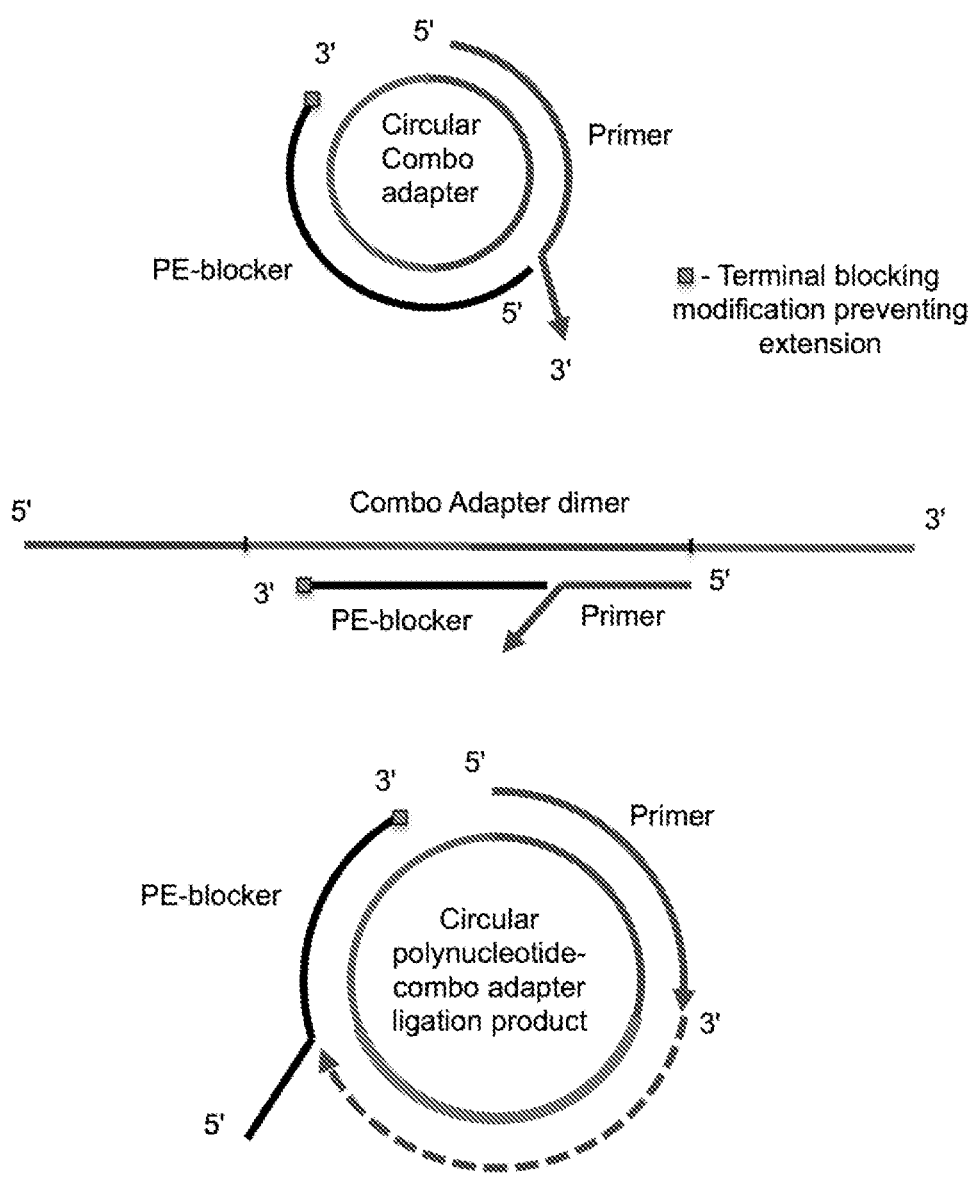
FIG. 6C: Scheme for using oligonucleotide probes (PE-blockers) to specifically block primer (e.g., RT primer) extension on circularized "empty" CAD and multimeric CAD templates (the CAD dimer is shown as an example). The PE-blocker has a 3'-end modification to prevent its extension by a polymerase. Primer extension by a polymerase with strand-displacement ability allows copying (e.g., reverse transcription) of only the circularized polynucleotide-combo adapter ligation product also referred as circularized polynucleotide-CAD ligation product (or circularized PCAD).
Figure 6D:
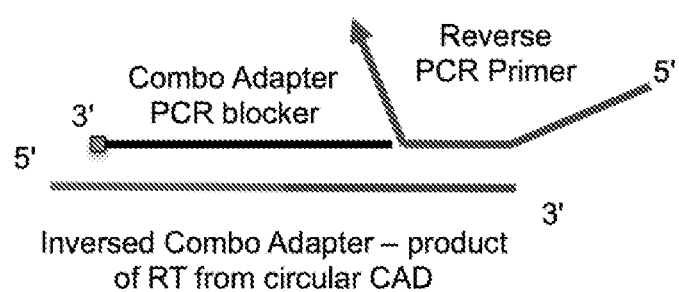
FIG. 6D: General design of oligonucleotide probes that allow specific blocking of PCR primer extension (PCR-blocker) of cDNAs derived from "empty" CADs.
Figure 6D:
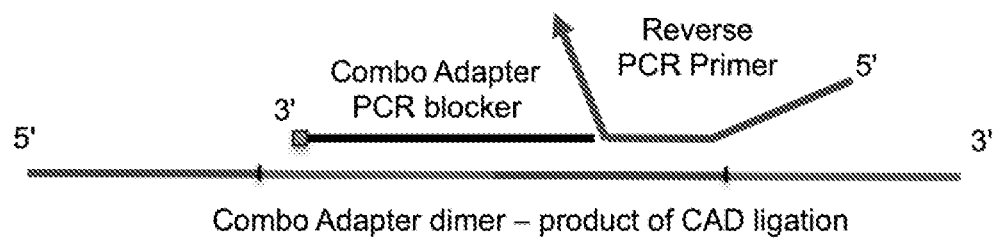

The method may further comprise depleting, separating, degrading, and/or blocking the remaining unligated combo adapter after ligating to the sample polynucleotide. Such blocking of the remaining unligated combo adapter may comprise ligating the remaining unligated combo adapter to a blocking oligonucleotide via either a splint-independent (FIGS. 5A and 5C) or a splint-dependent (FIGS. 5B and 5D) ligation reaction to prevent circularization and/or concatamerization of the combo adapter. The blocking of remaining unligated combo adapter may comprise hybridizing it to a blocking oligonucleotide to prevent circularization and/or concatamerization of the combo adapter (FIG. 5E-F). The depleting of remaining unligated combo adapter may comprise hybridizing circular or concatameric forms of said combo adapter with a capture oligonucleotide partially complementary to the junction between the 5' and 3' ends of the combo adapter and capture of the resulting hybridized circular or concatameric forms on a solid support (FIG. 6A). Blocking of remaining unligated combo adapter may comprise hybridizing circular or concatameric forms of said remaining unligated combo adapter with a blocking oligonucleotide partially complementary to the junction between the 5' and 3' ends of the combo adapter, wherein said blocking oligonucleotide prevents a primer extension (e.g., reverse transcription) and/or PCR amplification (FIG. 6C-D).

The ligation of blocking oligonucleotides with combo adapter may be combined with the converting of reversible blocking groups to active groups on the adapter-polynucleotide ligation products to allow its circularization. The method may comprise degrading the unligated combo adapter before circularizing. The method may comprise degrading the unligated combo adapter before circularizing, wherein said combo adapter comprises 5'-end groups selected from: 5'-p and 5'-OH. The method may further comprise degrading any remaining non-circularized combo adapter or adapter-polynucleotide ligation product after circularizing. In each case, the degrading may be performed with an exonuclease are selected from: Exonuclease I, Exonuclease II associated with DNA polymerase I, Exonuclease III, Exonuclease VII, T5 Exonuclease, Terminator™ 5"-Phosphate-Dependent Exonuclease, Xm I exoribonuclease, Rec J exonuclease, RecJf, and RNAse R or combination thereof. The method may further comprise degrading or cleaving circularized combo adapter after circularizing. Such degrading or cleaving may be performed by a cleaving agent that is guided or assisted by an oligonucleotide complementary to the junction between the 5'- and 3'-end segments of the combo adapter (FIG. 6B). Such degrading or cleaving may be performed by a cleaving agent that is guided or assisted by internal secondary structure of the combo adapter stabilized by its circularization. Said cleaving agent may be selected from: an RNase H, an RNAse H II, Hybridase™ Thermostable RNase H, a restriction endonuclease, duplex specific endonuclease, Cas9 nuclease, a ribozyme, deoxyribozyme or an artificial chemical nuclease). The method may further comprise purifying and/or enriching an intermediate selected from: the adapter-polynucleotide ligation product; the circularized polynucleotide; complementary monomeric nucleic acids; an amplicon; and any combination thereof. The purifying may involve technique(s) selected from: spin-column purification, bead-based separation, denaturing gel-electrophoresis, non-denaturing gel electrophoresis, a capillary electrophoresis, ethanol precipitation and combinations thereof.

In some embodiments, these methods are employed to detect the presence of a plurality of sample polynucleotides in the sample. In some embodiments, disclosed herein, are methods of detecting a presence of a plurality of sample polynucleotides in a sample, including the general steps of: a) ligating a plurality of combo adapters to the plurality of sample polynucleotides to generate a plurality of adapter-polynucleotide ligation products; b) circularizing one or more of the plurality of adapter-polynucleotide ligation products by ligating the 5'-end of the one or more adapter-polynucleotide ligation products to its 3'-end; c) synthesizing a plurality of monomeric nucleic acids, wherein each of the monomeric nucleic acids is complementary to each of the plurality of sample polynucleotides flanked by at least a portion of 3'- and 5'-proximal segments of combo adapter; and d) detecting the presence of the sample polynucleotides. In some embodiments, the plurality of monomeric nucleic acids are separate (e.g., not in the form of a concatamer). In some embodiments, the method does not comprise rolling circle amplification of the sample polynucleotide.

In some embodiments, these methods are employed to detect the presence of a first sample polynucleotide and a second sample polynucleotide in a sample. In some embodiments, the methods of detecting the first sample polynucleotide and a second sample polynucleotide in the sample, comprise: a) ligating a first combo adapter to a first sample polynucleotide to generate a first adapter-polynucleotide ligation product and ligating a second combo adapter to a second sample polynucleotide to generate a second adapter-polynucleotide ligation product; b) circularizing the first adapter-polynucleotide ligation product by ligating the 5'-end of the first polynucleotide-CAD ligation product to its 3'-end, and circularizing the second adapter-polynucleotide ligation product by ligating the 5'-end of the second adapter-polynucleotide ligation product to its 3' end; c) synthesizing a first monomeric nucleic acid, wherein the first monomeric nucleic acid comprises a sequence complementary to a sequence consisting of the first sample polynucleotide flanked by at least a portion of the 3'- and 5'-proximal segments of combo adapter, and synthesizing a second monomeric nucleic acid, wherein the second monomeric acid comprises a sequence complementary to a sequence consisting of the second sample polynucleotide flanked by at least a portion of the 3'- and 5'-proximal segments of combo adapter; and d) detecting the presence of the first sample polynucleotide and the second sample polynucleotide. In some embodiments, the first combo adapter and the second combo adapter are the same. In some embodiments, the first combo adapter and the second combo adapter are different. In some embodiments, the first combo adapter consists of a first sequence and the second combo adapter consists of a second sequence. In some embodiments, the first sequence and the second sequence are identical. In some embodiments, the first sequence and the second sequence are similar. In some embodiments, the first sequence and the second sequence are different.

In some embodiments, the methods comprise detecting a first sample polynucleotide in a first sample and a second sample polynucleotide in a second sample. In some embodiments, the methods of detecting the first sample polynucleotide in the first sample and a second sample polynucleotide in the second sample, comprise: a) ligating a first combo adapter to a first sample polynucleotide to generate a first adapter-polynucleotide ligation product and ligating a second combo adapter to a second sample polynucleotide to generate a second adapter-polynucleotide ligation product; b) circularizing the first adapter-polynucleotide ligation product by ligating the 5'-end of the first adapter-polynucleotide ligation product to its 3'-end, and circularizing the second adapter-polynucleotide ligation product by ligating the 5'-end of the second adapter-polynucleotide ligation product to its 3' end; c) synthesizing a first monomeric nucleic acid, wherein the first monomeric nucleic acid is complementary to the first sample polynucleotide and at least a portion of 3'- and 5'-proximal segments of the first combo adapter and synthesizing a second monomeric nucleic acid, wherein the second monomeric acid is complementary to the second sample polynucleotide flanked by at least a portion of the 3'- and 5'-proximal segments of the second combo adapter; and d) detecting the presence of the first sample polynucleotide and the second sample polynucleotide. The methods may further comprise combining the first sample polynucleotide and the second sample polynucleotide. The first sample polynucleotide and the second sample polynucleotide may be combined before the ligating. The first sample polynucleotide and the second sample polynucleotide may be combined after the ligating. The first sample polynucleotide and the second sample polynucleotide may be combined before the circularizing. The first sample polynucleotide and the second sample polynucleotide may be combined after the circularizing. The first sample polynucleotide and the second sample polynucleotide may be combined before the synthesizing. The first sample polynucleotide and the second sample polynucleotide may be combined after the synthesizing. The first sample polynucleotide and the second sample polynucleotide may be combined before the detecting. The first sample polynucleotide and the second sample polynucleotide may be combined after the detecting. In some embodiments, the first combo adapter consists of a first sequence and the second combo adapter consists of a second sequence. In some embodiments, the first sequence and the second sequence are identical. In some embodiments, the first sequence and the second sequence are similar. In some embodiments, the first sequence and the second sequence are different. In some embodiments, the first sequence comprises a first barcode corresponding to the first sample and the second sequence comprises a second barcode corresponding to the second sample, wherein the first barcode and the second barcode are different. The barcode is a sequence that corresponds to a sample. The barcode may also be referred to as a zip-code, sequencing index, or other various terms used in the art.

Disclosed herein are methods for determining a sequence of a sample polynucleotide in a sample comprising: a) ligating a combo adapter to the sample polynucleotide to produce an adapter-polynucleotide ligation product, wherein said combo adapter comprises a 5'-proximal segment and a 3'-proximal segment, wherein each proximal segment comprises at least one sequencing adapter, primer binging site, sequencing bar-code, or a combination thereof; b) optionally modifying the free, non-ligated combo adapter to prevent its circularization; c) circularizing said adapter-polynucleotide ligation product by ligating its 5' end to its 3' end to produce a circularized adapter-polynucleotide ligation product; d) optionally depleting, degrading or separating the circularized non-ligated combo adapter to prevent its amplification; e) hybridizing a first primer that is at least partially complementary to the 5'-proximal segment of said combo adapter, to said circularized adapter-polynucleotide ligation product; f) extending said first primer with a polymerase to produce a monomeric nucleic acid that is complementary to the sample polynucleotide; g) amplifying said monomeric nucleic acid using said first primer and a second primer, wherein the sequence of the second primer is at least partially complementary to the 3'-proximal segment of said combo adapter to produce a monomeric nucleic acid that is complementary to the sample polynucleotide flanked by at least a portion of the 3'- and 5'-proximal segments of the combo adapter; h) optionally removing/depleting or modifying circular and multimeric combo adapter species to prevent their amplification; i) sequencing the monomeric nucleic acid or portion thereof, thereby determining the sequence of the sample polynucleotide.

Further disclosed herein are methods for preparing a sequencing library for a plurality of sample polynucleotides in a sample comprising: a) ligating a combo adapter to the plurality of sample polynucleotides to produce a plurality of adapter-polynucleotide ligation products, wherein said combo adapter comprises a 5'-proximal segment and a 3'-proximal segment, wherein each proximal segment comprises at least one sequencing adapter, sequencing bar-code, primer binding site, or a combination thereof; b) optionally modifying the free, non-ligated combo adapter to prevent its circularization; c) circularizing said plurality of adapter-polynucleotide ligation products by ligating their 5' ends to their 3' ends to produce a plurality of circularized adapter-polynucleotide ligation products; d) optionally depleting, degrading or separating the circularized non-ligated combo adapter to prevent its amplification; e) hybridizing a first primer at least partially complementary to the 5'-proximal segment of said combo adapter, to said circularized adapter-polynucleotide ligation products; f) extending said first primer with a polymerase to produce a plurality of monomeric nucleic acids that is complementary to the sample polynucleotide flanked by at least a portion of the 3'- and 5'-proximal segments of combo adapter; h) optionally removing/depleting or modifying circular and multimeric combo adapter species to prevent their amplification; and i) amplifying said plurality of monomeric nucleic acids using said first primer and a second primer, wherein the sequence of the second primer is at least partially complementary to the 3'-proximal segment of said combo adapter to produce amplicon(s) comprising the sequencing library. The method of preparation of sequencing libraries may be performed according to RealSeq®-AC scheme (FIG. 7). The method may further comprise sequencing the plurality of monomeric nucleic acids or portions thereof, thereby determining at least one sequence of the plurality of sample polynucleotides.

Ligating

Disclosed herein are methods of sequencing or detecting sample polynucleotides in a sample, including ligating a combo adapter (CAD) to the sample polynucleotides. Ligating the sample polynucleotide to the CAD to produce the polynucleotide-CAD ligation product (which also referred as adapter-polynucleotide ligation product) may occur before circularizing. In some embodiments, ligating the sample polynucleotide to the CAD to produce the polynucleotide-CAD ligation product may occur before circularizing. In some embodiments, ligating the sample polynucleotide to the CAD to produce the polynucleotide-CAD ligation product must occur before circularizing. In some embodiments, ligating the sample polynucleotide to the CAD to produce the polynucleotide-CAD ligation product may occur during circularizing.

Ligating the sample polynucleotide to the CAD may be performed with at least one ligase. The ligase may be selected from: T4 RNA ligase, T4 RNA ligase 1 (Rnl1), T4 RNA ligase 2 (Rnl2), T4 RNA Ligase 2 truncated, T4 RNA Ligase 2 truncated K227Q, T4 RNA Ligase 2 truncated KQ, Thermostable 5' AppDNA/RNA Ligase, Mth RNA Ligase, CircLigase™ ssDNA ligase, CircLigase™ II ssDNA ligase, CircLigase™ RNA Ligase, Thermostable RNA ligase, ThermoPhage DNA ligase, T3 DNA ligase, T4 DNA ligase, and SplintR® Ligase.

In some embodiments, the CAD is ligated to the 5' end of the polynucleotide. In some embodiments, the CAD is ligated to the 3' end of the polynucleotide.

In some embodiments, the ligating comprises splint-independent ligation of the CAD to the sample polynucleotide. In some embodiments, the ligating comprises splint-assisted ligation of the CAD to the sample polynucleotide.

In some embodiments, the CAD and/or the sample polynucleotide is contacted with an enzyme that modifies the CAD and/or the sample polynucleotide after circularizing. The enzyme, by way of non-limiting example, may be a nucleic acid cleaving enzyme.

In some embodiments, the methods comprise contacting the sample polynucleotide(s) with a plurality of combo adapters. In some embodiments, the plurality of combo adapters comprises a first combo adapter and a second combo adapter. In some embodiments, the first combo adapter and the second combo adapter are the same. In some embodiments, the first combo adapter and the second combo adapter are different. In some embodiments the first combo adapter is ligated to the sample polynucleotide and the second adapter is not ligated to the sample polynucleotide, leaving a remaining unligated combo adapter.

In some embodiments, the methods comprise blocking the remaining unligated combo adapter before the circularizing. In some embodiments, blocking of the remaining unligated combo adapter comprises ligating the remaining unligated combo adapter to a blocking oligonucleotide. Ligating the remaining unligated combo adapter to a blocking oligonucleotide may occur via either a splint-dependent or a splint-independent ligation reaction to prevent circularization and concatamerization of the combo adapter. Blocking of the remaining unligated combo adapter may comprise hybridizing it to a blocking oligonucleotide to prevent circularization and/or concatamerization of the combo adapter. In some embodiments, depleting the remaining unligated combo adapter may comprise its degrading by an exonuclease or mixture of exonucleases.

Circularizing

Disclosed herein are methods of sequencing or detecting polynucleotides in a sample, including circularizing a polynucleotide-CAD ligation product. Circularizing the polynucleotide-CAD ligation product may comprise ligation of a first end of the sample polynucleotide to a first end of the combo adapter. In some embodiments, the 5' end of the sample polynucleotide is ligated to the 3' end of the combo adapter. In some embodiments, the 3' end of the sample polynucleotide is ligated to the 5' end of the combo adapter.

In certain embodiments of the invention, circularizing comprises splint-independent ligation. Splint-independent ligation may comprise use of an enzyme selected from: T4 RNA ligase, T4 RNA ligase 1, T4 RNA ligase 2, Mth RNA Ligase, CircLigase™ ssDNA ligase, CircLigase™ II ssDNA ligase, CircLigase™ RNA Ligase, and Thermostable RNA ligase. In some embodiments, direct ligation comprises chemical ligation. In some embodiments, circularizing comprises splint-assisted (also referred to splint-dependent) ligation. Splint-assisted ligation may comprise use of an enzyme selected from: T4 RNA ligase 2, and a DNA ligase. Splint-assisted ligation may comprise chemical ligation.

In some embodiments, the methods further comprise depleting, the remaining unligated combo adapter or a circularized combo adapter after the circularizing. In some embodiments, depleting of the remaining unligated combo adapter or circularized combo adapter comprises hybridizing a circular or concatameric form of said combo adapter with a capture oligonucleotide partially complementary to the junction between the 5' and 3' ends of the combo adapter and capture of the resulting hybridized circular or concatameric forms of the combo adapter on a solid support. In some embodiments, depleting of the circularized/unligated combo adapter comprises its degrading or cleaving by a cleaving agent that is guided or assisted by an oligonucleotide complementary to the junction between the 5'- and 3'-end segments of the combo adapter. In some embodiments, depleting of the circularized/unligated combo adapter comprises its degrading or cleaving by a cleaving agent that is guided or assisted by internal secondary structure of the combo adapter stabilized by its circularization. In certain embodiments of the invention, circularizing of an adapter-polynucleotide ligation product is followed by degrading remaining non-circularized adapter-polynucleotide ligation products and non-circularized combo adaptor. Degrading may comprise contacting the non-ligated combo adaptor with an exonuclease or mixture of exonucleases. Degrading the non-ligated combo adaptor may reduce a background signal that evolves as result of unintentional amplification and sequencing of the non-ligated combo adapter. In some embodiments, blocking of the remaining unligated combo adapter comprises hybridizing circular or concatameric forms of said remaining unligated combo adapter with a blocking oligonucleotide partially complementary to the junction between the 5' and 3' ends of the combo adapter, wherein said blocking oligonucleotide prevents said extending and/or amplifying.

Extending

Disclosed herein are methods of sequencing polynucleotides in a sample, including hybridizing a primer to the circularized adapter-polynucleotide ligation product and extending said primer with a polymerase to produce a monomeric nucleic acid (cNA) that comprises a sequence complementary to a sequence consisting of [or comprising] the sample polynucleotide flanked by at least a portion of the 3'- and 5'-proximal segments of combo adapter. In some embodiments of the invention, the circularized polynucleotide-CAD ligation product (circularized PCAD) is used as a template for reverse transcription (RT) which yields a monomeric cDNA. The reverse transcription may comprise two steps: a) binding of the circularized polynucleotide with an oligonucleotide RT primer; and b) enzymatic extension of the RT primer by a reverse transcriptase. The reverse transcriptase may lack RNAse H activity, such as SuperScript II, by way of non-limiting example. In some embodiments of the invention, the reverse transcriptase may have RNAse H activity, such as AMV, by way of non-limiting example, to cleave the circularized PCAD template and thereby restrict rolling-circle amplification. In some embodiments, the reverse transcription may be performed in the presence of RNAse H. In some other embodiments, the reverse transcription may be followed by RNAse H treatment. The RNAse H can degrade the circularized PCAD template containing at least one ribonucleotide to increase the efficiency of cNA amplification by PCR. In certain embodiments of the invention, the RT primer is target-specific and contains a sequence substantially complementary to a region of the circularized polynucleotide. In certain embodiments the sequence substantially complementary to the region of the circularized polynucleotide is 6 or 7 nucleotides in length. In some embodiments, the sequence substantially complementary to the region of the circularized polynucleotide is about 8 nucleotides to about 18 nucleotides in length. In some embodiments, the sequence substantially complementary to the region of the circularized polynucleotide is longer than 18 nucleotides.

In some embodiments of the invention, the RT primer also serves as a reverse PCR primer, which can be used along with an additional forward PCR primer in the amplifying step. In some embodiments, the RT primer has a different sequence from either of the PCR primers.

Reverse transcription may be performed with any reverse transcriptase. By way of non-limiting example, the reverse transcriptase may be selected from: SuperScript® II, SuperScript® III, SuperScript® IV, ThermoScript™, Maxima™ RevertAid™; AMV, M-MuLV, and ProtoScript® II Reverse Transcriptases.

Reverse transcription may be performed with a reverse transcriptase selected from: RNA-dependent DNA polymerases (reverse transcriptases) having RNAse H activity; Reverse Transcriptase mutants lacking RNase H activity; DNA-dependent DNA polymerase (DNA polymerase); reverse transcriptases lacking DNA-dependent activity, which cannot use DNA as a template; reverse transcriptases having DNA-dependent activity, which can use both RNA and DNA as a template; DNA polymerases lacking RNA-dependent activity, which cannot use RNA as a template, and DNA polymerases having RNA-dependent activity, which can use both DNA and RNA as a template. In some embodiments, the DNA polymerase is selected from: DNA Polymerase I Large (Klenow) Fragment, Bst 3.0 DNA Polymerase, Tth and rTth DNA Polymerase Polymerases.

In some embodiments, the method further comprises optimizing the efficiency/yield of the reverse transcriptase reactions to allow for smaller RNA inputs in sequencing library preparation. Such optimization may include use of alternative designs for the combo adapter and selecting an appropriate reverse transcriptase for each design. Such designs may include, besides the half-DNA/half-RNA design described in Example 1, and without limitation: (i) all-RNA content; (ii) all-DNA content; (iii) the same DNA and RNA segments as in Example 1 but without the non-nucleotide spacer separating them; (iv) the same as (iii) but with 2'-OMe-modified residues substituting for the DNA segment. For each CAD design, DNA polymerases with RNA-dependent activity may be selected to have one of the following characteristics (without limitation): (i) RNA-dependent polymerase activity, with or without RNase H activity; and (ii) both RNA-dependent and DNA-dependent activity. The list of polymerases may include: Superscript® II, III and IV and ThermoScript™ reverse transcriptases (Life Technologies); AMV, M-MuLV and ProtoScript® II Reverse Transcriptases (NEB); Maxima™ and RevertAid™ Reverse Transcriptases (ThermoFisher); DNA Polymerase I, Large (Klenow) Fragment (NEB); and Tth DNA Polymerase (Promega).

Reverse transcribing may produce complementary nucleic acids (cNAs), Extending the primer may produce complementary nucleic acids (cNAs). The cNAs may be monomeric. The cNAs may comprise molecules selected from: unmodified single-stranded DNA (ssDNA); modified ssDNA wherein modified deoxyribonucleoside triphosphates (dNTPs) or modified primers are used; and RNA-modified ssDNA wherein ribonucleoside triphosphates (rNTPs) and dNTPs or RNA-containing primers are used.

Amplifying

The methods, compositions, and kits disclosed herein may further comprise amplifying a monomeric nucleic acid or portion thereof, wherein the monomeric nucleic acid is complementary to the polynucleotide-CAD ligation product or portion thereof. Amplifying may produce at least one amplicon, wherein each amplicon comprises a sequence complementary to a polynucleotide flanked by at least a portion of sequences of the 5'-proximal and 3'-proximal segments of the combo adapter.

The methods disclosed herein may comprise PCR amplification of nucleic acids. The nucleic acids may be complementary nucleic acids produced by reverse transcription of circularized polynucleotide-CAD ligation products. The complementary nucleic acids may be monomeric nucleic acids.

PCR amplifying may be performed with a DNA polymerase selected from, by way of non-limiting example: DNA Polymerase I Large (Klenow) Fragment, Bst 3.0 DNA Polymerase, Tth and rTth DNA Polymerase.

There are numerous PCR methods well known in the art, most of which could be used in the present methods. By way of non-limiting example, PCR amplifying may comprise a method selected from: standard exponential PCR, asymmetric PCR, and Linear After The Exponential PCR (LATE-PCR).

Amplifying the cNAs may produce amplicons comprising molecules selected from: double-stranded DNA (DNA); ssDNA; modified DNA; and ssDNA with modified deoxyribonucleoside triphosphates (dNTPs). Amplifying the cNAs may produce amplicons comprising molecules selected from: RNA-modified DNA; and ssDNA with ribonucleoside triphosphates (rNTPs). In some embodiments, amplifying comprises the use of modified primers. The primers may comprise dNTPs. The primers may comprise RNA.

Optionally, complementary nucleic acids (cNAs) can be subjected to affinity purification by capture on immobilized anchor oligonucleotides (e.g., on magnetic beads) and separation from the irrelevant nucleic acids (e.g., by washing) before PCR. This step serves to further reduce background and increase assay sensitivity.

Detecting

The methods disclosed herein may comprise detecting a polynucleotide. In general, the methods disclosed herein comprise generating and sequencing a complementary nucleic acid corresponding to the polynucleotide (e.g. a cDNA to the RNA). Thus, one of skill in the art would easily deduce the sequence of the polynucleotide from the sequence of the complementary nucleic acid. In some embodiments, detecting may be performed by an array method including (but not limited to): oligonucleotide arrays, LNA arrays, microarrays, bead arrays, microfluidic primer extension array, PCR array, and amplification-based array. In other embodiments, said detecting may be performed by real-time qPCR or digital PCR. In other embodiments, said detecting may be performed using isothermal amplification.

The methods generally comprise ligating a combo adapter to the polynucleotide before circularizing and reverse transcription of the polynucleotide. Thus the complementary nucleic acid may comprise a sequence complementary to the combo adapter or portion thereof. The combo adapter may comprise sequencing adapters corresponding to known sequencing methods, primers and enzymes. Sequencing methods are well known to one skilled in the art. By way of non-limiting example, sequencing methods may be selected from: Sanger sequencing; next-generation sequencing; and single-molecule sequencing. Also by way of non-limiting example, sequencing methods may be selected from: standard Sanger sequencing; next-generation sequencing (including but not limited to: Illumina's Solexa; Roche's 454, Life Technologies's SOLiD, ThermoFisher's Ion Torrent); and single-molecule sequencing (including but not limited to using nanopore sequencing).

Combo Adapter (CAD)

Disclosed herein are combo adapters (CAD) comprising: a) nucleic acid residues, and, optionally, at least one modified residue; b) a 5'-proximal segment and a 3'-proximal segment, wherein each proximal segment comprises at least one sequencing adapter, primer binding site, sequencing bar-code, detection sequence, or a combination thereof; c) a 5' end and a 3' end that allow: i) intermolecular ligation of said combo adapter to a sample polynucleotide to produce an adapter-polynucleotide ligation product (also referred to as adapter-polynucleotide ligation product); and ii) circularization of the adapter-polynucleotide ligation product to produce a circularized adapter-polynucleotide ligation product; and d) a template-deficient segment for primer extension by a polymerase, wherein the template-deficient segment or at least one modified residue (or moiety) restricts rolling-circle amplification. The modified residue may be between the 5'-proximal segment and the 3'-proximal segment of the combo adapter. The template-deficient segment may be between the 5' proximal segment and the 3' proximal segment. The modified residue(s) or moieties may be located in the template. The sequencing adapters may comprise a sequence required by sequencing methods selected from: standard Sanger sequencing; next-generation sequencing; and single-molecule sequencing. The combo adapter may comprise at least one sequence selected from: a sequencing adapter, a primer binding site, a detection sequence, a probe hybridization sequence, a capture oligonucleotide binding site, a polymerase binding site, an endonuclease restriction site, a sequencing bar-code, an indexing sequence, a Zip-code, one or more random nucleotides, a unique molecular identifier (UMI), sequencing flow-cell binding sites and combinations thereof. The 5'-proximal segment or the 3'-proximal segment of said combo adapter may comprise at least one sequencing adapter. The 5'-proximal segment and the 3'-proximal segment of said combo adapter may each comprise at least one sequencing adapter. The sequencing adapters may enable sequencing of the adapter-polynucleotide ligation product or complement thereof. The combo adapter may contain at least one ribonucleotide (RNA), deoxyribonucleotide (DNA), or modified nucleic acid residue. Non-limiting examples of modified residues include a deoxyuridine (dU), an inosine (I), a deoxyinosine (dI), an Unlocked Nucleic Acid (UNA), a Locked Nucleic Acid (LNA) comprising a sugar modification, a Peptide Nucleic Acid (PNA), an abasic site, and a nucleic acid residue with a modification selected from: a 5-nitroindole base modification, a 2'-phosphate (2'-p), a 2'-$NH_2$, a 2'-NHR, a 2'-OMe, a 2'-O-alkyl, a 2'-F, a 2'-halo, a phosphorothioate (PS), and a disulfide (S—S) internucleotide bond modification.

Provided herein are combo adapters (CADs) and methods comprising the use thereof, wherein the combo adapter comprises a 5' end and a 3' end that allow: i) intermolecular ligation of said combo adapter to a sample polynucleotide to produce an adapter-polynucleotide ligation product. By way of non-limiting example, the combo adapter may be a 5'-combo adapter (5'-CAD), which can be ligated to the 5' end of the sample polynucleotide to produce the adapter-polynucleotide ligation product. The combo adapter may be a 3'-combo adapter 3'-CAD), which can be ligated to the 3' end of the sample polynucleotide to form the adapter-polynucleotide ligation product. The 5'-combo adapter may comprise a 5'-hydroxyl (5'-OH) and a 3'-hydroxyl (3'-OH) before ligation of said 5'-combo adapter to the 5'-end of the sample polynucleotide. The 5'-CAD may comprise a 5'-phosphate (5'-p) and a 3'-phosphate (3'-p) before ligation of said 5'-CAD to the 5'-end of the sample polynucleotide. The 3'-CAD may also comprise 5'-p and 3'-p before ligation of said 3'-CAD to the 5'-end of the sample polynucleotide. The 3'-combo adapter may comprise a 5'-adenylated (5',5'-adenyl pyrophosphoryl, 5'-rApp) group referred below as App, and 3'-p. The terminal residues of the combo adapter may comprise a reversible blocking group. The reversible blocking group may be a 3'-end-blocking group. The said 3'-end-blocking group may be selected from: 3'-p, 2',3'-cyclic phosphate (2',3'>p or >p), 3'-O-(α-methoxyethyl) ether, and 3'-O-isovaleryl ester. The reversible blocking group may be a 5'-end-blocking group. The said 5'-end-blocking group may be selected from: 5'-OH, 5'-p, 5'-triphosphate (5'-ppp), 5'-diphosphate (5'-pp) and a 5'-cap structure.

The 5'-proximal segment or the 3'-proximal segment of the CADs disclosed herein, or a region between the 5'-proximal and 3'-proximal segments may comprise a moiety selected from a nucleic acid residue, a modified nucleic acid residue, an abasic site, a disulfide (S—S) internucleotide bond, and a non-nucleotide linker, wherein the moiety inhibits primer extension by a polymerase, thereby preventing rolling-circle amplification of the circularized adapter-polynucleotide ligation product. The modified nucleic acid residue may be selected from: a deoxyuridine, an inosine, a deoxyinosine, an Unlocked Nucleic Acid, a Locked Nucleic Acid, and a nucleic acid residue with modification selected from a 5-nitroindole base modification, a 2'-p, a 2'-NH$_2$, a 2'-NHR, a 2'-OMe, a 2'-O-alkyl, a 2'-F, and a 2'-halo. The combo adapter may comprise at least one cleavage (or cleavable) site(s). Said cleavage sites or cleavage sequences may be positioned within the proximal and 3'-proximal segments, or between its 5'-proximal and 3'-proximal segments of the combo adapter. In some embodiments, the cleavage site may be formed by internal secondary structure of the combo adapter. Said secondary structure may be stabilized by circularization of the combo adapter. The cleavage sites may be a substrate for a cleaving agent selected from: Uracil-DNA glycosylase, Endonuclease V, a restriction endonuclease, a ribozyme, a deoxyribozyme, artificial chemical nuclease, RNase H, RNase H II, Duplex-specific Nuclease, and Cas9 nuclease.

Further disclosed herein are combo adapters comprising: a) nucleic acid residues, and, optionally at least one modified residue or moiety; b) 5'-proximal and 3'-proximal segments, wherein each proximal segment comprises at least one detection sequence; c) 5' and 3' ends that allow: i) intermolecular ligation of said combo adapter to a sample polynucleotide to produce an adapter-polynucleotide ligation product; and ii) circularization of the adapter-polynucleotide ligation product to produce a circularized adapter-polynucleotide ligation product; and d) a template-deficient segment for primer extension by a polymerase, wherein the template-deficient segment or modified residue (or moiety) restricts rolling-circle amplification. The template-deficient segment may comprise at least one modified residue. The template-deficient segment may comprise at least one cleavage site or cleavable modified residues that could be cleaved by a chemical or enzymatic agent to stop the primer extension by a polymerase. The at least one modified residue may be selected from: a deoxyuridine (dU), an inosine (I), a deoxyinosine (dI), an Unlocked Nucleic Acid (UNA), a Locked Nucleic Acid (LNA) with a sugar modification, an abasic site, and a nucleic acid residue with a modification selected from: a 5-nitroindole base modification, a 2'-p, 2'-NH2, a 2'-NHR, a 2'-OMe, a 2'-O-alkyl, a 2'-F, a 2'-halo, a phosphorothioate (PS), and a disulfide (S—S) internucleotide bond modification.

The combo adapters may comprise RNA. The combo adapters may comprise DNA. The combo adapters may comprise a combination of RNA and DNA. The combo adapter generally comprises a modified residue. The modified residue may be located between the 5' proximal segment and the 3' proximal segment. The modified residue may be a nucleic acid of modification thereof. The modified residue may not be a nucleic acid. The modified residue may be an abasic site. The modified residue may be an abasic residue. The combo adapters may comprise non-nucleotide linkers. The modified residue may be a non-nucleotide linker. The combo adapters may comprise RNA, DNA, non-nucleotide linkers, modified nucleic acids, and any combination thereof. Modified nucleic acid residues may be selected from: deoxyuridine (dU), inosine (I), deoxyinosine (dI), an Unlocked Nucleic Acid (UNA) and a Locked Nucleic Acid (LNA). The modified nucleic acid may comprise a modification selected from: a 5-nitroindole base modification, a 2'-NH$_2$, a 2'-NHR, a 2'-OMe, a 2'-O-alkyl, a 2'-F, a 2'-halo, a sugar modification; and a phosphorothioate (PS) or disulfide (S—S) internucleotide bond modification.

In some embodiments, the template-deficient segment for primer extension by the polymerase restricts rolling-circle amplification (RCA), but enables production of a monomeric nucleic acid (as opposed to multimeric products of RCA). Generally, the methods and compositions herein prevent/restrict rolling circle amplification. However, rolling circle amplification, as used herein, may be substituted with unrestricted primer extension by polymerase. In some embodiments, the template-deficient segment for primer extension by the polymerase inhibits RCA, but enables production of a monomeric nucleic acid. In some embodiments, the template-deficient segment for primer extension by the polymerase prohibits RCA, but enables production of a monomeric nucleic acid. In general, the methods disclosed herein provide for very little to no rolling circle amplification. In some embodiments, RCA does not occur at all.

The methods disclosed herein comprise producing at least one monomeric nucleic acid. The monomeric nucleic acid may comprise a complementary nucleic acid (cNA) that is complementary to the sample polynucleotide or portions thereof. The monomeric nucleic acid may comprise a complementary nucleic acid comprising a sequence that is complementary to the CAD or portions thereof. By way of non-limiting example, the monomeric nucleic acid may comprise a sequence complementary to the sample polynucleotide, flanked by sequences that are complementary to at least a portion of the 5'-proximal segment and 3'-proximal segment of the CAD.

In some embodiments, the CAD is capable of being ligated to a single-stranded sample polynucleotide. In some embodiments, the CAD may be ligated to a single-stranded sample polynucleotide resulting from a denatured double stranded sample polynucleotide. In some embodiments, the CAD may be ligated to a double-stranded sample polynucleotide.

In some embodiments, the CAD comprises a detection sequence that enables sequencing of the monomeric nucleic acid or a portion thereof. For example, the cNA may comprise a sequence complementary to the detection sequence that acts as a template for a sequencing primer. The detection sequence, or complement thereof, may be used in various sequencing methods known in the art. By way of non-limiting example, sequencing methods may be standard Sanger sequencing; next-generation sequencing; or single-molecule sequencing. In some embodiments, the next-generation sequencing method is selected from: Solexa/Illumina, 454, SOLiD and Ion Torrent.

In some embodiments, the CAD comprises sequences selected from: primer binding; restriction sites, sequencing bar-code and indexing sequences, Zip-codes, at least one random nucleotide, and combination thereof.

In some embodiments, the CAD may comprise a probe binding site. The probe binding site or complement thereof may enable detection or purification of the polynucleotide-CAD ligation product and/or the circularized polynucleotide-CAD ligation product.

In some embodiments, at least one of a deoxyribonucleotides, a ribonucleotide, a modified nucleic acid residue, an abasic site, or a non-nucleotide linker is placed either within the 5'-proximal segment or between the 5'-proximal and 3'-proximal segments so as to inhibit primer extension by a polymerase, thereby preventing Rolling-Circle Amplification (RCA) of the circular polynucleotide-CAD ligation products and permitting a polymerase to produce only monomeric cNAs. In some embodiments, the CAD comprises a cleavage site(s) positioned between its 5'-proximal and 3'-proximal segments, and wherein chemical or enzymatic cleavage at said cleavage site(s) after the circularization step stops primer extension by a polymerase, thereby preventing Rolling-Circle Amplification (RCA) of the circularized polynucleotide-CAD ligation products and permitting a polymerase to produce only monomeric cNAs. In some embodiments, cleavage sites are substrates for nucleotide-specific or sequence-specific nucleases selected from: Uracil-DNA glycosylase (UDG), which cleaves at deoxyuridine (dU) residues; Endonuclease V, which cleaves DNA at deoxyinosine (dI) and RNA at inosine (i) residues; a restriction endonuclease; a ribozyme or deoxyribozyme; RNase H; RNase H II, Duplex-specific Nuclease (DSN); and Cas9 nuclease.

Reversible Blocking Groups

In some embodiments, the 5'- and/or 3'-end groups of the combo adapter may contain a reversible blocking group that requires chemical, photochemical or enzymatic conversion to unblock, repair or activate the end group converting said blocking group active groups prior to the circularization step. Non-limiting examples of reversible blocking groups are 3'-phosphate (3'-p), 2'-phosphate (2'-p), 2',3'-cyclic phosphate (2',3'>p), 3'-O-(3-methoxyethyl)ether, and 3'-O-isovaleryl ester, 5'-ppp, 5'-p and 5'-OH. Non-limiting examples of active groups are 2'-OH/3'-OH. A chemical group may be an active group or a reversible blocking group depending on the ligase used. For example, 3'-OH may be an active group for 3'-OH ligase and a blocking group for 5'-OH ligase; 3'-p may be an active group for 5'-OH ligase and a blocking group for 3'-OH ligase; 5'-OH may be an active group for 5'-OH ligase and a blocking group for 3'-OH ligase; and 5'-p or 5'-App may be an active group for 3'-OH ligase and a blocking group for 5'-OH ligase.

The combo adapter may comprise a reversible 3'-end blocking group. The combo adapter may be ligated to the 3' end of the sample polynucleotide, further comprising converting the reversible 3'-end blocking group to a 2'-OH/3'-OH group before circularizing. The reversible 3'-end blocking group may be selected from: 3'-phosphate (3'-p), 2'-phosphate (2'-p), 2',3'-cyclic phosphate (2',3'>p), 3'-O-(3-methoxyethyl)ether, and 3'-O-isovaleryl ester. The 3'-p, 2'-p and 2',3'>p groups may be converted to 2'-OH/3'-OH by a polynucleotide kinase (PNK) either in the absence or presence of ATP. The 3'-p and 2'-p groups (but not 2',3'>p) end groups may be converted to 2'-OH/3'-OH by an alkaline phosphatase. The said alkaline phosphatase may be selected from: Calf Intestinal phosphatase (CIP), Shrimp Alkaline Phosphatase (rSAP), APex™ Heat-labile alkaline phosphatase and Antarctic Phosphatase. The combo adapter may comprise a reversible 5'-end blocking group. The reversible 5'-end blocking group may be selected from: 5'-ppp, 5'-p or 5'-OH. The combo adapter may be ligated to the 5' end of the sample polynucleotide, further comprising converting 5'-OH to 5'-p or 5'-ppp to 5'-p before circularizing by a 3'-OH ligase, or converting 5'-p to 5'-OH before circularizing by a 5'-OH ligase. The 5'-OH group may be converted to 5'-p by polynucleotide kinase in the presence of ATP. The 5'-OH group may be converted to 5'-p in the presence of ATP by a polynucleotide kinase that also simultaneously removes 3'-p, 2'-p and 2',3'>p. The 5'-p group may be converted to 5'-OH without removal of 3'-p, 2'-p and 2',3'>p (which groups in some cases may be required by a 5'-OH ligase) by a modified polynucleotide kinase derivative lacking 3'-end phosphatase activity in the absence of ATP and optional presence of ADP. The 5'-ppp group may be converted to 5'-p by a pyrophosphatase or by RNA 5' polyphosphatase.

The CAD may comprise a reversible blocking group that prevents unwanted ligation and/or circularization in the absence of a chemical or enzymatic modification of the reversible blocking group. The reversible blocking group may also be referred to herein as the blocking group. The splint oligonucleotides, RT-blocker and PCR blocker oligonucleotides may themselves also have at least one terminal blocking group preventing its ligating or extending.

In some embodiments, the CAD comprises at least one terminal residue that contains a reversible blocking group which requires chemical, photochemical or enzymatic modification to convert them into active groups prior to ligating and/or circularizing.

In some embodiments, the CAD is a 5'-CAD. The 5'-CAD may be ligated to the 5' end of the sample polynucleotide. In some embodiments, the CAD comprises a nucleoside residue at its 3' end selected from: uridine (U or rU), deoxyuridine (dU), deoxythymidine (dT), ribothymidine (rT), cytosine (C or rC), deoxycytosine (dC), adenosine (A or rA), deoxyadenosine (dA), guanosine (G or rG), deoxyguanosine (dG), inosine (I or rI), and deoxyinosine (dI). In some embodiments, 5'-CAD comprises 5'-OH and 3'-OH end groups and wherein, after ligation of the CAD to the 5'-end of the sample polynucleotide, the 5'-OH group of the polynucleotide-CAD ligation products is converted to 5'-phosphate before the circularization step.

In some embodiments, the CAD is a 3'-CAD. In some embodiments, 3'-CAD comprises a 5'-phosphate (5'-p) or 5'-adenylated (5'-App) group and a reversible 3'-end-blocking group which is converted into a 3'-OH group before circularizing. In some embodiments, the reversible 3'-end-blocking group is selected from: 3'-phosphate (3'-p), 2',3'-cyclic phosphate (2',3'>p), 3'-O-(α-methoxyethyl)ether, and 3'-O-isovaleryl ester.

In some embodiments, the 5' proximal segment comprises DNA. In some embodiments, the 5' proximal segment comprises RNA. In some embodiments, the 5' proximal segment comprises a combination of RNA and DNA. In some embodiments, the 3' proximal segment comprises DNA. In some embodiments, the 3' proximal segment comprises RNA. In some embodiments, the 3' proximal segment comprises a combination of RNA and DNA.

Sample Polynucleotides

Disclosed herein are methods, compositions and kits for the detection for sample polynucleotides. The sample polynucleotide may comprise RNA. The sample polynucleotide may comprise fragmented RNA. The sample polynucleotide may comprise partially degraded RNA. The sample polynucleotide may comprise a microRNA or portion thereof. The sample polynucleotides may comprise an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA; a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof. The circRNA may be cleaved or fragmented. As used herein, the term "cleaved" generally refers to a site-specific chemical break or nuclease-induced break of the nucleic acid, whereas "fragmented" generally refers a break caused by a random degradation of the nucleic acid to smaller fragments. The RNA may be single-stranded RNA, double-stranded RNA or denaturing double-stranded RNA.

The sample polynucleotide may comprise DNA. The sample polynucleotide may comprise a denatured DNA molecule or fragment thereof. The sample polynucleotide may comprise DNA selected from: genomic DNA, viral DNA, mitochondrial DNA, plasmid DNA, amplified DNA, circular DNA, circulating DNA, cell-free DNA, or exosomal DNA. The DNA may be single-stranded DNA (ssDNA), double-stranded DNA, denaturing double-stranded DNA, synthetic DNA, and combinations thereof. The circular DNA may be cleaved or fragmented.

The sample polynucleotide may be less than about 200 nucleotides long. The sample polynucleotide may be less than about 190 nucleotides long. The sample polynucleotide may be less than about 190 nucleotides long. The sample polynucleotide may be less than about 180 nucleotides long. The sample polynucleotide may be less than about 170 nucleotides long. The sample polynucleotide may be less than about 160 nucleotides long. The sample polynucleotide may be less than about 150 nucleotides long. The sample polynucleotide may be less than about 140 nucleotides long. The sample polynucleotide may be less than about 130 nucleotides long. The sample polynucleotide may be less than about 120 nucleotides long. The sample polynucleotide may be less than about 110 nucleotides long. The sample polynucleotide may be less than about 100 nucleotides long. The sample polynucleotide may be less than about 95 nucleotides long. The sample polynucleotide may be less than about 85 nucleotides long. The sample polynucleotide may be less than about 75 nucleotides long. The sample polynucleotide may be less than about 65 nucleotides long. The sample polynucleotide may be less than about 55 nucleotides long. The sample polynucleotide may be less than about 45 nucleotides long. The sample polynucleotide may be less than about 35 nucleotides long. The sample polynucleotide may be less than about 25 nucleotides long. The sample polynucleotide may be less than about 15 nucleotides long.

The sample polynucleotide may have a length of about 5 nucleotides to about 150 nucleotides. The sample polynucleotide may have a length of about 8 nucleotides to about 120 nucleotides. The sample polynucleotide may have a length of about 10 nucleotides to about 115 nucleotides. The sample polynucleotide may have a length of about 10 nucleotides to about 100 nucleotides. The sample polynucleotide may have a length of about 10 nucleotides to about 90 nucleotides.

In some embodiments, the sample polynucleotide has a length of about 19 nucleotides to about 40 nucleotides. For example, the sample polynucleotide may be a miRNA or other small non-coding RNA, or fragments of large RNAs such as ribosomal RNA, mRNA, large non-coding RNAs or viral RNAs. However, some methods of the invention are not limited to small RNAs and are equally applicable for any RNA that can be circularized.

The sample polynucleotide may have a length of a miRNA. The length of miRNA is typically about 22 nucleotides. Therefore the sample polynucleotide may have a length of about 18 nucleotides, about 20 nucleotides, about 22 nucleotides, or about 24 nucleotides.

The sample polynucleotide may comprise a 5'-phospate (5'-p) or other naturally existing 5'-end group such as: cap, 5'-triphosphate (5'-ppp), and 5'-hydroxyl (5'-OH) that can be converted to 5'-p or 5'-OH before the ligating and/or circularizing. The sample polynucleotide may contain a 5'-p or a 5'-OH group that can be directly used for ligating and/or circularizing without said converting.

The sample polynucleotide may comprise a 3'-phosphate (3'-p), 2'-phosphate (2'-p) or 2',3'-cyclic phosphate (2',3'>p) ends, which can be converted to 3'-OH before the ligating and/or circularizing. Alternatively, the sample polynucleotide may comprise a 3'-hydroxyl (3'-OH) which can be converted to 3'-p or 2',3'>p before the ligating and/or circularizing. The sample polynucleotide may contain 3'-OH, 3'-p or 2,3'>p group which can be directly used for said the ligating and/or circularizing without said converting. The 3' end of the sample polynucleotide may comprise a 2'-OH, 2'-p or 2'-OMe.

In a particular embodiment of the invention, the sample polynucleotide sample polynucleotide comprises the following features: a) size ranging from 10 to 100 nucleotides (nt); b) 5'-phospate (5'-p) or other naturally existing 5'-end group such as: cap, 5'-triphosphate (5'-ppp), and 5'-hydroxyl (5'-OH) that can be converted to 5'-p before the ligation and/or circularization; c) 3'-phosphate (3'-p), 2'-phosphate (2'p) or 2',3'-cyclic phosphate (2',3'>p).

Samples

In certain embodiments of the invention, multiple sample polynucleotides are simultaneously detected in a plurality of samples.

The sample may be a biological sample. The biological sample may be selected from a plant sample, an animal sample, a bacterial sample, a fungal sample, and a combination thereof. The animal sample may be a mammalian sample. The animal sample may be a human sample. The human sample may be a biopsy sample. The biopsy sample may be malignant. The biopsy sample may be benign. The biopsy sample may be obtained from any tissue (e.g., breast, colon, muscle, fat, pancreas, spleen, brain, etc.).

The biological sample may comprise a biological fluid. The biological fluid may be a bodily fluid. The bodily fluid may be, by way of non-limiting example, blood, serum, plasma, saliva, tears, mucus, urine, semen, and sweat.

The biological sample may be selected from skin and hair. The biological sample may be obtained by a swab.

The sample may be a clinically relevant sample. The clinically relevant sample may comprise healthy tissue. The clinically relevant sample may comprise diseased tissue. The clinically relevant sample may comprise potentially diseased tissue. The clinically relevant sample may comprise a tumor-harboring tissue or portion thereof. The clinically relevant sample may comprise a tumor or portion thereof. The sample may be a formalin-fixed paraffin-embedded (FFPE) tissue samples. The biological sample may comprise a crude nucleic acid (RNA and DNA) extract.

The sample may be selected from: total RNA extracts (DNA free); total DNA extracts (RNA free); size-fractioned nucleic acid (RNA or DNA) isolates; size-fractioned fragmented nucleic acids (RNA or DNA) preparations; and target-enriched nucleic acid preparations (DNA or RNA).

Kits

Disclosed herein are kits for preparing an RNA sequencing library comprising a combo adapter disclosed herein. The kit may comprise PCR primers capable of amplifying a nucleic acid complementary to a sample polynucleotide, wherein the combined length of the PCR primers is greater than 24 nucleotides. The RNA sequencing library may be a miRNA sequencing library.

Disclosed herein are kits for detecting sample polynucleotides. In some embodiments, the kit may be used to prepare RNA sequencing libraries. The RNA sequencing library, by way of non-limiting example, may be a miRNA sequencing library. The kit may comprise any combo adapter or combination of combo adapters described herein.

The kit may further comprise reagents, enzymes and/or buffers required to perform reactions such as ligations, reverse transcription, nucleic acid amplification (e.g., PCR), and sequencing.

The kit may comprise at least one PCR primer capable of amplifying the sample polynucleotide(s). The PCR primer may be capable of binding/annealing to a sequence of the CAD or portion thereof, or complement thereof. The kit may comprise a forward primer and a reverse primer. The combined length of the forward primer and a reverse primer may be greater than about 15 nucleotides. The combined length of the forward primer and a reverse primer may be greater than about 18 nucleotides. The combined length of the forward primer and a reverse primer may be greater than about 20 nucleotides. The combined length of the forward primer and a reverse primer may be greater than about 22 nucleotides. The combined length of the forward primer and a reverse primer may be greater than about 24 nucleotides. The combined length of the forward primer and a reverse primer may be greater than about 25 nucleotides. The combined length of the forward primer and a reverse primer may be greater than about 26 nucleotides. The combined length of the forward primer and a reverse primer may be greater than about 28 nucleotides.

Uses

The methods, compositions, and kits disclosed herein find use in a number of applications, such as applications that benefit from utilization of a monomeric complementary nucleic acids (cNAs). For example, applications comprising the detection and/or quantification of sample polynucleotides, construction of small RNA libraries for sequencing, microarray and RT-qPCR can benefit from methods, compositions, and kits for reducing and/or preventing the formation of multimeric products of Rolling-Circle Amplification (RCA), ligation bias, amplification bias, and sequencing bias.

Sequencing Libraries

Further disclosed herein are sequencing libraries comprising a plurality of adapter-polynucleotide ligation products, wherein at least one of the adapter-polynucleotide ligation products of the plurality adapter-polynucleotide ligation products comprises: a) a sample polynucleotide; and b) a combo adapter disclosed herein. At least one of the adapter-polynucleotide ligation products may be circularized.

The methods, compositions, and kits disclosed herein may be used to prepare nucleic acid sequencing libraries. By way of non-limiting example, the nucleic acid sequencing library may be an RNA library. The RNA library may be a miRNA library. The RNA library may be a small RNA library. The RNA library may be a fragmented (naturally or artificially) RNA library. By way of non-limiting example, the nucleic acid sequencing library may be a DNA library. The DNA library may be a fragmented (naturally or artificially) DNA library. In some embodiments, the methods, compositions, and kits disclosed herein may be used to produce a plurality of monomeric nucleic acids, wherein each monomeric nucleic acid comprises a detection sequence and a sequence complementary to a sample polynucleotide. The detection sequence may enable sequencing of the sample polynucleotide. The detection sequence, by way of non-limiting example, may be an annealing/binding site for a sequencing primer.

Disclosed herein are uses of combo adapters to prepare sequencing libraries, wherein the combo adapters comprise nucleic acid residues; a 5'-proximal segment and a 3'-proximal segment, wherein each proximal segment comprises at least one sequencing adapter; a template-deficient segment for primer extension by a polymerase, wherein the template-deficient segment prohibits rolling-circle amplification; and a 5' end and a 3' end that allow: i) intermolecular ligation of said combo adapter to a sample polynucleotide to produce an polynucleotide-CAD ligation product; and ii) circularization of the polynucleotide-CAD ligation product to produce a circularized polynucleotide.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Ligation of miRNAs with CAD

This example is depicted in Step 1 of FIG. 7. A set of 8 human (hsa-) miRNAs were used: miR-16-5p, UAGCAGCACGUAAAUAUUGGCG (SEQ ID NO. 1), miR-31-5p, AGGCAAGAUGCUGGCAUAGCU (SEQ ID NO. 2), miR-125b, UCCCUGAGACCCUAACUUGUGA (SEQ ID NO. 3), miR-141-3p, UAACACUGUCUG-GUAAAGAUGG (SEQ ID NO. 4), miR-145-5p, GUCCAGUUUUCCCAGGAAUCCCU (SEQ ID NO. 5), miR-191-5p, CAACGGAAUCCCAAAAGCAGCUG (SEQ ID NO. 6), miR-524-5p, CUACAAAGGGAAGCACUUU-CUC (SEQ ID NO. 7), and miR-545-3p, UCAGCAAA-CAUUUAUUGUGUGC (SEQ ID NO. 8), chosen to represent various degrees of bias based on a previous miRNA sequencing study using TruSeq kit for small RNA library preparation (Illumina).

Figure 8A:
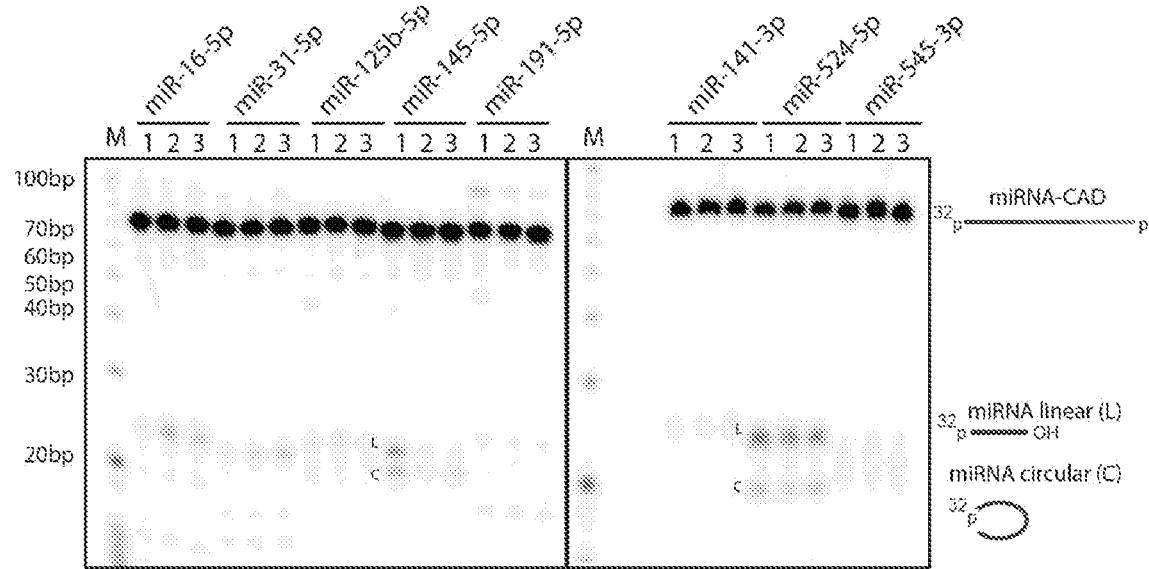
FIG. 8A: Analysis of products of ligation between CAD and selected synthetic miRNAs. A pre-adenylated CAD (5'-AppCAD-3'-p) was ligated with miRNAs using a T4 RNA ligase 2 derivative in the absence of ATP (Step 1 in FIG. 7). The ligation reactions were analyzed by denaturing gel electrophoresis along with a DNA ladder as marker (M). L and C are unreacted linear and circularized forms of miRNAs, respectively.
Figure 8B:
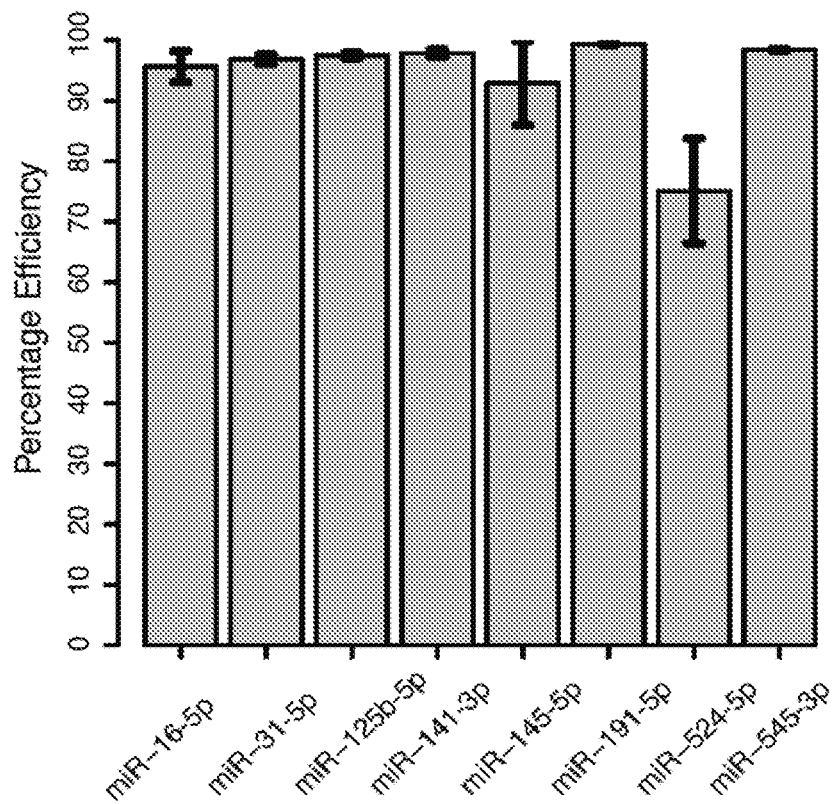
FIG. 8B: Different miRNAs produce similar yields of miRNA-CAD ligation products. The yields for the CAD ligation to individual miRNAs were determined using data from FIG. 8A. Error bars represent the standard deviation of three replicates (±S.D.)

These synthetic miRNAs (IDT) containing 5'-phosphate and 3'-OH ends were subjected to ligation with a combo adapter (CAD) that had the following features: (i) standard TruSeq 3'-adapter DNA sequence as 5' segment, (ii) standard TruSeq 5'-adapter RNA sequence as 3' segment, (iii) an abasic spacer connecting these 5' and 3' segments, and (iv) 3'-p at the 3'-end. CAD derivatives having an additional 2 random nucleotides at the 5' end (5'-NN), or a single additional terminal nucleotide (selected from A, G, C or U) at the 3' end (3'-N) were also tested. The CAD, 5'-AppTGGAATTCTCGGGTGCCAAGG-idSp/idSp-r (GUUCAGAGUUCUACAGUCCGACGAUCU)p-3' (SEQ ID NO. 9) (where idSp is a stretch of two abasic 1',2'-dideoxyribose residues, dSpacers), provided the most efficient ligation to all tested miRNAs. There was no advantage of using the 5'-NN variants, but an additional 3'-U nucleotide provided the most efficient circularization of miRNA-CAD ligation product (see Example 2). The 5'-phosphorylated CAD precursor (5'-pCAD, purchased from IDT) was pre-adenylated using a 5' DNA/RNA Adenylation kit (NEB) and the resulting pre-adenylated CAD (5'-AppCAD) was gel-purified. The gel-purified 5'-AppCAD (6 pmoles) was incubated with trace amounts of 5'-$^{32}$P-labeled miRNAs in the presence of 20 U/µl T4 RNA ligase 2 truncated, K227Q-mutant (Rnl2trKQ) (NEB) using Rnl2trKQ ligation buffer containing 10% PEG 8000 and no ATP for 2 h at 30° C. (reaction volume, 10 µl). Both CAD and miRNAs were heated to 70° C. for 2 min and then cooled (miRNAs were placed on ice; CAD was cooled to 25° C. at the rate of 0.1° C./sec) before mixing them together. The ligation reactions were run in triplicate and the products were analyzed by denaturing 15% PAGE (FIG. 8A). The yields for the miRNA-CAD ligation products were calculated using phosphorimaging data. The majority of tested miRNAs were ligated to CAD with ≥95% yield, except miR-524, which was ligated with average yield of ~75% (FIG. 8B).

A reduction in the sequencing bias can be achieved if all enzymatic steps have similar efficiency for all miRNAs being examined. Efficiency should be reasonably high but it is more important that it be consistent than that it be 100%; hence shorter, more convenient reaction times that satisfy these criteria may be acceptable.

Alternative enzymes that may replace or be used in addition to Rnl2trKQ include: T4 RNA Ligase 2 (truncated, R55K, K227Q), and thermostable 5"AppDNA/RNA Ligase (both from NEB).

Figure 9A:
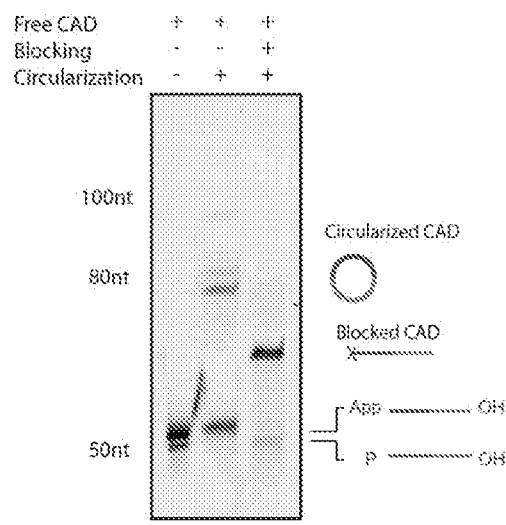
FIG. 9A: CAD blocking prevents its circularization and multimerization. Treatment of unblocked, 3'-dephosphorylated 5'-AppCAD-3'-OH with CircLigase resulted in partial conversion into circular monomer and dimer products (middle lane). To block the free CAD (Step 2 in FIG. 7), an equimolar mixture of two blocking oligonucleotides were ligated to 5'-AppCAD-3'-p by T4 DNA ligase (see left panel in FIG. 5B) and then dephosphorylated at their 3' end by PNK (Step 3 in FIG. 7). After treatment with CircLigase, the blocked CAD did not form detectable amounts of circular CAD products in the circularization reaction described above (right lane). 3'-dephosphorylated 5'-AppCAD and 5'-pCAD are shown as controls in the left lane.

Example 2. Blocking Free CAD Allows Selective Circularization of miRNA-CAD Ligation Products Two techniques were tested to block free, unligated CAD from Example 1 by ligating it to blocking oligonucleotides after the ligation of miRNAs with CAD (Step 2 in FIG. 7). The first technique involved use of an RNA anchor probe, 5'-biotin-TEG-AAAAA (IDT) (SEQ ID NO. 10), where TEG is triethyleneglycol, using either the thermostable RNA ligase TARnl or Rnl2trKQ. The second technique involved the use of splint-dependent ligation of CAD with blocking oligonucleotide (BLO) by T4 DNA ligase or T4 RNA ligase 2. The BLO, 5'-biotin-TEG-AAAAAAAAAA (IDT) (SEQ ID NO. 11), has a 3'-OH, which allows ligation to 5'-ends of both 5'-AppCAD and its precursor 5'-pCAD. Small amounts of 5'-pCAD may be co-purified with the 5'-AppCAD as well as formed as a product of a de-adenylation side reaction with Rnl2trKQ during ligation of 5'-AppCAD with miRNAs. The splint oligonucleotide (SPO), 5'-AmMC6-GAGAAT-TCCATTTTTTTTT-3'-AmMO (SEQ ID NO. 12), is complementary to both the CAD and the BLO. The SPO has blocking groups at both ends (5'-AmMC6, or 5' Amino Modifier C6 group; and 3'-AmMO, or 3' Amino Modifier group) preventing their interference with the ligation or primer extension. Free 5'-AppCAD, when 3'-dephosphorylated by PNK, was circularized by CircLigase (see FIG. 9A, lanes 1-2). However, the blocking reaction using BLO, SPO and T4DNA ligase almost quantitatively converted 5'-App-CAD into a ligation product that cannot be circularized (see FIG. 9A, lane 3).

The blocking reactions (Step 2 in FIG. 7) were performed by hybridizing an equimolar mixture of blocking oligonucleotides BLO and SPO (25 pmoles of each) with 10 ng/µl 5'-AppCAD, which included heating to 65° C. for 20 min followed by cooling to 25° C. at the rate of 0.1° C./sec. Then ligation was performed by 133 U/µl T4 DNA ligase (NEB) in Rnl1 buffer (NEB) with added 1 mM ATP and incubation for 60 min at 25° C. (reaction volume, 15 µl). The 3'-dephosphorylation reaction (Step 3 in FIG. 7) was performed in the presence of 0.5 U/µl T4 polynucleotide kinase (PNK) in Rnl1-buffer (NEB) with added 1 mM ATP and 10% PEG 8000 and incubation for 60 min at 37° C. (reaction volume, 10 µl). The circularization reactions (Step 4 in FIG. 7) were performed in the presence of 5 U/µl CircLigase (Epicentre) using CircLigase buffer (5 mM $Mg^{2+}$, 0.05 mM ATP and 10% PEG 8000) and incubation for 30 min at 64° C. (reaction volume, 20 µl). The reaction products were resolved on denaturing 15% PAGE and stained by SYBR Gold.

The second technique provided more efficient blocking of the free unligated CAD and preventing its circularization or formation of multimers. The linear (non-circularized) CAD cannot be converted to the RT-PCR amplicons required for sequencing and, therefore, do not generate sequencing reads. Optimizing the efficiency of CAD blocking reduces the fraction of "empty" PCR amplicons that lack miRNA sequence inserts and allows use of smaller amounts of input RNA for sequencing library preparation. It may also eliminate the need for gel-purification of the PCR amplicons. Such optimization may be accomplished, for example, by use of RNA ligase 2 (rather than T4 DNA ligase) and changing certain residues at the ends of the blocking oligo-nucleotides and CAD molecules from DNA to RNA.

Figure 9B:
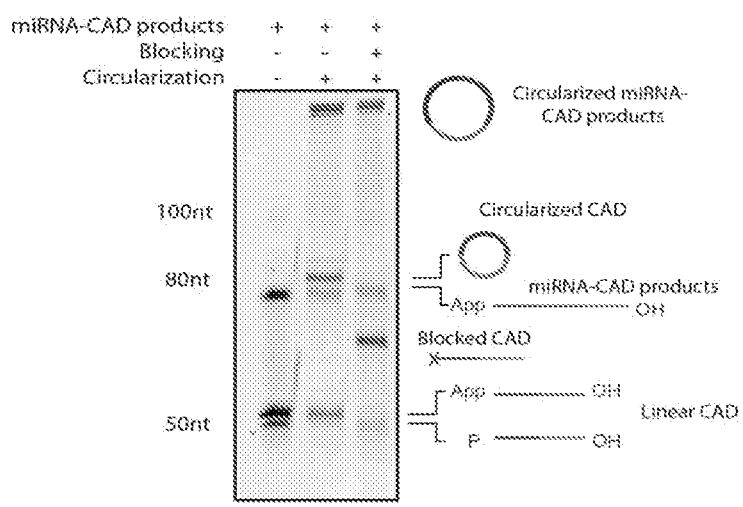
FIG. 9B: CAD blocking provides selective miRNA-CAD circularization. 3'-dephosphorylated miRNA-CAD ligation products prepared in multiplex by CAD ligation with selected miRNAs are seen along with excess unligated/free 5'-AppCAD in the left lane. Multiplex circularization of these products without blocking the free 5'-AppCAD-3'-OH (Step 4 in FIG. 7) produces a high yield (~85%) of miRNA-CAD circles, but also results in partial circularization of CAD (middle lane). However, if the CAD is blocked prior to circularization (right lane), CAD circles are largely eliminated and the yield of miRNA-CAD circles remains high (~80%).
Figure 9C:
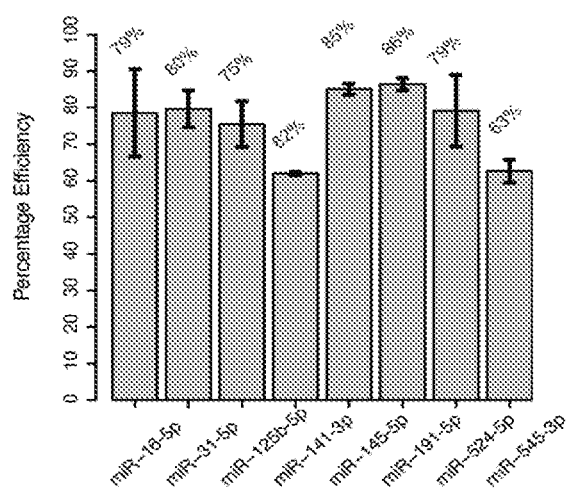
FIG. 9C: Yields of miRNA-CAD circularization are similar for different miRNAs. The CAD ligation, dephosphorylation, blocking and circularization reactions were performed in singleplex for selected individual miRNAs as described in the legends to FIG. 7 and FIG. 8A-B. The products of circularization reactions were analyzed by gel-electrophoresis and the yields of circularized miRNA-CAD products were determined.

Efficiency of circularization of the 3'-dephosphorylated miRNA-CAD ligation products by several ligases was compared, including T4 RNA ligase 1 (Rnl1), thermostable RNA ligase (TAR) from NEB, CircLigase ssDNA ligase (CircLigase), CircLigase II and CircLigase RNA ligase (all CircLigases were from Epicentre). CircLigase provided more efficient circularization of miRNA-CAD products (when used alone) than the other tested ligases. For optimal activity with our substrate, CircLigase required the presence of ATP and absence of $Mn^{2+}$ cations. The average yield of circular miRNA-CAD products after incubation with CircLigase for 10 min at 64° C. was about 80% (FIG. 9B, right lane). The important finding was that the efficiency of circularization was very close (i.e., the circularization bias was low) for all tested miRNAs (FIG. 9C). Note that circular single-stranded polynucleotides (both RNA and DNA) that are longer than 42 nt have lower mobility than their linear forms in denaturing polyacrylamide gels (Harrison and Zimmerman 1984). In addition to their different gel mobilities, the identity of the circular and linear forms of CAD and miRNA-CAD products was confirmed by using RNase R and Exonuclease I, which can digest linear but not circular polynucleotides (data not shown).

The use of two ligase was also tested, Rnl1 and CircLigase, working in concert for circularization of miRNA-CAD products. It was reasoned that conducting two separate ligation reactions, with Rnl1 (at 37° C.) and CircLigase (at 64° C.), might additionally decrease the circularization bias for some miRNAs because these ligases may have different preferences for RNA terminal nucleotides and secondary structures. It was found that addition of 1 U/µl Rnl1 in the de-phosphorylation reaction by PNK (described above) did not interfere with dephosphorylation and resulted in simultaneous circularization of miRNA-CDA products. Surprisingly, similar yields of circular miRNA-CAD products were observed when Rnl1 combined with PNK were used in Step 3, whether Step 4 was performed or omitted.

Example 3. RT-PCR Amplification of Circular miRNA-CAD Products

Figure 10A:
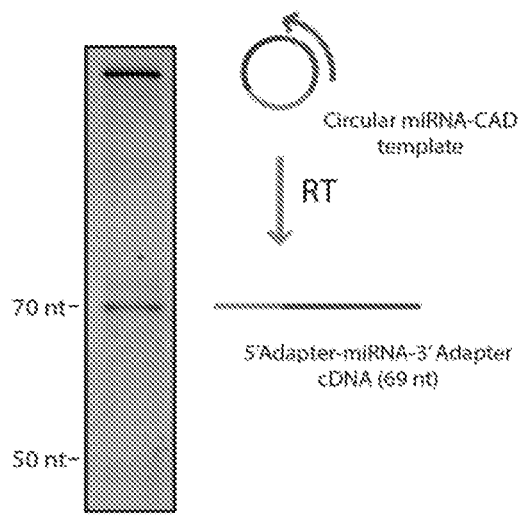
FIG. 10A: RT of circular miRNA-CAD (Step 5 in FIG. 7). The CAD ligation, dephosphorylation, blocking, circularization and RT reactions were performed in singleplex for selected individual miRNAs as described in the legends to FIG. 9C and FIG. 10A without purification of the intermediate reaction products. The RT products were analyzed by gel electrophoresis. The gel mobility of the circular miRNA-CAD product for miR-16 (shown here as an example) is slower than its linear version. The RT primer extension on the circular miRNA- CAD template for miR-16 (shown here as an example) results in a main cDNA product of 69 nt, the size expected for the miRNA insert flanked by the 5'- and 3'-adapters.
Figure 10B:
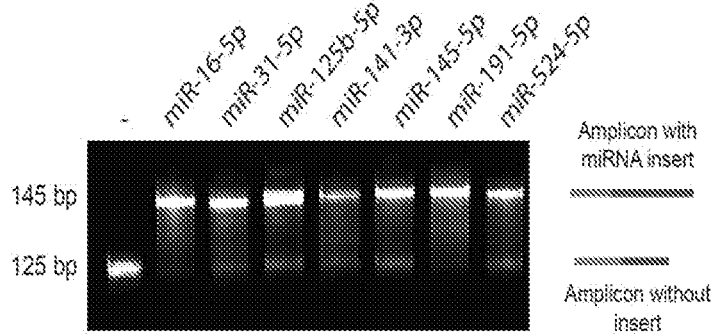
FIG. 10B: PCR amplification of the RT products (Step 6 in FIG. 7). The RT products for the selected miRNAs were amplified for 11 PCR rounds using the extended PCR primers which include Illumina's flow-cell binding sequences (P5 and P7). The PCR products were analyzed by gel electrophoresis. The size of the main PCR product was around 145 bp that was expected for P5-5'-adapter-miRNA-3'-Adapter-P7 amplicons, whereas the minor product of 125 bp corresponds to the amplification product for "empty" CAD without miRNA insert.
Figure 10C:
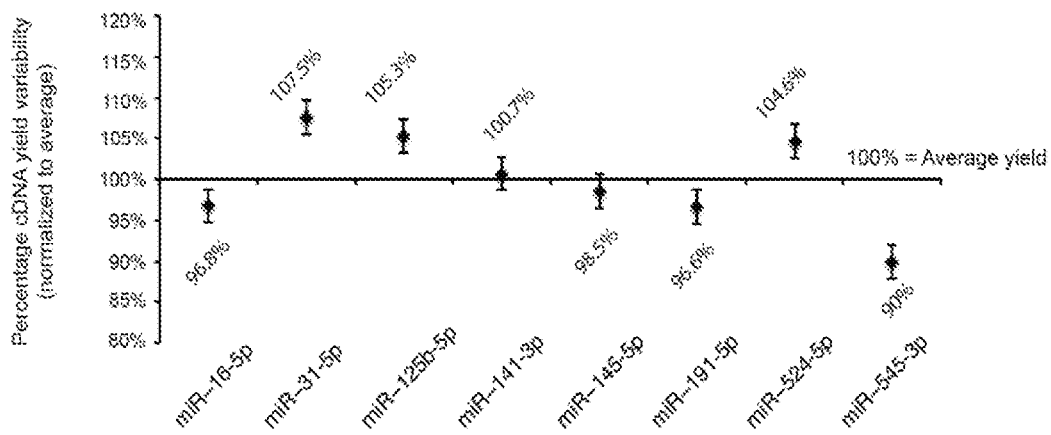
FIG. 10C: Similar yields of RT products for various miRNA sequences. The RT products for the selected miRNAs obtained as described in FIG. 10A were analyzed by gel electrophoresis. The yields of RT products for individual miRNA were determined, normalized and compared to the average yield of the RT products (shown as "100%").

Here, RT reactions were run with a 1-nt shorter (at its 5' end) version of the TruSeq RTP primer, CCTTGGCACCCGAGAATTCCA (RTP-1) (SEQ ID NO. 13), using the circularized miRNA-adapter products (from Example 2) as template. The RT reactions were performed in the presence of 0.2 µM RTP-1 primer and 10 U/µl SuperScript II in First-Strand buffer (Life Technologies) with added 0.5 mM dNTP mix and 10 mM DDT for 60 min at 42° C. (reaction volume, 20 µl). The reaction products were resolved on denaturing 15% PAGE and stained by SYBR Gold. Reverse transcriptases, SuperScript II (SSII) and SuperScript III (Life Technologies), were compared and it was found that SSII provided a higher yield of the expected monomeric cDNA product of ~70 nt, containing an miRNA insert flanked by TruSeq 5'-adapter at the miRNA's 5' end and 3'-adapter at its 3' end. The RT products for miR-16-5p (as an example) are shown in FIG. 10A. The yields of the RT products for all selected miRNAs were within ±10% of one another (FIG. 10C). Note that this very low variability (bias) reflected the entire procedure, Steps 1 through 5 of the RealSeq® scheme (FIG. 7) rather than the RT step alone.

The RT reaction products described above were PCR amplified using the standard TruSeq PCR primers: RP1 (AATGATACGGCGACCACCG AGATCTACACGTTCAGAGTTCTACAGTCCG) (SEQ ID NO. 14) and RPI41 (CAAGCAGAAGACGGCATACGAGATGTCGTCGTGACTGGAGTTCCTTGGCACCCGAGAATTCCA (SEQ ID NO. 15). The PCR products for the selected miRNAs are shown in FIG. 10B. The size of the main PCR amplicon was ~145 bp, which corresponds to the expected 5'-adapter-miRNA-3'Adapter amplicons. Only very small amounts of amplified "empty" CAD amplicons of 125 bp, which have no miRNA insert, were detected, validating the efficiency of the adapter blocking method (Step 2 in FIG. 7). The variability of the yields of PCR products after 11 PCR cycles for the eight miRNAs was within ±35%. The small increase in the bias from RT Step 5 (±10%) to PCR Step 6 (±35%) is most probably the result of PCR bias, which can be reduced by running fewer rounds (e.g., 9 rather than 11) of PCR amplification.

Example 4. Distribution of Sequencing Reads in the Sequencing Libraries for the Universal Reference Pool of miRNAs Prepared Using Different Methods The sequencing libraries were prepared using 1 pmole of the miRXplore™ Universal Reference pool (Miltenyi Biotec) containing equimolar amounts of 962 synthetic miRNAs, using RealSeq® (FIG. 7) and the TruSeq Small RNA library preparation kit v.1.5 (Illumina). The RealSeq® protocol combined all 6 Steps described in FIG. 7 and Examples 1 through 3 with inclusion of 1 U/µl Rnl1 in Step 3 in addition to PNK (see Example 2). For all library preparations, PCR amplicons of the desired size were gel-purified according to the standard Illumina protocol. The purified libraries were sequenced on a MiSeq instrument (Illumina), resulting in $1.0 \times 10^7$ reads. Sequencing reads were trimmed of adaptor sequences by using Cutadapt (Martin, M. et al. 2011. *EMBnet.journal* 17: 10-12) and trimmed reads were aligned to a custom miRNA reference file using Bowtie2 (Langmead, B., Salzberg, S. L. 2012. *Nat. Methods* 9: 357-9). Reads mapping to miRNAs were counted using a custom script. Fold changes were calculated assuming an equimolar representation of miRNAs in the synthetic pool; fold changes are plotted as $log_e$ values. The sequencing frequencies for miRNAs within a two-fold deviation from the expected values (area between vertical lines) were considered as unbiased according to Fuchs, R. T. et al. 2015. *PLoS One* 10: e0126049.

Figure 11A:
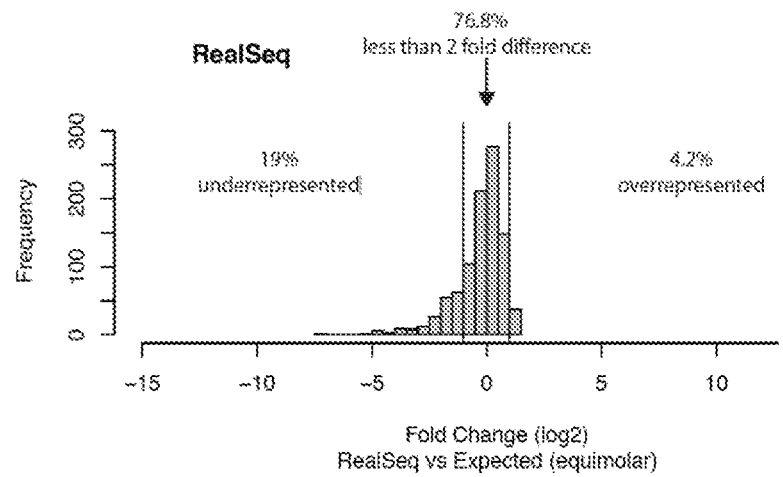
FIG. 11A: RealSeq® protocol.
Figure 11B:
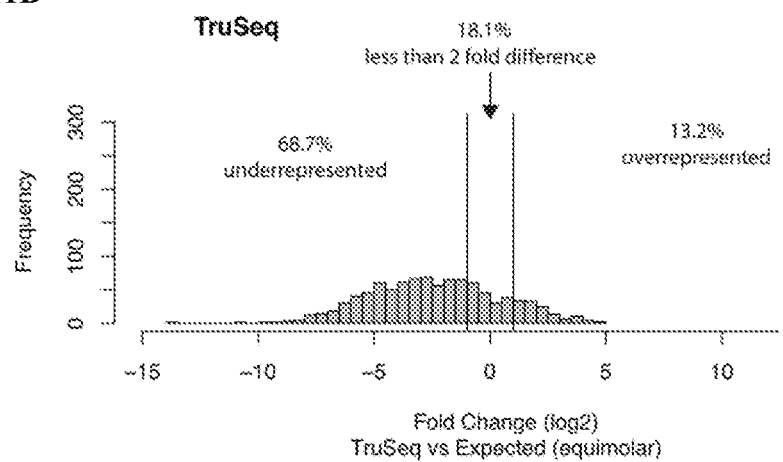
FIG. 11B: TruSeq® Small RNA library preparation kit v.1.5 and protocol (Illumina).
Figure 11C:
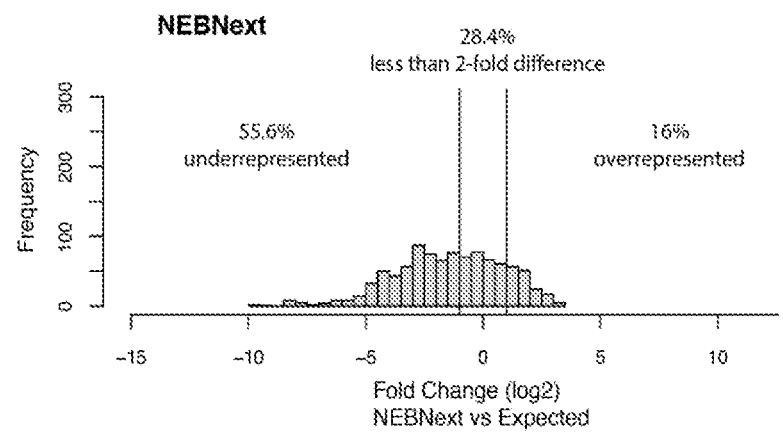
FIG. 11C: NEBNext® Small RNA Library Prep Set for Illumina (New England Biolabs/NEB).

The sequencing of these libraries showed that RealSeq® (FIG. 11A) strongly outperforms both Illumina's TruSeq® (FIG. 11B) as well as NEBNext® Small RNA Library Prep Set (NEB) (FIG. 11C, determined using Supplementary data from Fuchs et al. 2015). Fold changes between the sequencing reads mapped to individual miRNAs were calculated assuming an equimolar representation of miRNAs in the synthetic pool and plotted as $log_2$ values. The sequencing frequencies for miRNAs within a 2-fold deviation from the expected values (area between vertical lines) were considered as unbiased. The RealSeq® protocol provided quantification (by number of reads) of 76.8% of miRNAs (FIG. 11A) to within a two-fold deviation from the expected value (area between vertical lines, generally considered as unbiased) whereas with TruSeq and NEB kits, only 18.1 and 29.0% of miRNAs were detected within this range, respectively, and much higher fractions of miRNAs were under- or over-represented than with RealSeq®.

Figure 12A:
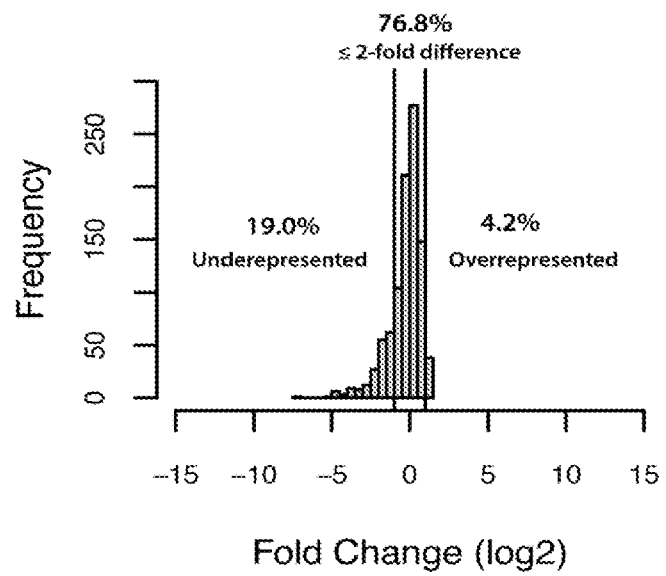
FIG. 12A: Using two consecutive circularization reactions. The first circularization occurs simultaneously with 3'-p dephosphorylation (Step 3 in FIG. 7) using a mix of PNK and T4 RNA ligase 1 (Rnl1). The products of this reaction are then treated with CircLigase (Step 4 in FIG. 7).
Figure 12B:
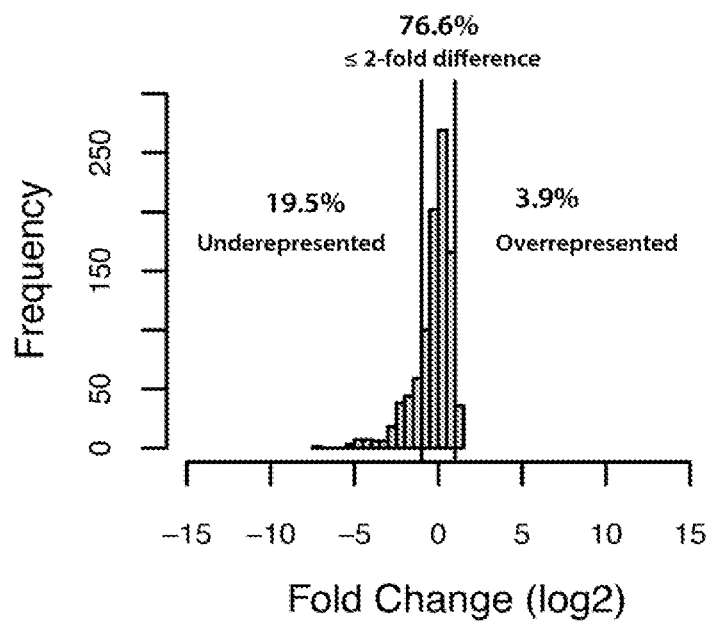
FIG. 12B: Same as (12A) but without the CircLigase treatment. The only circularization reaction is performed simultaneously with 3'-p dephosphorylation by a mix of PNK and Rnl1.

Example 5. Distribution of Sequencing Reads in the Sequencing Libraries for the Universal Reference Pool of miRNAs Prepared Using RealSeq® Protocols Using Different Circularization Techniques Using the sequencing data, two circularization techniques (described in Example 2) were further compared for 8 miRNAs. One technique used two consecutive circularization reactions: first, simultaneously with the 3'-p dephosphorylation (Step 3 in FIG. 5) by a mix of PNK and T4 RNA ligase 1 (Rnl1); and second, by CircLigase (Step 4 in FIG. 5). The other technique used only the first circularization reaction performed simultaneously with 3'-p dephosphorylation by a mix of PNK and T4 RNA ligase 1 (Rnl1), skipping the CircLigase reaction. Both these techniques gave very similar distributions of Illumina sequencing reads in the sequencing libraries for the reference pool of 962 different miRNAs at equal concentrations (FIG. 12A-B). However, a detailed analysis of individual miRNA sequencing reads for these two circularization techniques revealed small differences in which miRNAs were underrepresented (see Table 1). Although the additional circularization step with CircLigase helped to reduce the number of underrepresented miRNAs by only 0.5%, it allowed unbiased detection of an additional 16 miRNAs from the pool. However, this result implies that for certain tasks (e.g., for mRNA-Seq or expression profiling of majority of miRNAs) the separate circularization step with CircLigase (Step 4 in FIG. 5) can be eliminated from the RealSeq® protocol.

TABLE 1 miRNAs underrepresented in sequencing libraries prepared using different ligases

| T4 RNA ligase 1 + CircLigase | T4 RNA ligase 1 only |
|---|---|
| HSA-miR-144 | HSA-miR-154 |
| HSA-miR-218 | RNO-miR-207 |
| MMU-miR-322 | HSA-miR-302B |
| HSA-miR-384-3P | HSA-miR-369-5P |
| MMU-miR-424 | MMU-miR-450B-3P |
| MMU-miR-463 | HSA-miR-453 |
| HSA-miR-485-3P | MMU-miR-501-5P |
| HSA-miR-488 | HSA-miR-518E |
| HSA-miR-609 | HSA-miR-519C-3P |
| HCMV-miR-US33-3P | HSA-miR-560 |
|  | HSA-miR-638 |
|  | MMU-miR-674*; RNO-miR-674-3P |
|  | MMU-miR-679 |
|  | MGHV-miR-M1-6 |

Example 6: Preparation of a miRNA Sequencing Library Using RNA Ligase 2 and RtcB Ligase A model synthetic miRNA, mir-191-5p, having 5'-p and a 3'-OH ends (SEQ ID 6) was dephosphorylated to convert its ends to 5'-OH and 3'-OH (SEQ ID NO. 16). Dephosphorylation was performed in a 10-µl reaction by a thermolabile alkaline shrimp phosphatase rSAP (NEB) in 1× CutSmart buffer (50 mM Potassium Acetate, 20 mM Tris-acetate, 10 mM Mg(OAc)$_2$, 100 µg/ml BSA, pH 7.9@25° C.) for 30 min at 37° C., followed by heat inactivation of the enzyme at 65° C. for 15 minutes. The dephosphorylated miRNA was then ligated to a combo adaptor (CAD) corresponding to SEQ ID NO. 17, which has the same sequence and design as the CAD from Example 1 (SEQ ID NO. 9) except that it has a 5'-p (rather than 5'-App). Before ligation, both the dephosphorylated miRNA and CAD were heated to 70° C. for 2 min and then cooled (miRNA was placed on ice; CAD was cooled to 25° C. at the rate of 0.1° C./sec) before mixing them together as described in Example 1.

In one experiment, the ligation between 5'-OH-miRNA-3'-OH and 5'-p-CAD-3'-p was performed by T4 RNA ligase 2 and the circularization of the resulting product 5'-OH-miRNA-CAD-3'-p was performed by RtcB ligase, as follows. A 10-µl ligation reaction was performed with T4 RNA ligase 2 (NEB) in RNA ligase 2 buffer (1×: 50 mM Tris-HCl, 2 mM MgCl$_2$, 1 mM DTT, 400 µM ATP, pH 7.5) in the presence of 15% PEG 8000 and RNAse Out (NEB) for 2 hours at 25° C., followed by a 15 min incubation at 65° C. for enzyme inactivation. Circularization was performed in a 20-µl reaction by combining 1 µl (15 pmol) RtcB ligase (NEB), 2 µl of 10×RtcB buffer (1×: 50 mM Tris-HCl, 75 mM KCl, 3 mM MgCl$_2$, 10 mM DTT, pH 8.3 @ 25° C.), 2 µl of 10 mM MnCl$_2$, 2 µl of 1 mM GTP and 2.5 µl of 50% PEG 8000, and 10.5 µL nuclease-free water and incubating for 1 hour at 37° C.

In a second experiment, the ligation between 5'-OH-miRNA-3'-OH and 5'-p-CAD-3'-p was performed by RtcB ligase and the circularization of the resulting product 5'-OH-miRNA-CAD-3'-p was performed by T4 RNA ligase 2, as follows. The ligation reaction was performed in a 10-µl reaction mixture by combining 1 µl (15 pmol) RtcB ligase (NEB), 1 µl of 10×RtcB buffer, 1 µl of 10 mM MnCl$_2$, 1 µl of 1 mM GTP and 1.5 µl of 50% PEG 8000 and 5.5 µl nuclease-free water and incubating at 25° C. for 2 hours. The circularization was performed in a 20-µl reaction by RNA ligase 2 as described above (ligation step) for 1 hour at 37° C.

Optional inactivation of RtcB ligase can be performed by using a Mn$^{2+}$-specific chelating agent, e.g., nitrilotriacetic acid (NTA), 1,2-cyclohexylenedinitrilotetraacetic acid (CDTA), diethylenetriaminepentaacetic acid (DTPA), or p-aminosalicyclic acid (PAS).

Circularized miRNA-CAD ligation products generated by one of the above methods can then be amplified by RT-PCR as described in Examples 2 and 3 to prepare a sequencing library.

What is claimed is:

1. An adapter in the form of a single-stranded nucleic acid comprising:
   a) a single-stranded 5'-proximal segment and a single-stranded 3'-proximal segment, wherein the single-stranded 5'-proximal segment and the single-stranded 3' proximal segment comprise a sequencing adapter, a detection sequence, or a combination thereof, wherein the adaptor comprises at least one DNA residue and at least one RNA residue;
   b) 5'-end and 3'-end groups that allow first and second consecutive ligation reactions either directly or after conversion of one or both 5'-end and 3'-end groups to ligatable 5'-end and ligatable 3'-end group(s); and
   c) a template-deficient segment linking the single-stranded 5' proximal segment and the single-stranded 3' proximal segment that restricts primer extension by a polymerase over the template-deficient segment, wherein the template-deficient segment is a non-nucleotide segment.

2. The adapter of claim 1, wherein the adapter comprises a modified nucleic acid residue.

3. The adapter of claim 1, wherein the adapter comprises a sequence selected from: a sequencing adapter, a primer binding site, a detection sequence, a probe hybridization sequence, a capture oligonucleotide binding site, a polymerase binding site, an endonuclease restriction site, a sequencing bar-code, an indexing sequence, a Zip-code, one or more random nucleotides, a unique molecular identifier (UMI), and a sequencing flow-cell binding site, and combinations thereof.

4. The adapter of claim 1, wherein the 5'-end or 3'-end of the adapter contains a reversible blocking group preventing circularization or concatamerization of the adapter while allowing its ligation with a sample polynucleotide, wherein the reversible blocking group requires chemical, photochemical or enzymatic conversion to active end group prior to the circularization of the adapter-polynucleotide ligation product.

5. The adapter of claim 4, wherein the reversible blocking group is a 3'-end-blocking group selected from: 3'-p, 2',3'-cyclic phosphate (2',3'>p), 3'-O-(α-methoxyethyl)ether, and 3'-O-isovaleryl ester.

6. A kit for preparing an RNA sequencing library comprising the adapter according to claim 1.

7. A plurality of the single stranded nucleic acid of claim 1.

8. The adapter of claim 1, wherein the non-nucleotide residue comprises a non-nucleotide residue selected from: an abasic site, a disulfide (S—S) internucleotide bond, and combinations thereof.

9. The adapter of claim 1, wherein the single-stranded 5'-proximal segment comprises at least one RNA residue and the single-stranded 3'-proximal segment comprises at least one DNA residue.

10. The adapter of claim 1, wherein the single-stranded 3'-proximal segment comprises at least one RNA residue and the single-stranded 5'-proximal segment comprises at least one DNA residue.

* * * * *